US010254285B2

(12) United States Patent
Di Vizio et al.

(10) Patent No.: US 10,254,285 B2
(45) Date of Patent: Apr. 9, 2019

(54) METHODS FOR DETECTING AND TREATING CANCER METASTASIS

(71) Applicant: Cedars-Sinai Medical Center, Los Angeles, CA (US)

(72) Inventors: Dolores Di Vizio, Los Angeles, CA (US); Michael R. Freeman, Los Angeles, CA (US); Matteo Morello, Beverly Hills, CA (US); Valentina R. Minciacchi, Los Angeles, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 14/883,421

(22) Filed: Oct. 14, 2015

(65) Prior Publication Data
US 2016/0061842 A1    Mar. 3, 2016

Related U.S. Application Data

(63) Continuation-in-part of application No. PCT/US2014/034245, filed on Apr. 15, 2014.

(60) Provisional application No. 61/812,212, filed on Apr. 15, 2013, provisional application No. 61/935,269, filed on Feb. 3, 2014.

(51) Int. Cl.
*A61K 45/06* (2006.01)
*C12Q 1/6886* (2018.01)
*G01N 33/574* (2006.01)

(52) U.S. Cl.
CPC ....... *G01N 33/57484* (2013.01); *A61K 45/06* (2013.01); *C12Q 1/6886* (2013.01); *C12Q 2600/112* (2013.01); *C12Q 2600/118* (2013.01); *C12Q 2600/178* (2013.01); *G01N 2800/56* (2013.01)

(58) Field of Classification Search
None
See application file for complete search history.

(56) References Cited

U.S. PATENT DOCUMENTS

| | | | |
|---|---|---|---|
| 6,258,540 B1* | 7/2001 | Lo .................. | C12Q 1/6879 435/440 |
| 6,355,623 B2* | 3/2002 | Seidman .......... | A61K 31/52 514/263.4 |
| 6,812,023 B1 | 11/2004 | Lamparski et al. | |
| 2006/0019256 A1* | 1/2006 | Clarke .............. | C12N 5/0695 435/6.14 |
| 2008/0199890 A1* | 8/2008 | Letai ................. | G01N 33/5011 435/7.23 |
| 2010/0184046 A1* | 7/2010 | Klass ................. | C12Q 1/6886 435/7.1 |
| 2010/0196426 A1 | 8/2010 | Skog et al. | |
| 2010/0304989 A1 | 12/2010 | Von Hoff et al. | |
| 2011/0200998 A1 | 8/2011 | Weichselbaum et al. | |
| 2014/0056807 A1 | 2/2014 | Di Vizio et al. | |
| 2014/0148350 A1* | 5/2014 | Spetzler ............. | G01N 33/574 506/9 |

FOREIGN PATENT DOCUMENTS

| | | |
|---|---|---|
| EP | 2986326 A2 | 10/2014 |
| WO | 2012115885 A1 | 8/2012 |
| WO | 2014172390 A2 | 10/2014 |

OTHER PUBLICATIONS

Zips et al. (In vivo, 2005, 19:1-7).*
Freshney (Culture of Animal Cells, A Manual of Basic Technique, Alan R. Liss, Inc., 1983, New York, p. 4).*
Tian, J et al. 2004 (Physiol Genomics, 17:170-182).*
Pritzker (Clinical Chemistry, 2002, 48:1147-1150).*
Adlard et al. (The Lancet Oncology, Feb. 2002, 3:75-82).*
Gerdes et al. (Front. Oncol. Dec. 18, 2014 doi: 10.3389/fonc.2014. 00366, pp. 1-12).*
Kaiser (Science, 2006, 313: 1370) f.*
PCT/US2014/034245 International Search Report and Written Opinion dated Nov. 7, 2014; 13 pages.
Chambers et al. Microvesicle-mediated release of soluble LH/hCG receptor (LHCGR) from transfected cells and placenta explants. Reproductive Biology and Endocrinology (2011). 9:64 (15 pages).
Cheruvanky et al. Rapid isolation of urinary exosomal biomarkers using a nanomembrane ultrafiltration concentrator. Am J Physiol Renal Physiol (2007). 292:F1657-F1661.
D'Asti et al. Oncogenic extracellular vesicles in brain tumor progression. Frontiers in Physiology (2012). 3:Article 294 (15 pages).
Di Vizio et al. Oncosome Formation in Prostate Cancer: Association with a Region of Frequent Chromosomal Deletion in Metastatic Disease. Cancer Research (2009). 69:5601-5609.
Di Vizio et al. Large Oncosomes in Human Prostate Cancer Tissues and in the Circulation of Mice with Metastatic Disease. The American Journal of Pathology (2012). 181(5):1573-1584.
Morello et al. Abstract 430: MiRNA profiling of prostate cancer cell-derived large oncosomes identifies a signature of invasion and metastasis. Cancer Reserach (2012). 72(5): Suppl 1(3 pages).
PCT/US2014/034245 International Preliminary Report on Patentability dated Oct. 20, 2015; 8 pages.
EP Application No. 14785880.7 Extended Search Report dated Dec. 19, 2016; 13 pages.
Morello et al. Large oncosomes mediate intercellular transfer of functional microRNA. Cell Cycle (2013). 12(22):3526-3536.
Myers et al. Successful Treatment of Advanced Metastatic Prostate Cancer following Chemotherapy Based on Molecular Profiling. Case Reports in Oncology (2012). 5(1):154-158.
Xiao et al. Effect of 5-Aza-2' deoxycytidine on immune-associated proteins in exosomes from hepatoma. World Journal of Gastroenterology (2010). 16(19):2371-2377.

(Continued)

*Primary Examiner* — Peter J Reddig
(74) *Attorney, Agent, or Firm* — Linda B. Huber; Nixon Peabody LLP

(57) ABSTRACT

The invention provides methods for isolating large oncosomes and determining cancer metastasis based on the presence of large oncosomes and contents of the large oncosomes in a subject in need thereof. Also provided herein are methods for treating cancer metastasis by specifically targeting contents of the large oncosomes.

12 Claims, 45 Drawing Sheets

(56) References Cited

OTHER PUBLICATIONS

Bhardwaj et al. Physicochemical properties of extruded and non-extruded liposomes containing the hydrophobic drug dexamethasone. International Journal of Pharmaceutics (2010). 388:181-189.
Dragovic et al. Sizing and phenotyping of cellular vesicles using Nanoparticle Tracking Analysis. Nanomedicine: Nanotechnology, Biology, and Medicine (2011). 7:780-788.
D'souza-Schorey et al. Tumor-derived microvesicles: shedding light on novel microenvironment modulators and prospective cancer biomarkers. Genes & Development (2012). 1287-1299.
Muralidharan-Chari et al. Microvesicles: mediators of extracellular communication during cancer progression. Journal of Cell Science (2010). 123:1603-1611.
Floryan et al. Intraoperative use of autologous platelet-rich and platelet-poor plasma for orthopedic surgery patients. AORN Journal (2004). 80:668-674.
Peinado et al. Melanoma exosomes educate bone marrow progenitor cells toward a pro-metastatic phenotype through MET. Nat Med (2012). 18(6):883-891.
Shao et al. Protein typing of circulating microvesicles allows real-time monitoring of gliobastoma therapy. Nat Med (2012). 18(12):1835-1840.
Response to Office Action (dated Jun. 28, 2018) of U.S. Appl. No. 13/975,059, filed Sep. 28, 2018, 11 Pages.

* cited by examiner

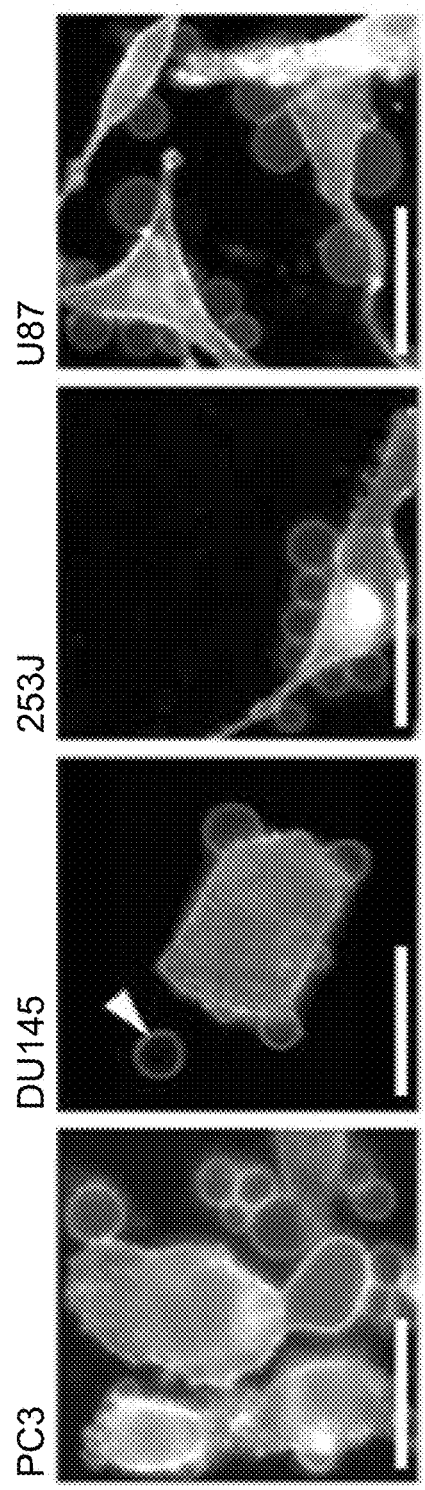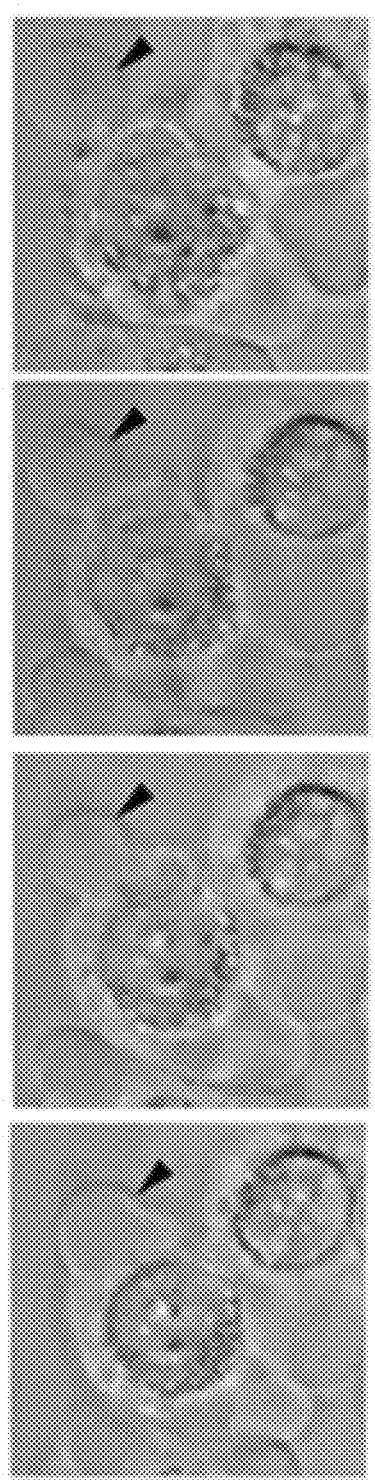

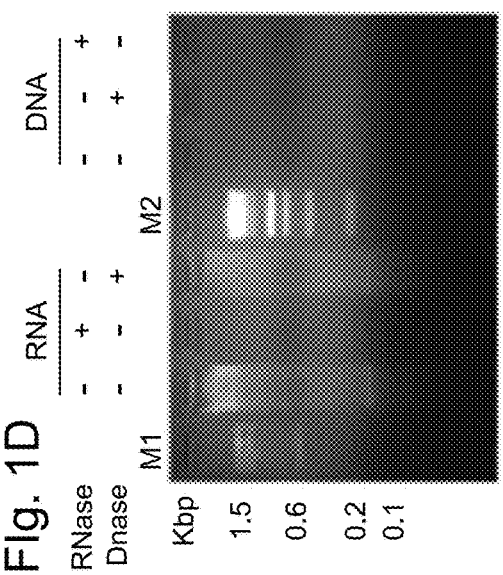
Fig. 1C
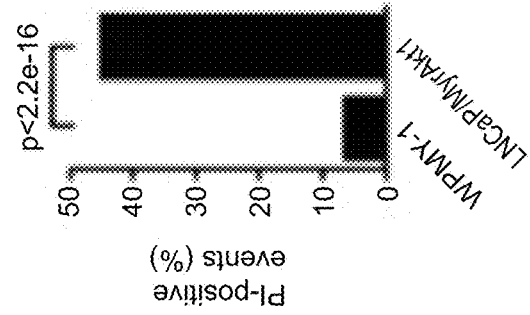
Fig. 1D
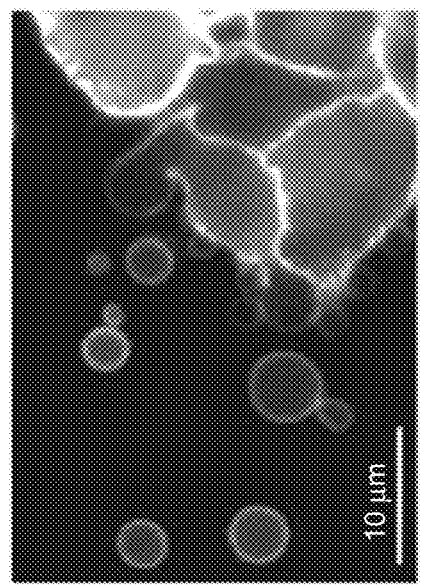
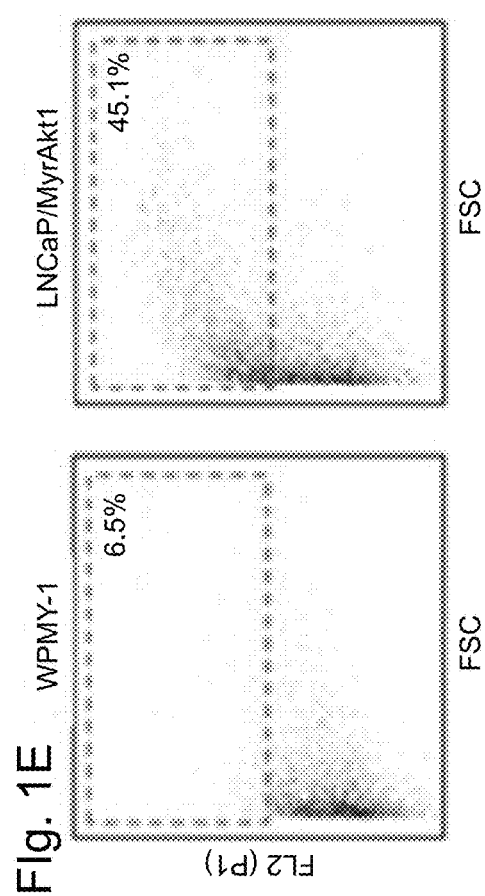
Fig. 1E

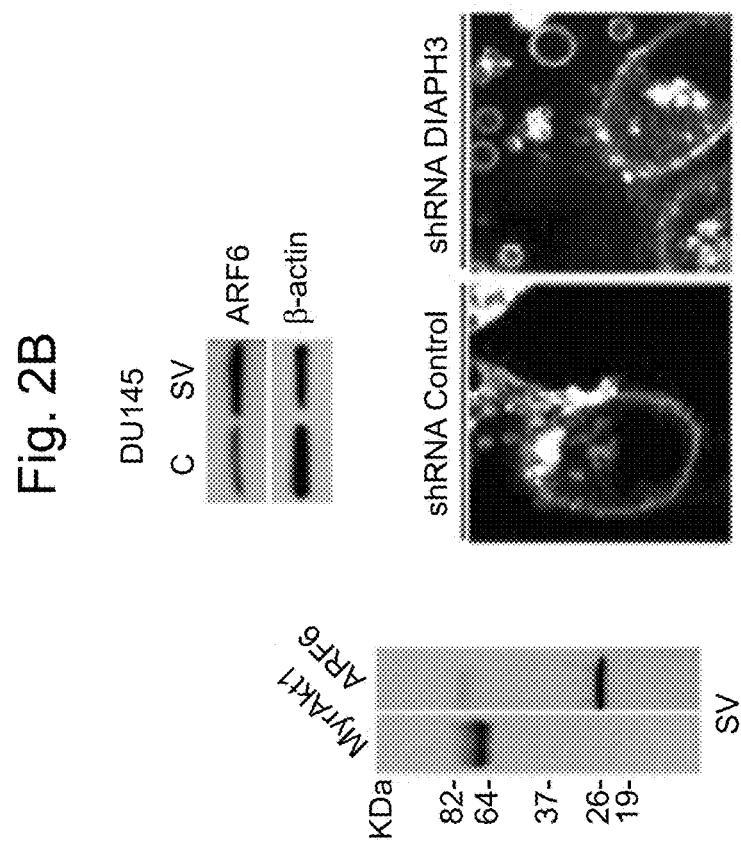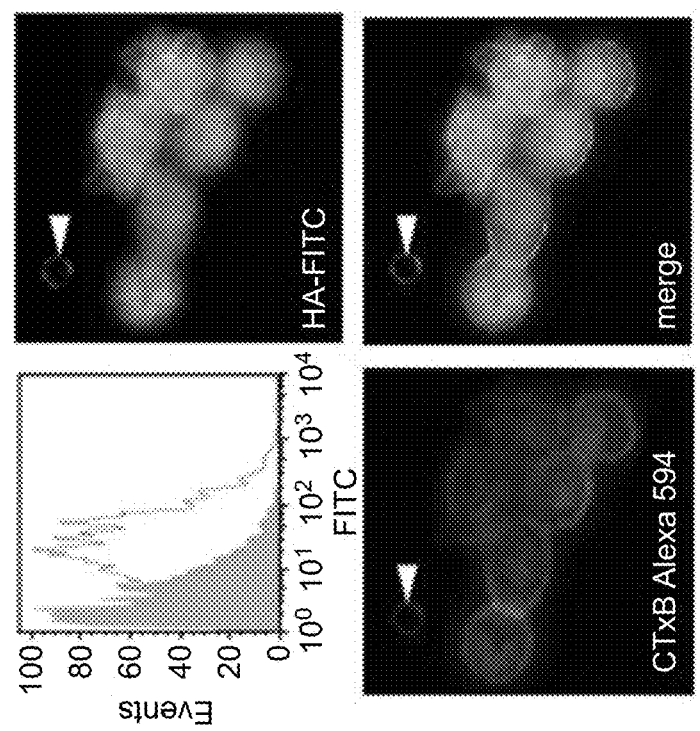

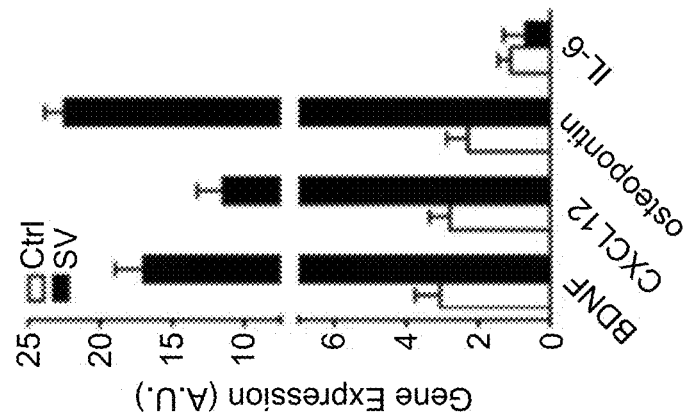
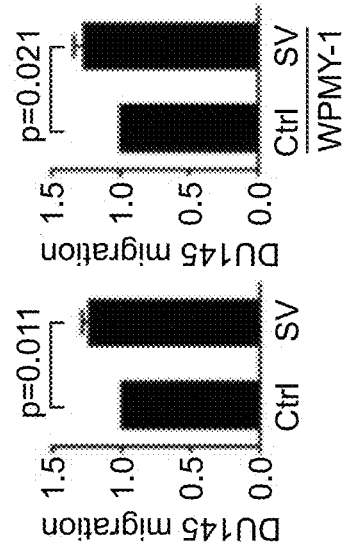
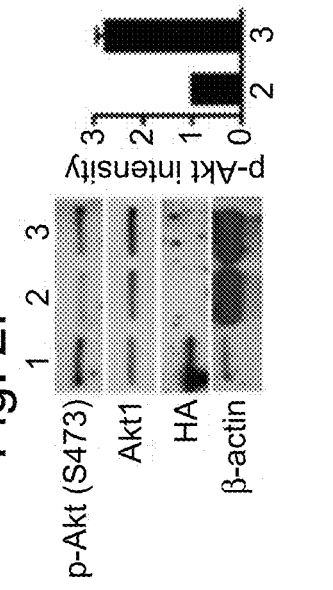
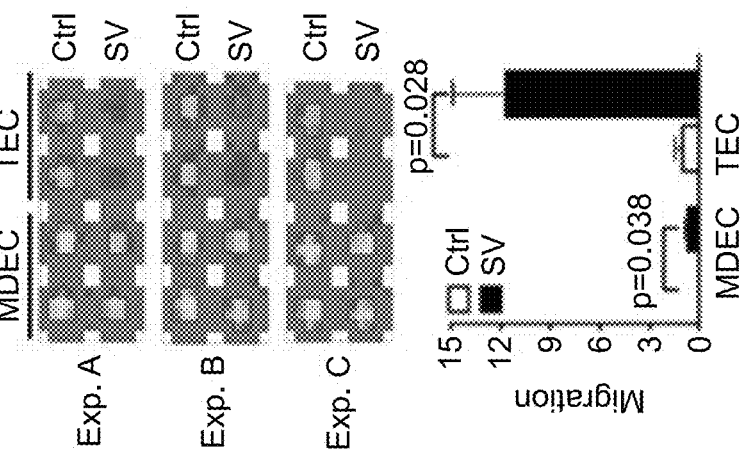

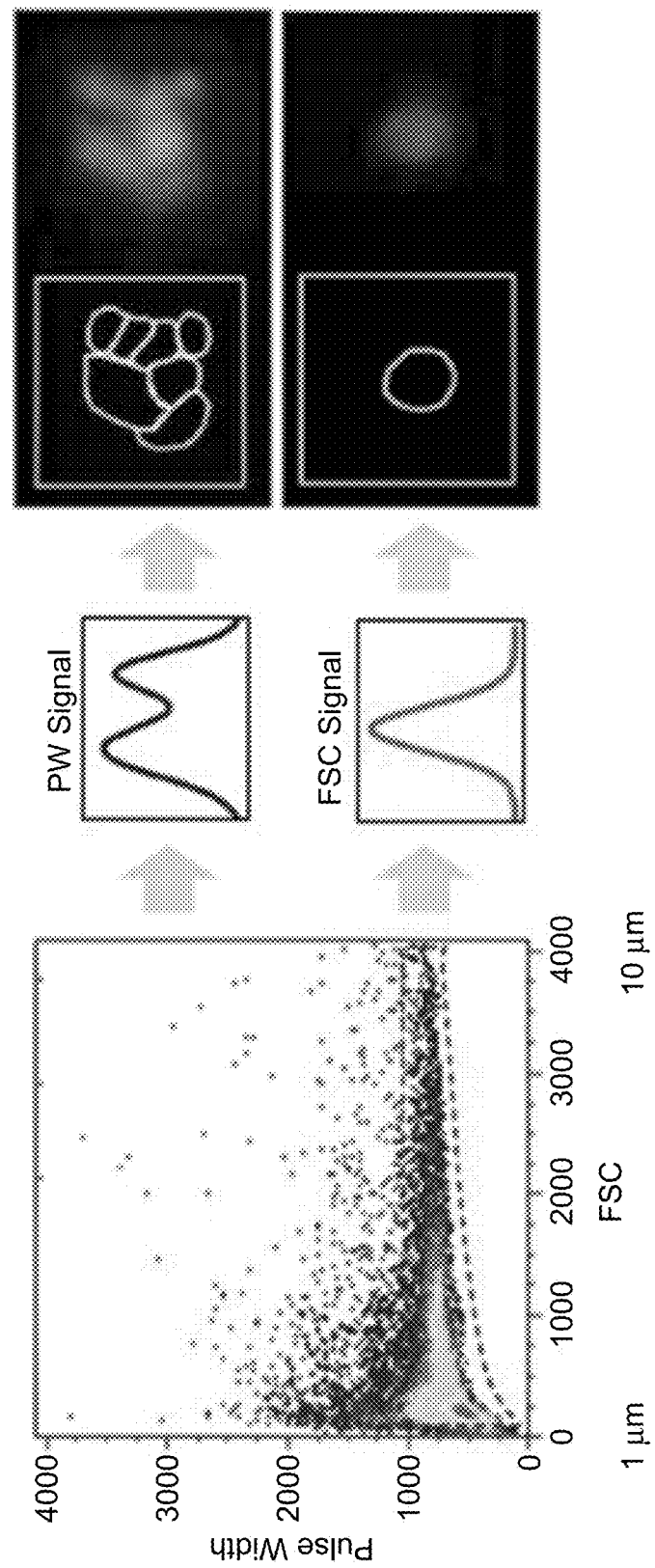

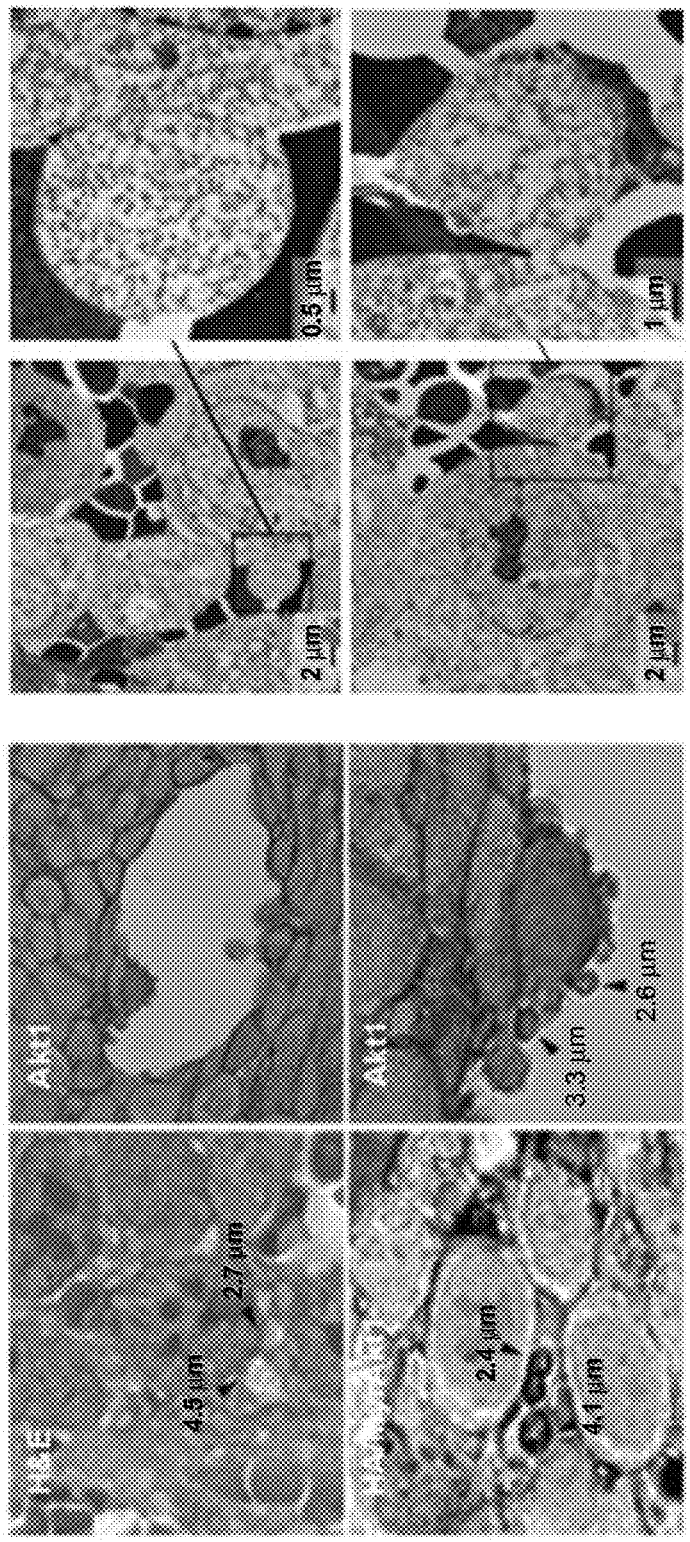

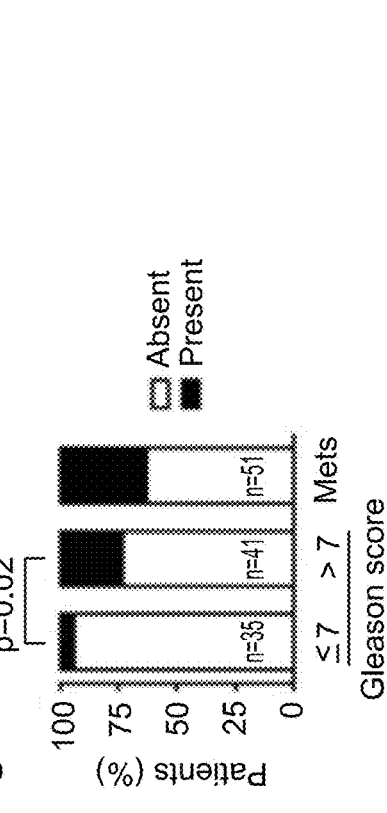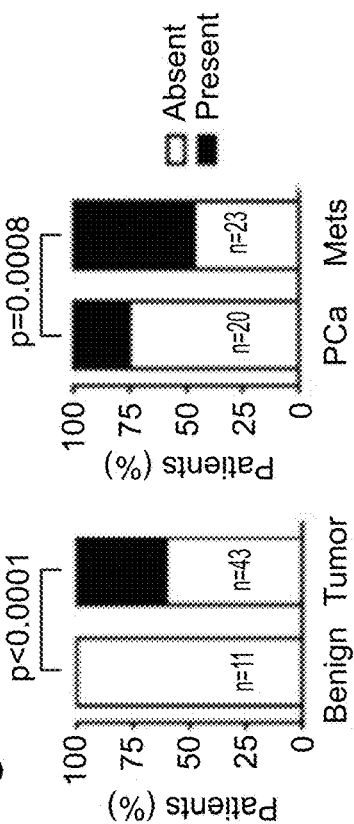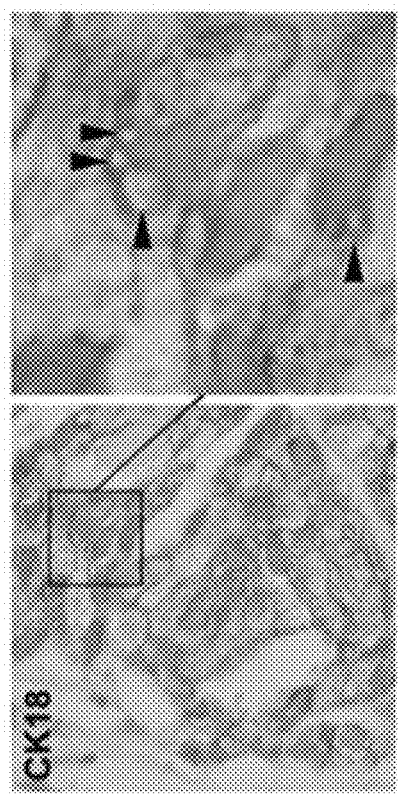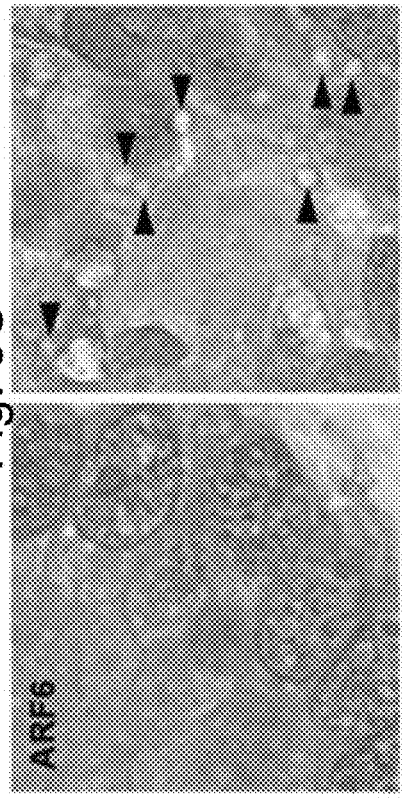

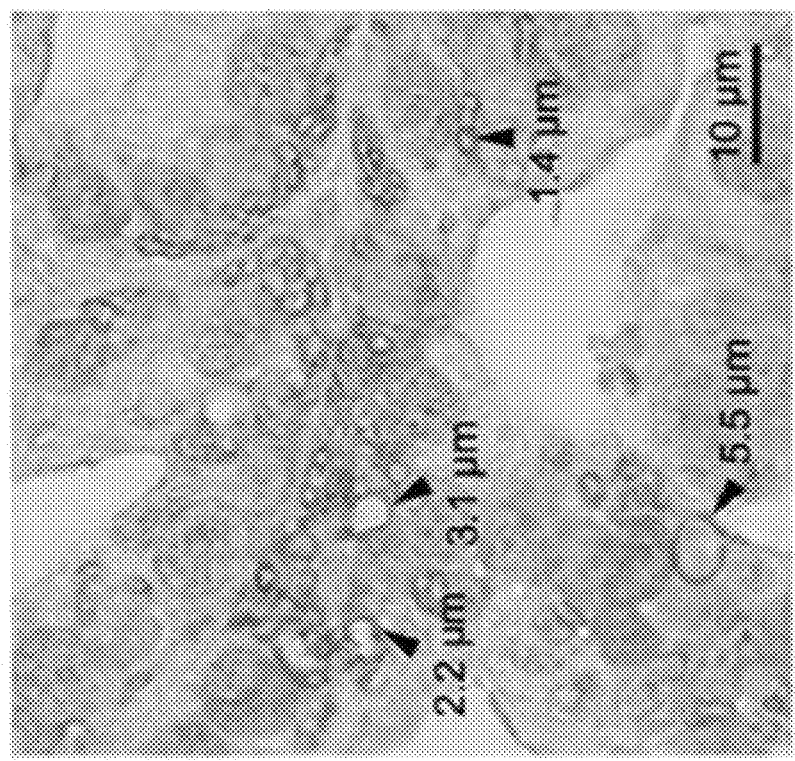
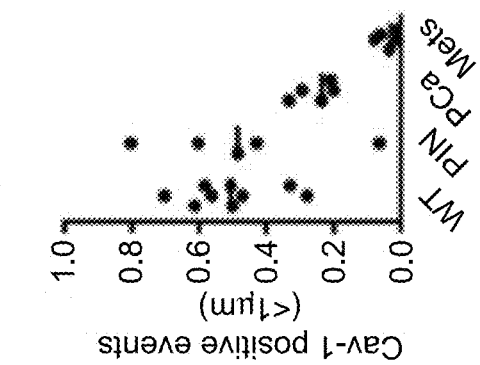
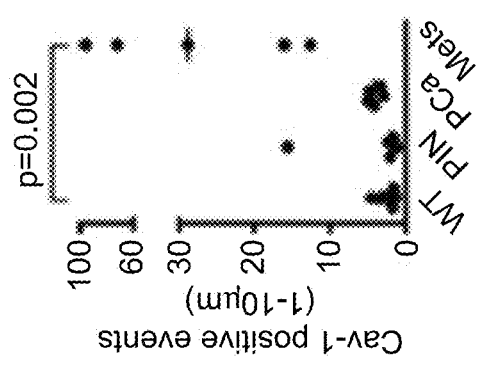

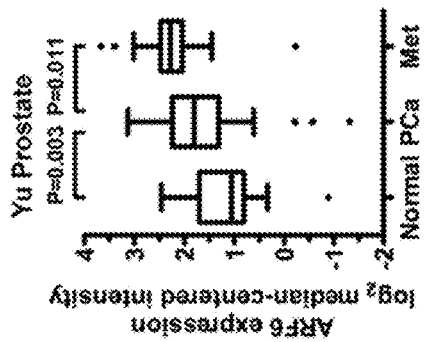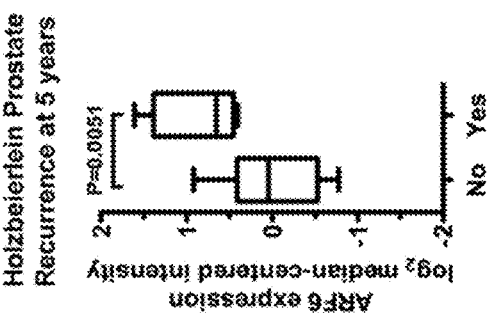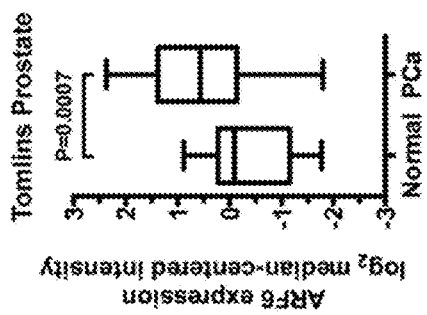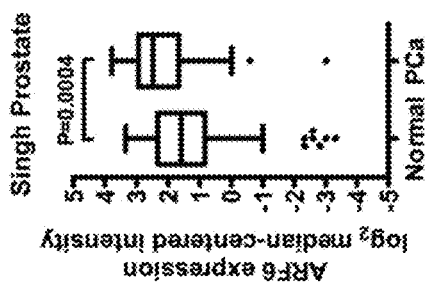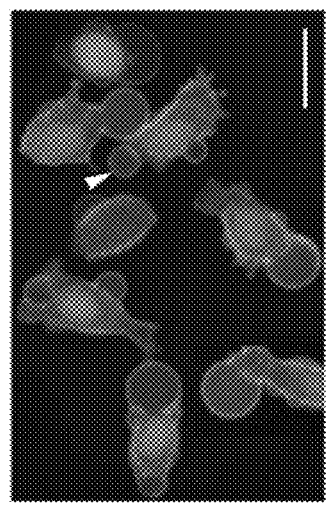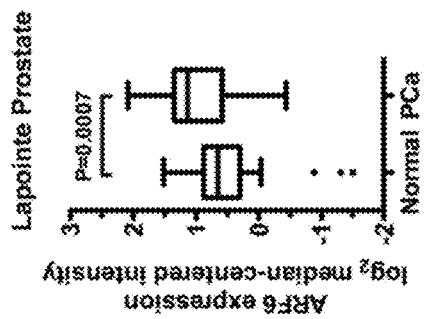

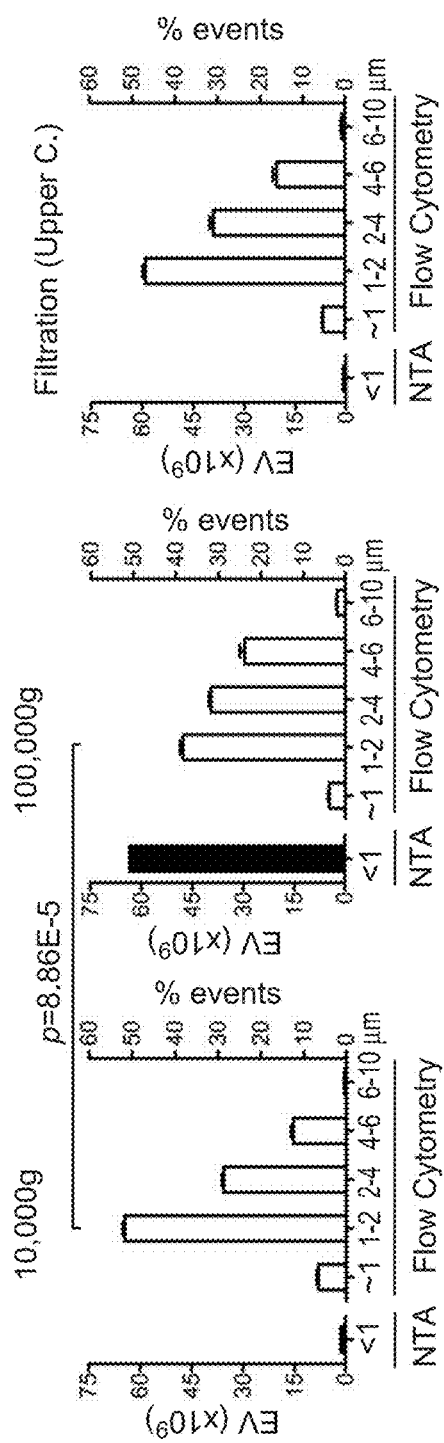
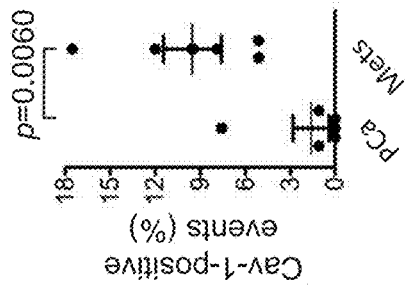
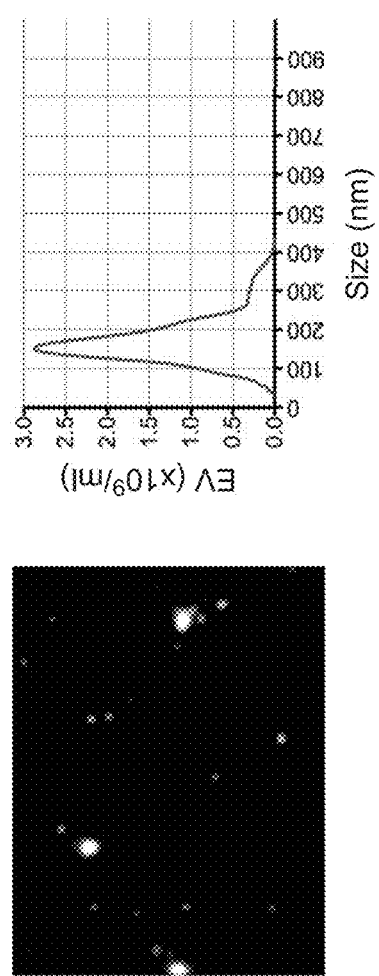

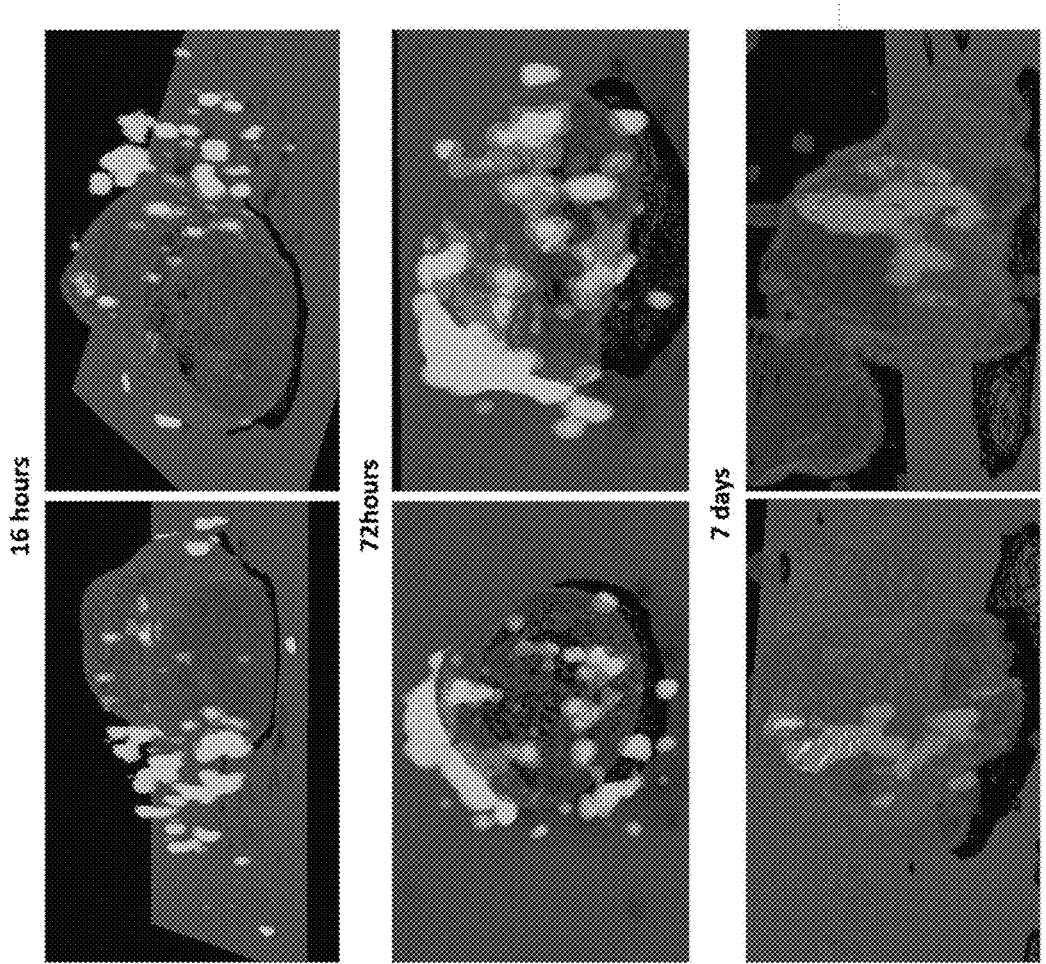

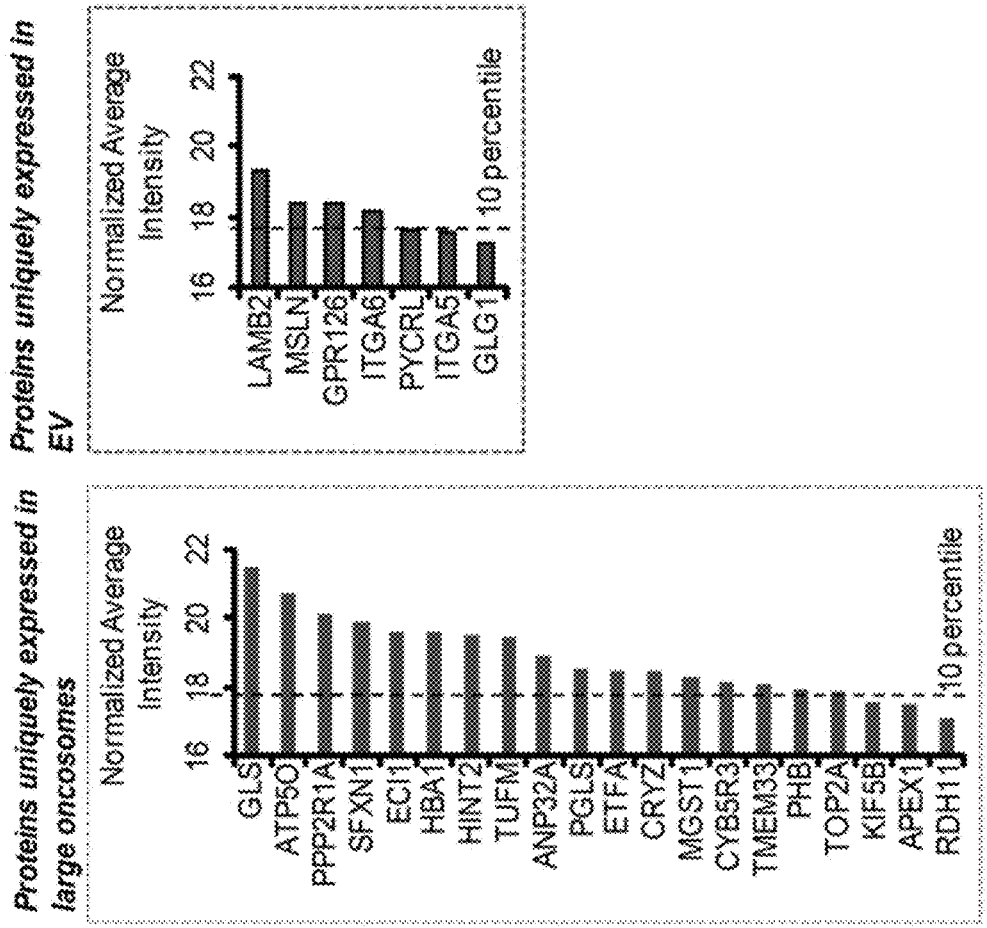
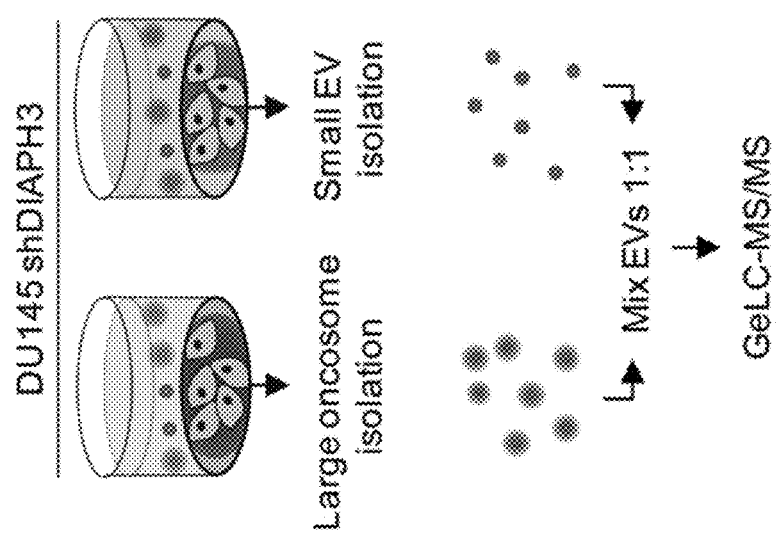
Fig. 13A
Fig. 13B

Fig. 15

| Symbol | FDR | Fold Change LO/small EV | Functions (GO, KEGG, literature mining) |
|---|---|---|---|
| HSPD1 | 0.003007 | 3.085858 | • Correlated with prostate cancer progression<br>• Anti-apoptosis<br>• Cell proliferation |
| HSPA9 | 1.6E-05 | 4.327652 | • Resistance to radiotherapy<br>• Breast cancer malignancy<br>• Liver cancer metastasis and recurrence |
| H2AFX | 0.011255 | 3.288637 | • Chromatin organization<br>• DNA repair machinery in prostate cancer |
| SLC25A6 | 8.23E-05 | 6.452446 | • Anti-apoptosis<br>• Transmembrane transport |
| MDH2 | 1.25E-05 | 4.771801 | • Resistance to docetaxel chemotherapy |
| VDAC2 | 0.000354 | 4.077545 | • Anti-apoptosis |
| ATP5B | 0.000121 | 5.940915 | • Angiogenesis<br>• Endocytosis<br>• Vesicle-mediated transport<br>• Cell migration |
| SLC25A3 | 5.06E-05 | 5.438726 | • Transmembrane transport |
| HIST2H2BF | 0.004459 | 2.646668 | • DNA packaging<br>• Chromatin organization |
| VDAC1 | 0.000216 | 5.379268 | • Anti-apoptosis |
| GPI | 0.018008 | 2.22572 | • Angiogenesis<br>• Prostate cancer progression and bone metastasis |
| STOML2 | 7.77E-05 | 4.778005 | • Metastasis<br>• Overexpressed in endometrial adenocarcinoma |

Fig. 16A

List of proteins enriched in LO.

| Protein ID | Symbol | LO/small EV | FDR |
|---|---|---|---|
| P12236 | SLC25A6 | 87.575 | < 0.001 |
| J3KPX7 | PHB2 | 73.812 | < 0.001 |
| P06576 | ATP5B | 61.432 | < 0.001 |
| Q00325 | SLC25A3 | 43.373 | < 0.001 |
| P21796 | VDAC1 | 41.622 | < 0.001 |
| P00505 | GOT2 | 29.161 | < 0.001 |
| Q9UJZ1 | STOML2 | 27.436 | < 0.001 |
| P40926 | MDH2 | 27.318 | < 0.001 |
| P38646 | HSPA9 | 20.08 | < 0.001 |
| P45880 | VDAC2 | 16.884 | < 0.001 |
| P05141 | SLC25A5 | 15.667 | < 0.001 |
| P02751-15 | FN1 | 10.702 | 0.001 |
| P34897 | SHMT2 | 9.967 | 0.003 |
| P16104 | H2AFX | 9.772 | 0.003 |
| P10809 | HSPD1 | 8.491 | 0.011 |
| Q13011 | ECH1 | 8.138 | 0.003 |
| P30048 | PRDX3 | 7.905 | 0.008 |
| Q02978 | SLC25A11 | 7.786 | 0.008 |
| P52272 | HNRNPM | 6.915 | 0.008 |
| B4DR52 | HIST2H2BF | 6.262 | 0.01 |
| Q9H3N1 | TMX1 | 5.466 | 0.004 |
| F8VTL3 | MYH10 | 5.25 | 0.018 |
| F5H7K4 | NCEH1 | 5.208 | 0.01 |
| P30084 | ECHS1 | 4.924 | 0.01 |
| Q969H8 | C19orf10 | 4.899 | 0.021 |
| P51571 | SSR4 | 4.836 | 0.021 |
| P23284 | PPIB | 4.683 | 0.021 |
| P06744-2 | GPI | 4.677 | 0.018 |

List of proteins enriched in LO (continued).

| Protein ID | Symbol | LO/small EV | FDR |
|---|---|---|---|
| Q15149 | PLEC | 4.613 | 0.024 |
| P14314 | PRKCSH | 4.604 | 0.005 |
| P20618 | PSMB1 | 4.446 | 0.024 |
| Q96AG4 | LRRC59 | 4.409 | 0.025 |
| P17174 | GOT1 | 4.171 | 0.032 |
| Q00839 | HNRNPU | 4.012 | 0.04 |
| P04843 | RPN1 | 4.007 | 0.033 |
| P05783 | KRT18 | 3.977 | 0.003 |
| P84103 | SRSF3 | 3.94 | 0.013 |
| P27797 | CALR | 3.896 | 0.031 |
| P30101 | PDIA3 | 3.89 | 0.038 |
| P62805 | HIST1H4A | 3.865 | 0.014 |
| P06748 | NPM1 | 3.839 | 0.038 |
| P28074 | PSMB5 | 3.718 | 0.03 |
| P07237 | P4HB | 3.708 | 0.049 |
| P13667 | PDIA4 | 3.444 | 0.046 |
| P49720 | PSMB3 | 3.43 | 0.041 |
| P42704 | LRPPRC | 3.414 | 0.048 |
| P11021 | HSPA5 | 3.359 | 0.014 |
| P30040 | ERP29 | 3.259 | 0.034 |
| P35579 | MYH9 | 3.256 | 0.01 |
| F5H098 | MDH1 | 3.217 | 0.006 |
| E7EPA7 | TNT | 2.963 | 0.033 |
| P07195 | LDHB | 2.851 | 0.019 |
| P04406 | GAPDH | 2.777 | 0.017 |
| B5MDF5 | RAN | 2.776 | 0.023 |
| Q15084-2 | PDIA6 | 2.528 | 0.041 |
| P46782 | RPS5 | 2.362 | 0.023 |
| P07910 | HNRNPC | 2.006 | 0.027 |

Fig. 16B

List of proteins enriched in small EV.

| Protein ID | Symbol | small EV/LO | FDR |
|---|---|---|---|
| G8JLH6 | CD9 | 10.133 | 0.01 |
| A6NMH6 | CD81 | 9.484 | 0.003 |
| P11047 | LAMC1 | 8.821 | 0.01 |
| O94985 | CLSTN1 | 8.374 | 0.003 |
| P10253 | GAA | 7.527 | 0.013 |
| Q14118 | DAG1 | 6.995 | 0.016 |
| P01137 | TGFB1 | 6.973 | 0.016 |
| P11166 | SLC2A1 | 6.867 | 0.016 |
| Q15758 | SLC1A5 | 5.784 | 0.014 |
| O75787 | ATP6AP2 | 5.523 | 0.009 |
| P10909-2 | CLU | 5.377 | 0.009 |
| P08572 | COL4A2 | 5.353 | 0.024 |
| P62879 | GNB2 | 5.346 | 0.011 |
| P26006 | ITGA3 | 5.326 | 0.012 |
| J3KN08 | MATN2 | 5.215 | 0.024 |
| P19021-5 | PAM | 5.107 | 0.025 |
| P27105 | STOM | 5.047 | 0.025 |
| O00468 | AGRN | 4.904 | 0.05 |
| P06756 | ITGAV | 4.748 | 0.026 |
| Q08431 | MFGE8 | 4.693 | 0.029 |
| P18065 | IGFBP2 | 4.692 | 0.012 |

List of proteins enriched in small EV (continued).

| Protein ID | Symbol | small EV/LO | FDR |
|---|---|---|---|
| P35052 | GPC1 | 4.626 | 0.029 |
| Q13641 | TPBG | 4.588 | 0.03 |
| P31431 | SDC4 | 4.55 | 0.032 |
| P16070 | CD44 | 4.465 | 0.046 |
| P05362 | ICAM1 | 4.449 | 0.034 |
| Q9Y4K0 | LOXL2 | 4.354 | 0.004 |
| P62873 | GNB1 | 4.26 | 0.038 |
| I3NI00 | BSG | 4.249 | 0.001 |
| O00159 | MYO1C | 4.205 | 0.04 |
| B7Z5Z2 | RRAS2 | 4.198 | 0.041 |
| J3KNY4 | CTSA | 4.151 | 0.003 |
| P07996 | THBS1 | 4.123 | 0.018 |
| Q9NS15 | LTBP3 | 4.068 | 0.03 |
| Q92820 | GGH | 4.043 | 0.044 |
| P00749 | PLAU | 3.955 | 0.047 |
| O43854 | EDIL3 | 3.886 | 0.002 |
| P21589 | NT5E | 3.87 | 0.048 |
| P05067 | APP | 3.853 | 0.002 |
| P16035 | TIMP2 | 3.508 | 0.023 |
| Q9UBV8 | PEF1 | 3.354 | 0.01 |
| P07339 | CTSD | 3.12 | 0.037 |
| F5H3A1 | ATP1A1 | 3.106 | 0.026 |
| G8JLA8 | TGFBI | 3.008 | 0.045 |

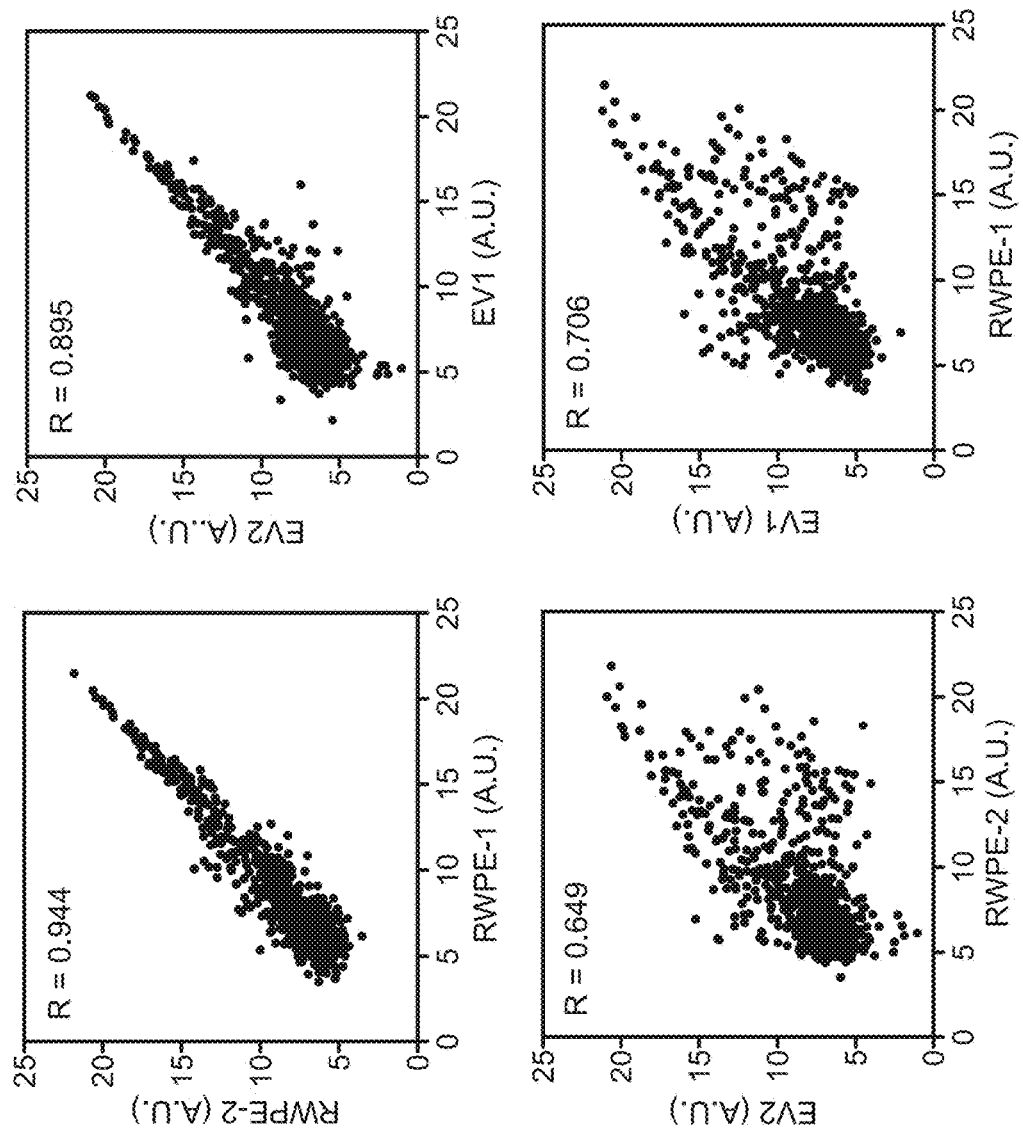

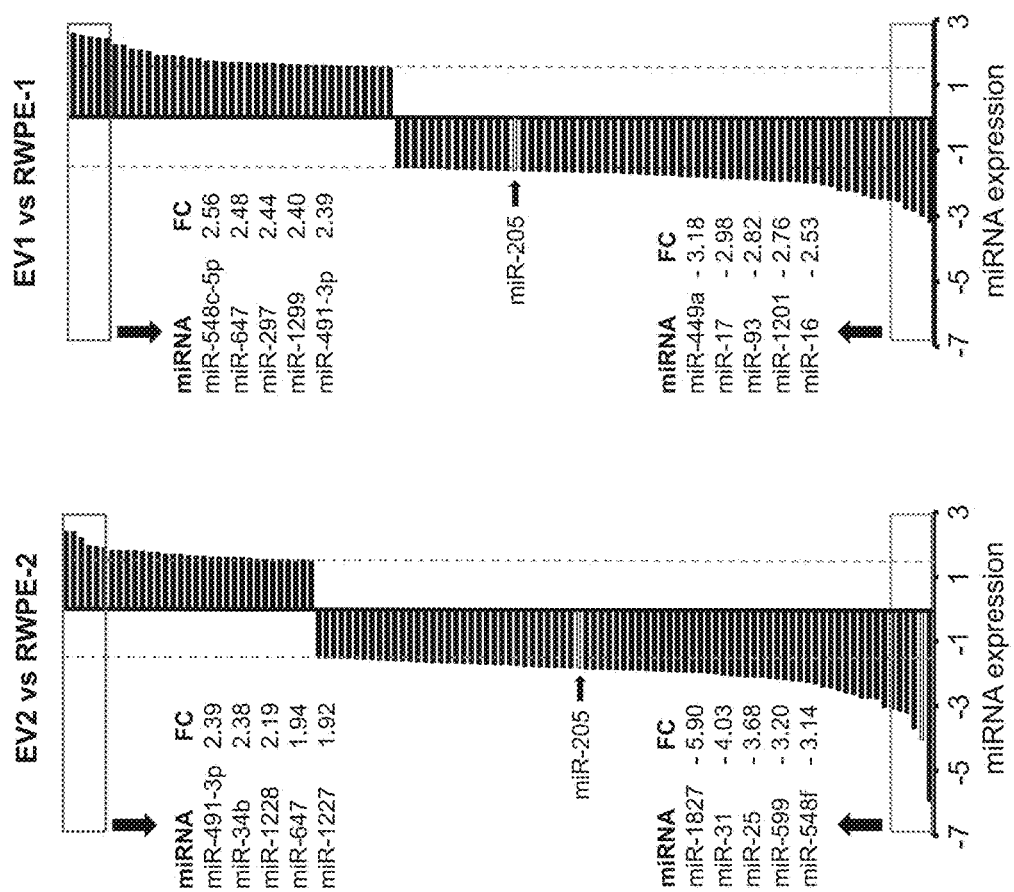

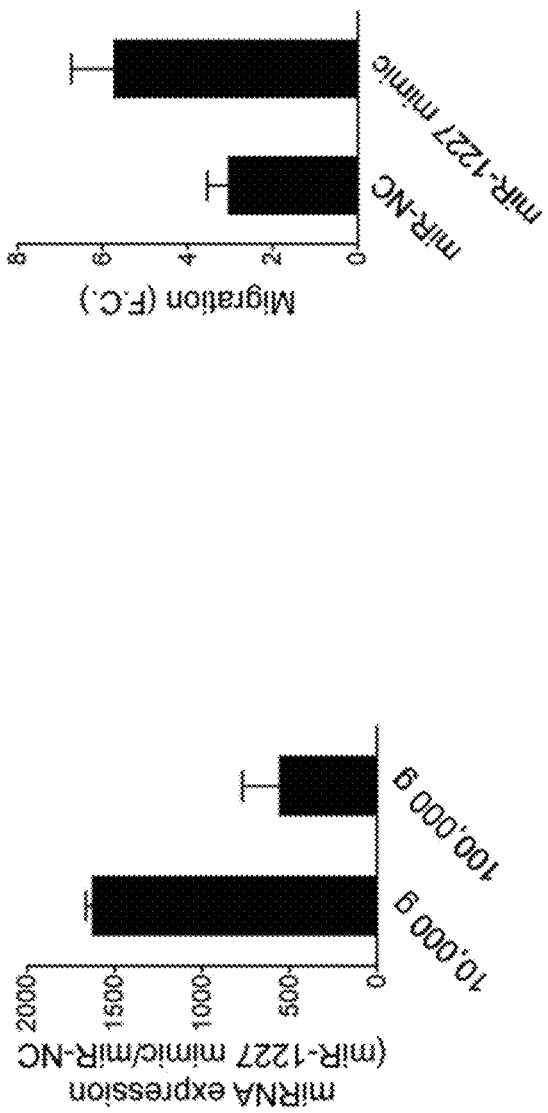

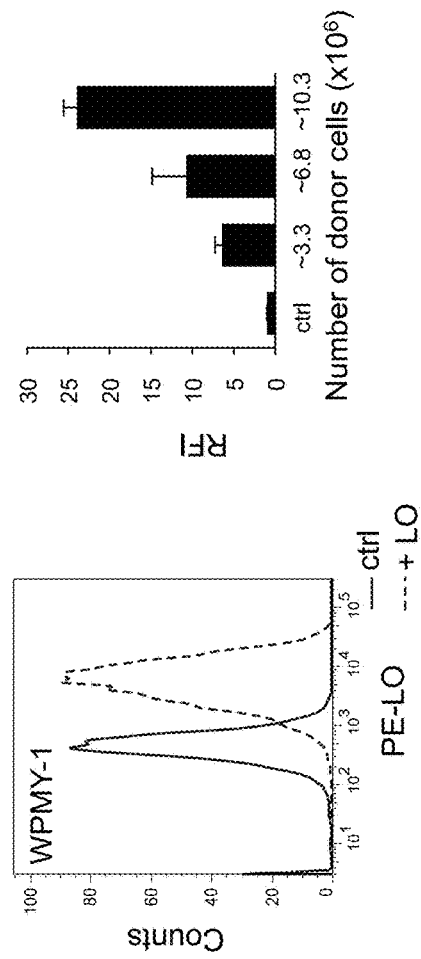
Fig. 23A
Fig. 23B
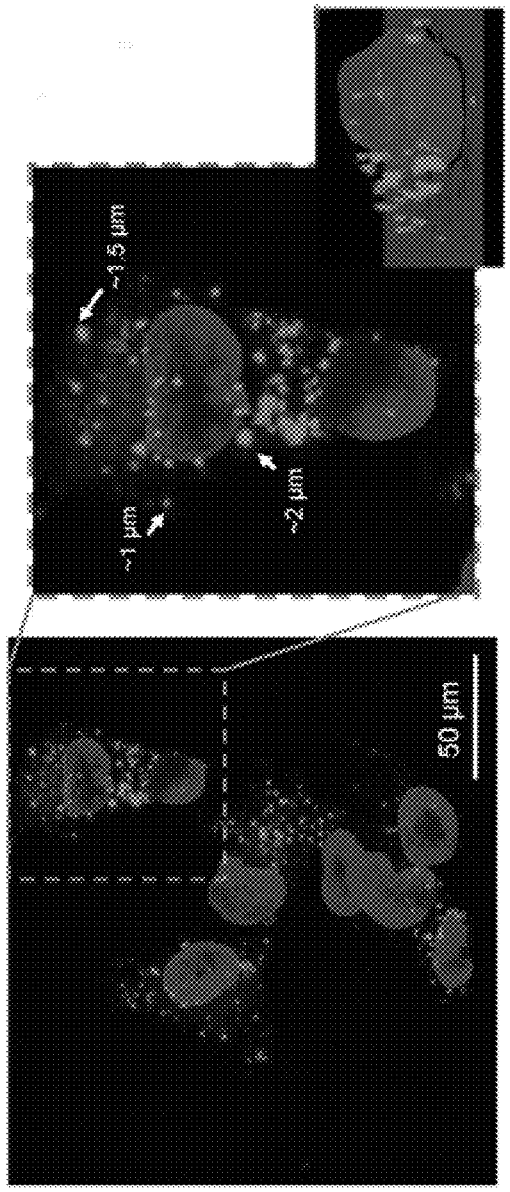
Fig. 23C

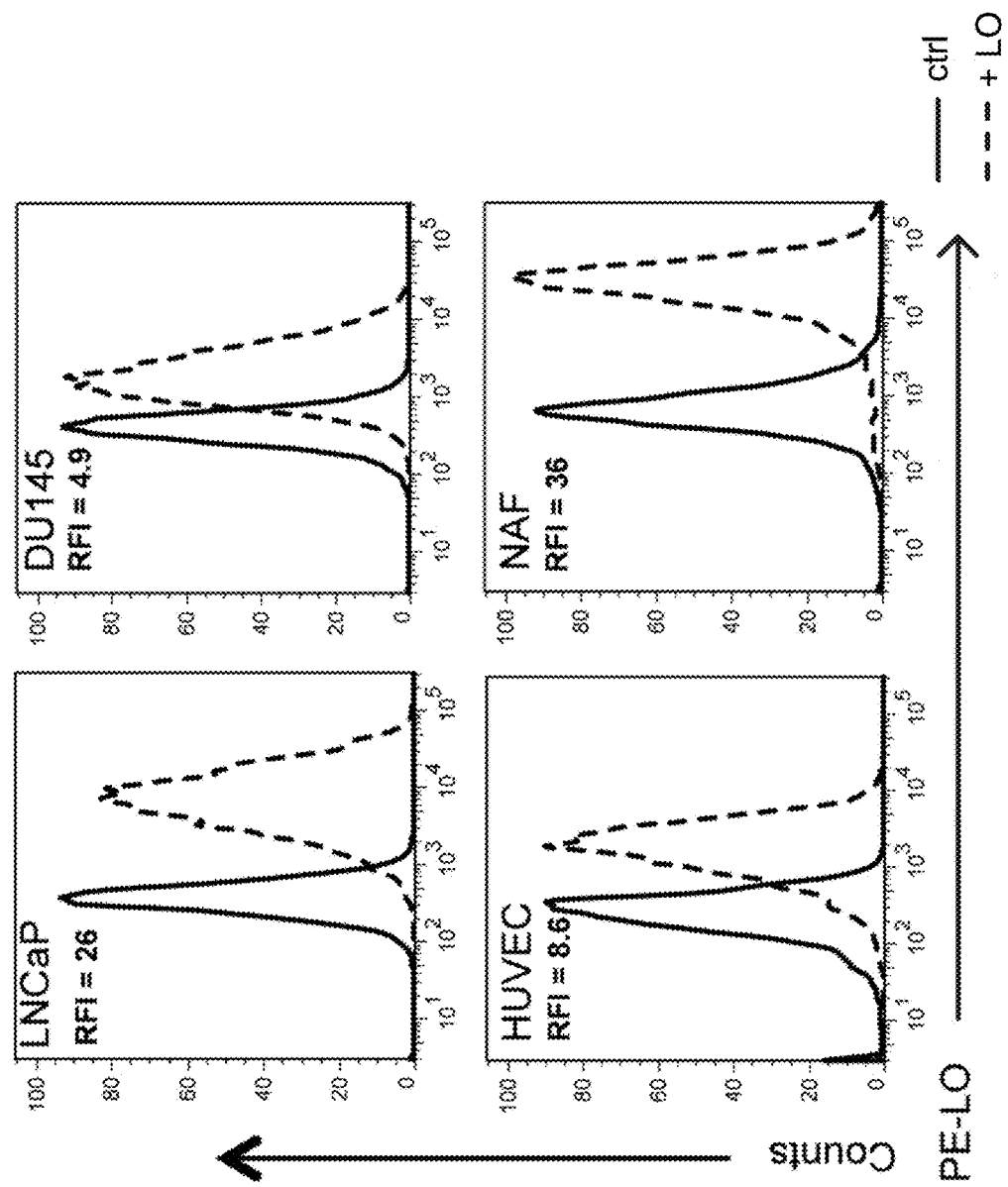

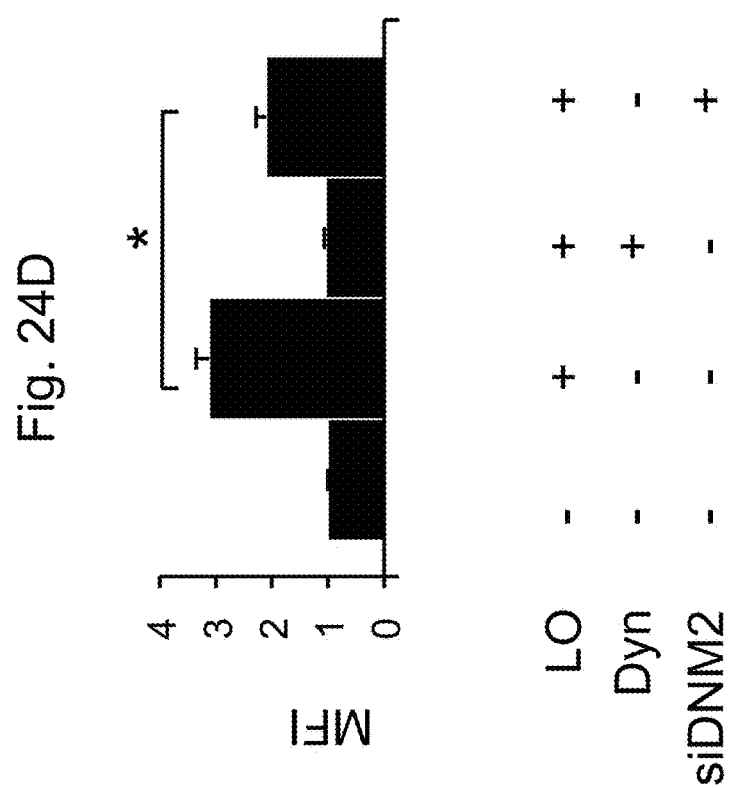

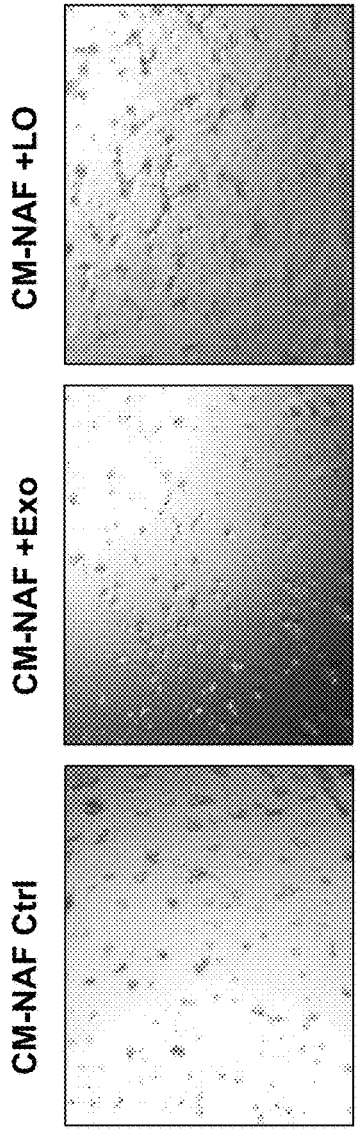
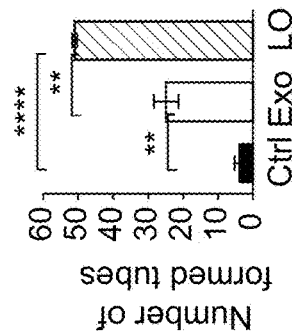
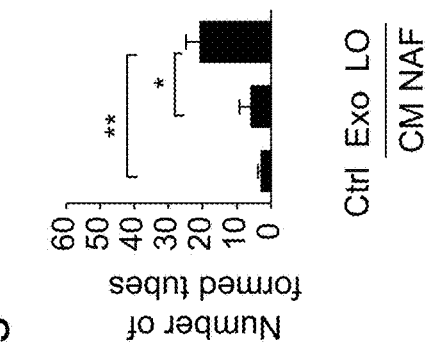
Fig. 27A
Fig. 27B

METHODS FOR DETECTING AND TREATING CANCER METASTASIS

CROSS-REFERENCE TO RELATED APPLICATIONS

This application is a continuation-in-part of International Application No. PCT/US2014/034245, filed Apr. 4, 2014, which designated the U.S. and that International Application was published under PCT Article 21(2) in English, which claims priority under 35 U.S.C. § 119(e) to U.S. provisional patent application Nos. 61/812,212, filed Apr. 15, 2013, and 61/935,269, filed Feb. 3, 2014.

STATEMENT REGARDING FEDERALLY SPONSORED RESEARCH OR DEVELOPMENT

This invention was made with government support under Grant Nos. CA131472, CA131471 and CA143777 awarded by the National Institutes of Health. The government has certain rights in the invention.

FIELD OF INVENTION

The invention is in the field of cancer biology. Provided herein are methods for detecting cancer metastasis and treating cancer.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Cancer metastases may result from cancer cells growing directly into the tissue surrounding the tumor, cancer cells traveling through the blood stream to distant locations and/or cancer cells traveling through the lymphatic system to nearby or distant lymph nodes. There is no single test for detecting tumor metastasis in general. Routine blood tests detecting specific markers may indicate metastasis but the blood tests are often normal in subjects with advanced forms of cancer. Existing imaging techniques have their limitations as well and are expensive, time consuming. There is a need in the art for tests simple blood to detect cancer metastasis.

Herein, inventors show that cancer cells shed large oncosomes. Presence of large oncosomes or an increase in the number of large oncosomes in a sample obtained from a subject that has or had cancer may be indicative of tumor metastases. The large oncosomes include proteins and nucleic acids (such as DNA, micro RNA) that are either enriched in large oncosomes compared to smaller microvesicles or that are uniquely expressed in large oncosomes compared to smaller microvesicles.

SUMMARY OF THE INVENTION

The present invention is based on the discovery that cancer cells shed microvesicles such as large oncosomes which contain molecular material such as nucleic acids, proteins and lipids. The large oncosomes may be detected without labeling the isolated large oncosomes or may be detected by labeling the molecular content of the large oncosomes.

The invention provides methods for isolating large oncosomes from a sample obtained from a subject. The method includes obtaining a sample (for example, a blood sample) from the subject, obtaining platelet-poor plasma from the sample, eliminating cells and debris from the platelet-poor plasma (for example, by centrifugation), filtering the platelet-poor plasma to separate large oncosomes from other microvesicles and collecting the large oncosomes, so as to isolate large oncosomes from the sample obtained from the subject.

The invention also provides methods for identifying large oncosomes in a tissue sample. The method includes providing a tissue sample from the subject, fixing and embedding the tissue (for example, formalin fixing and paraffin embedding tissue) and staining the tissue sample, wherein large oncosomes are identified as large membrane sacs attached to and surrounding the cells.

The invention further provides methods for determining the likelihood of cancer metastasis in a subject in need thereof. The method includes providing a sample from a subject that has or had cancer and detecting large oncosomes in the sample by the methods described herein. A presence and/or an increase in the number of large oncosomes in the sample from the subject relative to the number of large oncosomes in a reference sample is indicative of increased likelihood cancer metastasis in the subject. In some embodiments, an increase in the numbers of large oncosomes and/or the presence of specific proteins and/or enrichment of specific proteins in the large oncosomes relative to the reference sample is indicative of increased likelihood of cancer metastasis. In some embodiments, an increase in the number of large oncosomes and/or the presence of specific micro RNAs in the large oncosomes and/or enrichment of specific micro RNAs in the large oncosomes is indicative of increased likelihood of cancer metastasis in the subject.

Also provided are methods for treating cancer in a subject in need thereof. The methods include providing a biological sample from a subject, detecting large oncosomes by the methods described herein, determining if there is increased likelihood of cancer metastasis in the subject by the methods described herein and prescribing a therapy if the subject has increased likelihood of cancer metastasis.

In some embodiments, the subject has cancer. In some embodiments, the subject had cancer at some point in the subject's lifetime. In various embodiments, the subject's cancer is in remission, is re-current or is non-recurrent.

Also provided herein are methods for treating, preventing and/or reducing the severity of cancer metastasis in a subject in need thereof comprising providing one or more kinase inhibitor (for example, to target Akt kinase in large oncsomes) and administering an effective amount of the kinase inhibitor to the subject so as to treat, prevent and/or reduce the severity of cancer metastasis in the subject.

BRIEF DESCRIPTION OF FIGURES

FIG. 1A to FIG. 1H depict, in accordance with an embodiment of the invention the characterization and detection of shed tumor cell-derived vesicles. FIG. 1A shows prostate cancer (PC3, DU145), bladder cancer (253J), and glioblastoma (U87) cell lines stained with FITC-Cholera Toxin B (CTxB) and imaged by confocal microscopy (scale bar: 10 µm). FIG. 1B shows CTxB-labeled DU145 cells showing large, bulbous membrane protrusions, and several large vesicles released into the surrounding environment. FIG. 1C shows nucleic acid extracted from vesicles shed from LNCaP/MyrAkt1 cells. Total RNA/DNA was treated with RNase A or DNase 1 and samples electrophoresed through 2% agarose. FIG. 1D shows FACS analysis of vesicles, isolated from the medium of WPMY-1 and LNCaP/MyrAkt1 cells treated with EGF (50 ng/ml), fixed, permeabilized, and stained with PI. The dot plots depict FSC and FL2 (PI). The dotted lines surround PI-positive events, graphed on the right; $p<2.2e-16$. FIG. 1E left panel shows photomicrograph of FITC-labeled gelatin matrix loaded with a biochemical preparation of vesicles shed from LNCaP/MyrAkt1 cells (40×), showing large zones of proteolytic clearance. Trypsin was used as a positive control; a general protease inhibitor and vehicle served as negative controls. FIG. 1E right panel shows shed vesicles (SV) were analyzed via gelatin zymography (substrate gel electrophoresis), showing active MMP-9 and MMP-2. FIG. 1F left shows LNCaP/MyrAkt1 cells stained with FITC-CT×B. Note the large size of 2 membrane vesicles. FIG. 1F right shows FITC-labeled gelatin after exposure to SV. FIG. 1G CT×B-labeled membrane blebs (n=150) and gelatin degradation spots (n=135) were measured by AxioVision Rel. 4.5, and plotted graphically (mode: 3.1-4 µm). FIG. 1H shows the CT×B-labeled membrane blebs (n=150) and gelatin degradation spots (n=135) as measured by AxioVision version 4.5 (Zeiss) and plotted graphically (mode, 3.1 to 4 µm).

FIG. 2A to FIG. 2G depict, in accordance with an embodiment of the invention that large oncosomes are bioactive and can be identified by FACS. FIG. 2A shows LNCaP/MyrAkt1-derived vesicles, stained with HA-FITC-labeled antibody to detect MyrAkt1, were analyzed by FACS. Unstained vesicles were used as a negative control (grey-shaded). LNCaP/MyrAkt1 cells, stained with Alexa-594-CT×B and FITC-HA-labeled antibody to detect MyrAkt1 (40×). Arrowheads point to a shed large oncosome. FIG. 2B shows Shed vesicles (SV) and/or cell lysates from LNCaP/MyrAkt1 and DU145 cells were blotted with the indicated antibodies. The micrographs show DU145 shRNA control and DU145 DIAPH3-silenced (shRNA) cells stained with CT×B, revealing large oncosomes produced by DIAPH3 silencing. FIG. 2C shows mouse dermal endothelial cell (MDEC) and tumor endothelial cell (TEC) migration induced by incubation with LNCaP/MyrAkt1-derived vesicles. The image depicts a heat map of a 24-well plate showing an increase in CellTracker fluorescence (red) from migrated cells, in response to treatment with LNCaP/MyrAkt1 vesicles or vehicle. Experiments were performed in technical duplicate and biological triplicates (Exp. A, B, and C). Treatment with SV increased migration rates in both cells lines significantly: $p=0.038$ and $p=0.028$, respectively. FIG. 2D shows fold change in CellTracker fluorescence of DU145 incubated with SV or vehicle; SV induced significantly higher migration than vehicle in DU145 prostate cancer cells $p=0.011$. FIG. 2E shows fold change in CellTracker fluorescence of DU145 cells migrating in response to WPMY-1 stromal cells as attractant. WPMY-1 cells were incubated with SV or vehicle, and DU145 cell migration toward the stromal cells monitored as in (D) $p=0.021$. FIG. 2F shows that protein extracts from SV (lane 1), cells (lane 2) and cells+SV (lane 3) were blotted with the indicated antibodies. Lane 1: Protein extracts from LNCaP/MyrAkt1-derived SV; Lane 2: Protein extracts from WPMY-1 cells before exposure to SV; Lane 3: Protein extracts from WPMY-1 cells after exposure to LNCaP/MyrAkt1-derived SV. FIG. 2G shows that wild type mouse prostate fibroblasts were incubated with SV and analyzed by qRT-PCR (RT2 profiler PCR array (Qiagen)) for BDNF, CXCL12, osteopontin, and IL-6 mRNA levels. Exposure to SV resulted in a significant upregulation of these pro-metastatic factors in comparison to vehicle (Ctrl). Changes are shown as relative units of gene expression in comparison with a pool of 5 housekeeping genes.

FIG. 3A to FIG. 3B depict, in accordance with an embodiment of the invention the analysis of shed vesicles and detection of large oncosomes by FACS and microscopy. FIG. 3A shows purified vesicles derived from LNCaP/MyrAkt1 cells, stained with a FITC-conjugated HA antibody, were plotted by setting FSC vs. PW signal on a linear scale (left panel). A schematic representation of two signal pulses from the flow cytometer detector, corresponding to single particles (bottom) and doublet particles (top) is shown in the right panels. Gated single events (within the dotted line on the left panel) were visualized at the microscope and considered for further analysis. Signal pulses generated from aggregates (outside of the dotted line) were excluded. FIG. 3B shows fluorescence and electron micrographs of MyrAkt1-positive particles sorted using size beads smaller and larger than 1 µm. The arrowhead highlights the lipid bilayer structure of the vesicle-encapsulating membrane.

FIG. 4A to FIG. 4H depict, in accordance with an embodiment of the invention the identification of large oncosomes in vivo. FIG. 4A shows tumor growth and tumor take in LNCaP/MyrAkt1 and LNCaP/LacZ xenografts (growth, $p<0.01$); (sc sites free of tumor, $p=0.01$). FIG. 4B shows Akt1 immunostaining of paraffin sections of the indicated xenografts. Note the prominent Akt membrane staining in the MyrAkt1 tumors, in contrast to its diffuse cytosolic staining in the LacZ tumor sections. FIG. 4C shows FACS analysis of 1-10 µm MyrAkt1-positive vesicles purified from the plasma of mice carrying LNCaP/MyrAkt1 and LNCaP/LacZ xenografts. The dot plot depicts FSC and FL1 (MyrAkt1), and the dotted lines indicate positive events. FIG. 4D shows quantitative evaluation of MyrAkt1-positive events. A cutoff corresponding to the 99th percentile of vesicles isolated from the plasma of mice with LNCaP/LacZ tumors was chosen to segregate negative and positive events. FIG. 4E shows in mice with LNCaP/MyrAkt1 tumors, the percentage of MyrAkt1-positive vesicles correlated with tumor weight (p-value: 0.007). FIG. 4F shows mouse dermal endothelial cells (MDEC) exhibited increased migration when exposed to oncosomes in comparison to vehicle. In the left panel, the vesicles were isolated from the plasma of mice with MyrAkt1 tumors. In the right panel, vesicles were derived from the medium of LNCaP/MyrAkt1 cells. FIG. 4G shows tumor sections of LNCaP/MyrAkt1 xenografts stained with hematoxylin and eosin (H&E); arrowheads point to large vesicles, similar in appearance to large oncosomes. Sections were also immunostained with an Akt1 antibody, which identified Akt1 at the plasma membrane and allowed visualization of large vesicles. FIG. 4H Tumor sections of LNCaP/MyrAkt1 xenografts imaged by TEM. Membrane blebs protruding from tumor cells near blood vessels are highlighted.

FIG. 5A to FIG. 5D depict, in accordance with an embodiment of the invention the large oncosome-like vesicles in metastatic prostate cancer. FIG. 5A shows representative paraffin section of human core biopsies of patients with prostate cancer (Gleason score 4+3) immunostained with CK18 antibody. Arrowheads point to structures resembling large oncosomes. FIG. 5B shows quantitative analysis of the distribution of ARF6 positive large oncosome-like vesicles among the diagnostic categories, showing vesicles are significantly more abundant in Gleason score >7 than in Gleason score ≤7 (p=0.020) and in Mets than in organ-confined tumors (PCa) (p=0.001). FIG. 5C shows representative sections of an additional prostate cancer TMA stained with ARF6 showing absence (left) and presence (right) of large oncosome-like vesicles in the right panel (arrowheads). FIG. 5D shows the presence of structures resembling large oncosomes significantly discriminates between normal and tumor samples (p<0.0001), and between organ confined disease and metastasis (p=0.0008).

FIG. 6A to FIG. 6E depict, in accordance with an embodiment of the invention the large oncosome-like structures containing Cav-1 identify aggressive prostate cancer. FIG. 6A shows FACS analysis of 1-10 μm Cav-1 positive vesicles purified from the plasma of TRAMP mice (n=15) and non-transgenic littermates (WT) (n=10), plotted in a FSC histogram, and analyzed with respect to the diagnostic categories. FIG. 6B shows large oncosome-like structures, isolated from the plasma of TRAMP and WT mice, were analyzed by western blot. FIG. 6C shows that the abundance of Cav-1-positive large oncosome-like structures (1-10 μm) was significantly increased in tumor-bearing mice than in controls p=0.0007, and dramatically correlated with disease progression (almost 30-fold difference between mice with organ-confined tumors vs. mice with lung metastases), p=0.0002. FIG. 6D shows that the abundance of Cav-1-positive events <1 μm did not reflect changes across the diagnostic categories. FIG. 6E shows representative paraffin section of a TRAMP metastatic tumor stained with ARF6 antibody. Arrowheads point to large oncosome-like structures.

FIG. 7A to FIG. 7G depicts in accordance with an embodiment of the invention that ARF6 is overexpressed in human prostate cancer. In FIG. 7A EGF-treated blebbing PC3 cells labeled with FITC-CTxB and propidium iodide (PI) were imaged using an Axioplan 2 microscope (scale bar: 10 μm). FIG. 7B shows 9 independent expression data sets comparing normal prostate tissue and prostate adenocarcinoma consistently show significant upregulation of ARF6 expression levels in prostate cancer. Of these, 4 studies rank ARF6 expression levels in the top fifth percentile of all upregulated genes and 3 studies rank ARF6 in the tenth percentile. FIGS. 7C-F shows box plots showing AFR6 expression levels in normal prostate, prostate adenocarcinomas and metastatic lesions of 4 representative and high-powered expression profiles. FIG. 7G shows that elevated ARF6 expression correlates with disease recurrence at 5 years.

In FIG. 8A LNCaP cells were engineered to overexpress a Cav-1/GFP fusion protein or vector only (Vo)/GFP and photographed by fluorescence microscopy (40x). In FIG. 8B whole cell lysates from LNCaP expressing Vo/GFP and Cav-1/GFP were blotted using Cav-1 antibody. In FIG. 8C whole cell lysates (C) and SV from LNCaP expressing Vo/GFP and Cav-1/GFP were blotted using the indicated antibodies. FIG. 8D shows quantitative analysis of bleb formation in LNCaP cells overexpressing Vo/GFP and Cav-1/GFP (p=0.03).

In FIG. 9A purified particles from LNCaP cells overexpressing Cav-1/GFP were stained with a Cav-1 antibody, sorted by flow cytometry, and examined by microscopy (scale bar: 10 μm). In FIG. 9B purified particles from LNCaP cells overexpressing Cav-1/ GFP (left) and DU145 cells (right), stained with α-Cav-1, were analyzed by flow cytometry. A Cy3-conjugated secondary antibody was used for detection. Unstained particles were used as a negative control (grey shaded).

FIG. 11A to FIG. 11C depict, in accordance with an embodiment of the invention a comparison between ultracentrifugation and filtration-based protocols. FIG. 11A shows comparative analysis, by flow cytometry (clear bars), of EV isolated from the medium of the glioblastoma cell line U87, using ultracentrifugation-based protocols (10,000 and 100,000 g) versus the filtration-based protocol, showing that our new method allows detection of large oncosomes in the upper chamber. The comparative analysis was also performed by Nanoparticle Tracking Analysis (NTA) using the NanoSight (black bars) showing that our new method excludes exosomes and microvesicles <1 mm. FIG. 11B shows snapshot and NTA profile of particles isolated using ultracentrifugation protocol (100,000 g). FIG. 11C shows using the new method that Cav-1 positive large oncosomes discriminate metastatic prostate cancer.

FIG. 12A to FIG. 12B depict, in accordance with an embodiment of the invention, that large oncosomes are internalized in stromal cells. In FIG. 12A the top panel shows a dose-dependent response of internalization of large oncosomes, showing increased signal with increased concentrations of large oncosomes. The bottom panel shows confocal images of sorted fibroblast positive for large oncosome internalization. FIG. 12B shows the follow up of fibroblasts that have been sorted after the treatment with large oncosomes. The cells were fixed and imaged by confocal respectively 16 h, 72 h and 7 days after sorting. 3D reconstruction was performed, as shown, to understand the position of large oncosomes once they enter into the cell.

FIG. 13A to FIG. 13C depict, in accordance with an embodiment of the invention, the identification of common and unique proteins in large oncosomes and smaller EV. FIG. 13A shows schematic representation of DIAPH3-silenced DU145 cells, double-labeled with light and heavy medium before undergoing isolation of large oncosomes and smaller EV respectively, for SILAC analysis. FIG. 13B shows a list of proteins specific for large oncosomes and small EV. FIG. 13C shows gene ontology analysis showing enrichment of the indicated biological processes for differentially expressed proteins (DEPs) in large oncosomes and smaller EV.

FIG. 14A shows that Fibronectin 1 (FN1) is significantly overexpressed in large oncosomes in comparison with smaller EV, in DU145 cells silenced with shDIAPH3. The control is DU145 cells, not silenced with shDIAPH3. FIG. 14B shows that CK18 is only detected in large oncosomes, whereas CD81 and CD63, commonly used markers for exosomes are significantly overexpressed in the small EV.

FIG. 15 depicts, in accordance with an embodiment of the invention, proteins that are highly enriched in large oncosomes, with a known functional role in cancer metastasis and response to the therapy.

FIG. 16A to FIG. 16B depicts, in accordance with an embodiment of the invention, a list of proteins enriched in large oncosomes and smaller EV. FIG. 16A shows a list of proteins enriched in large oncosomes. FIG. 16B shows a list of proteins enriched in small EV.

FIG. 17A to FIG. 17C depict, in accordance with an embodiment of the invention, miRNA profiling of prostate cells and derived EVs (Discovery). In FIG. 17A and FIG. 17B oncosome formation in CTxB-FITC labeled RWPE-1 and RWPE-2 cells, was quantitatively analysed in presence or absence of full medium (FM), serum free medium (SFM) and EGF. FIG. 17C shows expression levels of 847 miRNAs in cells and extracellular vesicle. Scatter plots data show the correlation between: RWPE-2 versus RWPE-1 cells (R=0.944), EV2 versus EV1 (R=0.895), EV1 versus RWPE-1 cells (R=0.706) and EV2 versus RWPE-2 cells (R=0.649). The difference between EV2 versus RWPE-2 cells and EV1 versus RWPE-1 cells indicate an active selection and secretion of miRNA into EV.

FIG. 18A to FIG. 18C depict, in accordance with an embodiment of the invention, qRT-PCR validation of the discovery experiment using the filtration method, and relative quantitation of miRNAs detected in both EV and donor cells. TaqMan qRT-PCR levels of miRNAs in EV2 versus RWPE-2 cells (FIG. 18A), and EV1 versus RWPE-1 cells (FIG. 18B). FIG. 18C shows relative quantitation of the miRNAs with at least 1.5-fold expression change (dotted lines) in EV2 versus RWPE-2 cells (left panel), and in EV1 versus RWPE-1 cells (right panel); boxes at the top show the top 5 expressed miRNAs and boxes at the bottom show the bottom 5 expressed miRNAs.

FIG. 19A to FIG. 19B depict, in accordance with an embodiment of the invention, quantitation of miR-1227. FIG. 19A shows qRT-PCR analysis using miR-1227 specific primers was performed on total miRNA isolated from large and small EVs (10 000 and 100 000 g) from RWPE-2 overexpressing miR-1227 mimic. This transient overexpression in cells results in the enrichment of the miRNA in large oncosomes but not in the small EVs. FIG. 19B shows migration of cancer associated fibroblasts was enhanced by large EVs overexpressing miR-1227.

FIG. 20A shows LO, which float to a 15% and 25% iodixanol fraction of the 10,000×g (10K) pellet are identified by the presence of CK18 and absence of CD81, while the absence of CK18 and presence of CD81 confirms the presence of exosomes (Exo) in the 15% iodixanol fraction. Both Akt1 and p-Akt1 are preferentially exported in LO vs Exo from LNCaPMyrAkt1. FIG. 20B shows that endogenous p-Akt can also be found in abundance in LO, but not Exo, from other prostate cancer cell lines.

FIG. 21A shows bar plot showing p-Akt1 levels (average) in 500 µl of plasma derived LO and Exo from 6 patients with prostate cancer. **p=0.005. FIG. 21B shows Western Blot for p-Akt1 and Akt1 in two representative patients.

FIG. 22A shows IP for HA; Western blotting for p-Akt1 shows that MyrAkt1 is exported in LO in a phosphorylated, active form. FIG. 22B shows kinase activity assay for pAkt1 and shows phosphorylation of the GSK3a/b recombinant protein (27 kDa) in 10K (LO) but not in 100K (Exo) pellet, indicating that that Akt1 is selectively active within LO. The same amount of protein was loaded. Akt1 activity is maintained in LO over time.

FIG. 23A to FIG. 23F depict in accordance with an embodiment of the invention that LO internalization differs between cells. FIG. 23A shows FACS data showing the uptake of PKH26-labeled LO by WPMY-1 cells. The histogram is representative of three biological replicates. FIG. 23B shows accumulation of PKH26-labeled LO in WPMY-1, as detected by FACS is dose dependent. The plot shows the average of three biological replicates and the rate of internalization is expressed as relative fluorescent intensity (RFI). FIG. 23C shows that WPMY-1 cells, exposed to PKH26-labeled LO, were sorted and imaged by confocal microscopy. Intact LO (1-2 µm in diameter), are internalized by recipient cells and localize in cytosol and in the perinuclear area. FIG. 23D shows that LO internalization rate varies among different cell types. The indicated cells were exposed to PKH26-labeled LO or vehicle for 1 h at 37° C., and then analyzed by FACS to quantify LO uptake. FIG. 23E shows that WPMY-1 cells exposed to PKH26-labeled LO sorted and visualized by confocal imaging. PKH26 staining co-localizes with HA staining (MyrAkt1 tag) in large oncosomes within WPMY-1 cells. FIG. 23F shows normal associated fibroblasts, NAF, exposed to PKH26-labeled LO sorted and visualized by confocal imaging.

FIG. 24A to FIG. 24D depict in accordance with an embodiment of the invention that LO internalization occurs through active endocytosis and internalization can be inhibited by Dyn. FIG. 24A shows that LO uptake was partially reduced by inhibition of PI3K activity with wortmannin (WTN) and by inhibition of actin polymerization with cytochalasin D (CYT-D). FIG. 24B shows that LO uptake was significantly reduced by dynamin inhibition with dynasore (Dyn), but not by inhibition of the a+/H+ antiporter with amiloride (AMIL). The quantitative bar-plots show the average of three biological replicates. Internalization is expressed as mean fluorescent intensity (MFI). This result suggests that LO are internalized via phagocytosis. FIG. 24C shows representative FACS histograms and fluorescence imaging of WPMY-1 cells treated with PKH26-labeled LO at 4° C. or in presence of Dyn. FIG. 24D shows Dynamin2 (DNM2) silencing in WPMY-1 cells significantly reduced LO uptake. Dyn was used as positive control. All experiments were performed in biological triplicate, *p<0.05 and **p<0.002.

FIG. 26A shows TF activation profiling array in WPMY-1 exposed to LO at indicate time points. The fold change, normalized to control, indicates increased DNA binding ability for some of the indicated TFs. FIG. 26B shows Luciferase reporter assay for c-Myc in NAF exposed to LO or Exo (20 µg/ml) for 6 h, showing that Myc activation is significantly induced by LO but not by Exo. FIG. 26C shows RT-PCR for indicated c-Myc target genes in NAF exposed to LO for 6 h and 24 h. FGF2, GLS1 and LDHA mRNA levels significantly increase after 6 h and 24 h.

FIG. 27A to FIG. 27B depict in accordance with an embodiment of the invention that LO induce a robust tube formation. FIG. 27A shows that LO induced a significantly higher tube formation than Exo in HUVECs. FIG. 27B shows that tube formation was induced in HUVECs exposed to conditioned media from NAFs treated with LO but not Exo from LNCaPMyrAkt1 for 24 h. All experiments were performed in biological triplicate, *p<0.05, p<0.002 and **p<0.000001.

FIG. 28A shows Luciferase reporter assay for c-Myc in NAF exposed to LO (20 μg/ml) in presence or absence of Dyn (20 μM). The result shows that c-Myc activation is significantly induced by LO and that the effect is reverted with Dyn treatment. FIG. 28B shows tube formation was significantly inhibited in HUVECs treated with LO (20 μg/ml) in presence of Dyn. *p<0.05.

DETAILED DESCRIPTION OF THE INVENTION

Figure 1F:
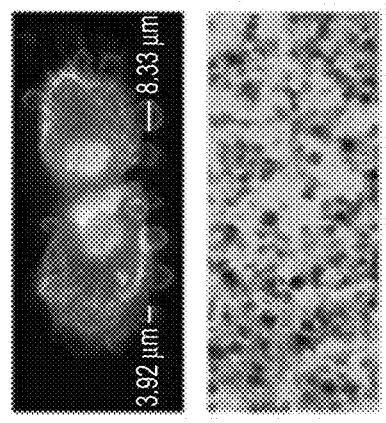

All references cited herein, including the references cited therein, are incorporated by reference in their entirety as though fully set forth. Unless defined otherwise, technical and scientific terms used herein have the same meaning as commonly understood by one of ordinary skill in the art to which this invention belongs. The practice of the present invention will employ, unless indicated specifically to the contrary, conventional methods of molecular biology and recombinant DNA techniques within the skill of the art, many of which are described below for the purpose of illustration. Such techniques are fully explained in the literature. Allen et al., *Remington: The Science and Practice of Pharmacy* 22$^{nd}$ ed., Pharmaceutical Press (Sep. 15, 2012); Hornyak et al., *Introduction to Nanoscience and Nanotechnology*, CRC Press (2008); Singleton and Sainsbury, *Dictionary of Microbiology and Molecular Biology* 3$^{rd}$ ed., revised ed., J. Wiley & Sons (New York, N.Y. 2006); Smith, *March's Advanced Organic Chemistry Reactions, Mechanisms and Structure* 7$^{th}$ ed., J. Wiley & Sons (New York, N.Y. 2013); Singleton, *Dictionary of DNA and Genome Technology* 3$^{rd}$ ed., Wiley-Blackwell (Nov. 28, 2012); and Green and Sambrook, *Molecular Cloning: A Laboratory Manual* 4th ed., Cold Spring Harbor Laboratory Press (Cold Spring Harbor, N.Y. 2012), provide one skilled in the art with a general guide to many of the terms used in the present application. For references on how to prepare antibodies, see Greenfield, *Antibodies A Laboratory Manual* 2$^{nd}$ ed., Cold Spring Harbor Press (Cold Spring Harbor N.Y., 2013); Köhler and Milstein, *Derivation of specific antibody-producing tissue culture and tumor lines by cell fusion*, Eur. J. Immunol. 1976 July, 6(7):511-9; Queen and Selick, *Humanized immunoglobulins*, U.S. Pat. No. 5,585,089 (1996 December); and Riechmann et al., *Reshaping human antibodies for therapy*, Nature 1988 Mar. 24, 332(6162):323-7.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

"Beneficial results" may include, but are in no way limited to, lessening or alleviating the severity of the disease condition, preventing the disease condition from worsening, curing the disease condition, preventing the disease condition from developing, lowering the chances of a patient developing the disease condition and prolonging a patient's life or life expectancy. In some embodiments, the disease condition is cancer.

"Cancer" and "cancerous" refer to or describe the physiological condition in mammals that is typically characterized by unregulated cell growth. Examples of cancer include, but are not limited to B-cell lymphomas (Hodgkin's lymphomas and/or non-Hodgkins lymphomas), brain tumor, breast cancer, colon cancer, lung cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, brain cancer, and prostate cancer, including but not limited to androgen-dependent prostate cancer and androgen-independent prostate cancer.

"Chemotherapeutic drugs" or "chemotherapeutic agents" as used herein refer to drugs used to treat cancer including but not limited to Albumin-bound paclitaxel (nab-paclitaxel), Actinomycin, Alitretinoin, All-trans retinoic acid, Azacitidine, Azathioprine, Bevacizumab, Bexatotene, Bleomycin, Bortezomib, Carboplatin, Capecitabine, Cetuximab, Cisplatin, Chlorambucil, Cyclophosphamide, Cytarabine, Daunorubicin, Docetaxel, Doxifluridine, Doxorubicin, Epirubicin, Epothilone, Erlotinib, Etoposide, Fluorouracil, Gefitinib, Gemcitabine, Hydroxyurea, Idarubicin, Imatinib, Ipilimumab, Irinotecan, Mechlorethamine, Melphalan, Mercaptopurine, Methotrexate, Mitoxantrone, Ocrelizumab, Ofatumumab, Oxaliplatin, Paclitaxel, Panitumab, Pemetrexed, Rituximab, Tafluposide, Teniposide, Tioguanine, Topotecan, Tretinoin, Valrubicin, Vemurafenib, Vinblastine, Vincristine, Vindesine, Vinorelbine, Vorinostat, Romidepsin, 5-fluorouracil (5-FU), 6-mercaptopurine (6-MP), Cladribine, Clofarabine, Floxuridine, Fludarabine, Pentostatin, Mitomycin, ixabepilone, Estramustine, or a combination thereof.

"Isolated" or "purified" large oncosomes as used herein refers to large oncosomes that are not in their natural milieu. No particular level of purification is required. For example, an isolated large oncosome may be removed from its native or natural environment.

"Large Oncosomes" as used herein refer to tumor-derived microvesicles that transmit signaling complexes between cell and tissue compartments. Large oncosomes are about 1 μm to about 10 μm in size. In some embodiments, large oncosomes are shed by amoeboid tumor cells. Large oncosomes comprise lipids, nucleic acids and proteins, each or a combination of which may be used to detect and/or quantify large oncosomes. In various embodiments, the size of the large oncosomes may be about 1 μm to 10 μm, about 2 μm to 10 μm, about 3 μm to 10 μm, about 4 μm to 10 μm, about 5 μm to 10 μm, about 6 μm to 10 μm, about 7 μm to 10 μm, about 8 μm to 10 μm or about 9 μm to 10 μm in size.

"Patient outcome" refers to whether a patient survives or dies as a result of treatment. A more accurate prognosis for patients as provided in this invention increases the chances of patient survival.

"Poor Prognosis" means that the prospect of survival and recovery of disease is unlikely despite the standard of care for the treatment of the cancer (for example, prostate cancer), that is, surgery, radiation, chemotherapy. Poor prognosis is the category of patients whose survival is less than that of the median survival.

"Good Prognosis" means that the prospect of survival and recovery of disease is likely with the standard of care for the treatment of the disease, for example, surgery, radiation, chemotherapy. Good prognosis is the category of patients whose survival is not less than that of the median survival.

A "recurrence" means that the cancer has returned after initial treatment.

"Non-recurrent" or "recurrence-free", as used herein means that the cancer is in remission; being recurrent means that the cancer is growing and/or has metastasized, and some surgery, therapeutic intervention, and/or cancer treatment is required to lower the chance of lethality. The "non-recurrent subjects" are subjects who have non-recurrent or recurrence-free disease, and they can be used as the control for recurrent subjects who have recurrent disease or recurrence.

"Subject" or "individual" or "animal" or "patient" or "mammal," is meant any subject, particularly a mammalian subject, for whom diagnosis, prognosis, or therapy is desired. In some embodiments, the subject has cancer. In some embodiments, the subject had cancer at some point in the subject's lifetime. In various embodiments, the subject's cancer is in remission, is re-current or is non-recurrent.

"Mammal" as used herein refers to any member of the class Mammalia, including, without limitation, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters and guinea pigs; and so on. In certain embodiments, the mammal is a human subject. The term does not denote a particular age or sex. Thus, adult and newborn subjects, as well as fetuses, whether male or female, are intended to be included within the scope of this term.

"Treatment" and "treating," as used herein refer to both therapeutic treatment and prophylactic or preventative measures, wherein the object is to prevent or slow down (lessen) the targeted pathologic condition, prevent the pathologic condition, pursue or obtain beneficial results, or lower the chances of the individual developing the condition even if the treatment is ultimately unsuccessful. Those in need of treatment include those already with the condition as well as those prone to have the condition or those in whom the condition is to be prevented. Examples of cancer treatment include, but are not limited to, active surveillance, observation, surgical intervention, chemotherapy, immunotherapy, radiation therapy (such as external beam radiation, stereotactic radiosurgery (gamma knife), and fractionated stereotactic radiotherapy (FSR)), focal therapy, systemic therapy, vaccine therapies, viral therapies, molecular targeted therapies, or a combination thereof.

"Tumor," as used herein refers to all neoplastic cell growth and proliferation, whether malignant or benign, and all pre-cancerous and cancerous cells and tissues.

"Tumor derived microvesicles (TMV)" or "microvesicles (MV)" as used herein refer to a mixture of exosomes, which are about 20 nm to about 80 nm in size, and large oncosomes which are about 1 μm to about 10 μm in size. "Oncosomes" as described in DiVizio et al, (Cancer Res. 2009, Vol 69(13) pages 5601-5609) refer to "microvesicles" and contain a mixture of cell-derived vesicles including but not limited to exosomes and large oncosomes. Microvesicles may also include shedding microvesicles, microparticles, nanovesicles, apoptotic bodies, nanoparticles and membrane vesicles.

"Therapeutic agents" as used herein refers to agents that are used to, for example, treat, inhibit, prevent, mitigate the effects of, reduce the severity of, reduce the likelihood of developing, slow the progression of and/or cure, a disease. Diseases targeted by the therapeutic agents include but are not limited to carcinomas, sarcomas, lymphomas, leukemia, germ cell tumors, blastomas, antigens expressed on various immune cells, and antigens expressed on cells associated with various hematologic diseases, autoimmune diseases, and/or inflammatory diseases.

Large oncosomes are tumor-derived microvesicles that transmit signaling complexes between cell and tissue compartments. Herein, the inventors show that amoeboid tumor cells export large oncosome (1-10 μm diameter) vesicles, derived from bulky cellular protrusions, which contain metalloproteinases, RNA, proteins (for example, caveolin-1 (Cav-1) and the GTPase ARF6), and are biologically active toward tumor cells, endothelial cells and fibroblasts. The inventors also describe methods whereby large oncosomes can be selectively sorted by flow cytometry and analyzed independently of vesicles smaller than 1 μm. Large oncosomes were identified in the circulation of different mouse models of prostate cancer and their abundance correlated with tumor progression. Similar large vesicles were also identified in human tumor tissues, but they were not detected in the benign compartment. They were more abundant in metastases.

Accordingly, the invention is based, at least in part, on the finding that large oncosomes can be visualized and quantified in biological samples (for example, in tissues and in circulation), and isolated and characterized using clinically-adaptable methods. These findings also suggest a mechanism whereby migrating tumor cells condition the tumor microenvironment and distant sites, thereby potentiating advanced disease. The present invention addresses the need for determining the likelihood of cancer metastasis and prognostication of cancer, such as prostate cancer. The invention provides assays and methods for isolating large oncosomes, determining the likelihood of cancer metastasis based on the number and/or molecular content of the large oncosomes and for treating cancer in subjects based on the number and/or molecular content of large oncosomes. In an embodiment, the cancer is prostate cancer.

Figure 10:
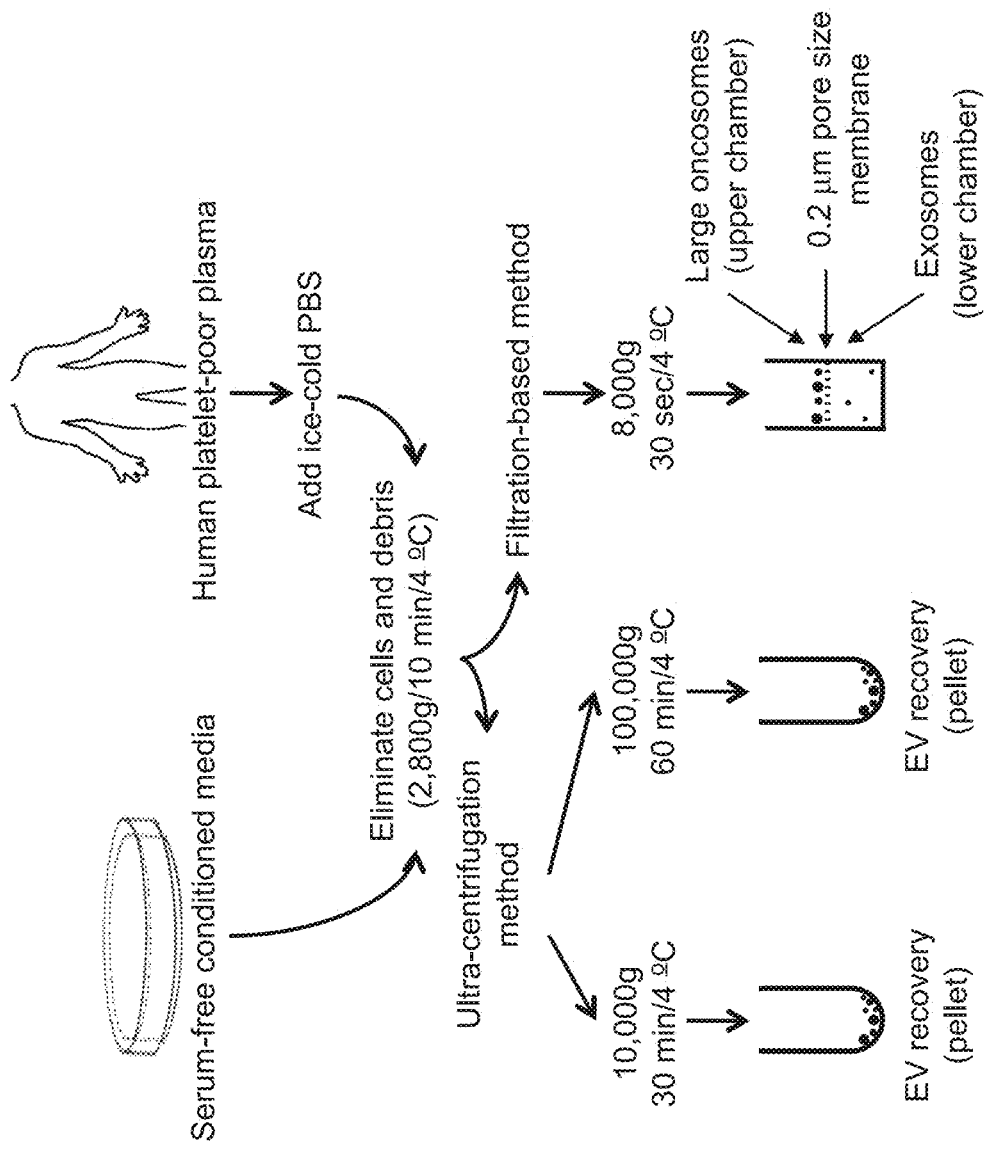
FIG. 10 depicts, in accordance with an embodiment of the invention the filtration-based isolation protocol.

Specifically, provided herein is a process comprising obtaining a biological sample from a subject that has or previously had cancer (for example, prostate cancer), processing the sample to obtain platelet-poor plasma, optionally further centrifuging the platelet-poor plasma to eliminate cells and cellular debris, filtering the supernatant using a filter with an appropriate pore size to separate large oncosomes from other microvesicles and collecting the large oncosomes. In an embodiment, the large oncosomes may be in the upper chamber of the filtration unit and the exosomes and/or other microvesicles may be in the lower chamber of the filtration unit. An embodiment of the process is depicted in FIG. 10.

In an embodiment, the invention provides a method for isolating large oncosomes from a blood sample obtained from a subject that has or previously had cancer. In an embodiment, the cancer is prostate cancer. The method includes processing the blood sample obtained from the subject to obtain platelet-poor plasma and optionally further eliminating cells and cellular debris (for example by centrifugation). The platelet-poor plasma is filtered using a filter with an appropriate pore size to separate large oncosomes from other microvesicles and the large oncosomes are collected. In an embodiment, the large oncosomes may be in the upper chamber of the filtration unit and the exosomes and/or other microvesicles may be in the lower chamber of the filtration unit. The filtration-based method for purifying large oncosomes is depicted in FIG. 10.

In an embodiment, the invention provides a method for isolating large oncosomes from a blood sample obtained from a subject that has or previously had prostate cancer. The method includes processing the blood sample obtained from the subject to obtain platelet-poor plasma and optionally further centrifuging the platelet-poor plasma at 2800 g for 10 minutes at 4° C. so as to eliminate and cells and cellular debris. The supernatant is filtered using a filter with a 0.2 µm pore size as depicted in FIG. 10 and the large oncosomes are collected. The large oncosomes may be collected from the upper chamber of the filtration unit.

For the filtration-based method described herein to isolate the large oncosomes also described herein, the type and size of filters and columns that may be used will be apparent to a person of skill in the art. For example centrifugal ultracentrifugation devices covering sample volumes from 500 µl to 2 ml with any type of low-protein retentions and wide pH-range (e.g. 2-12 pH) filter membranes, such as polyethersulfone (PES) can be used. The nominal size of the pores can range between any one or more of 0.1 µm to 1 µm, 0.2 µm to 1 µm, 0.3 µm to 1 µm, 0.4 µm to 1 µm, 0.5 µm to 1 µm, 0.6 µm to 1 µm, 0.7 µm to 1 µm, 0.8 µm to 1 µm or 0.9 µm to 1 µm.

The pore size of the filter is selected so as to enrich for large oncosomes, wherein enriching for large oncosomes comprises obtaining a greater number of large oncosomes relative to other microvesicles. For example, to separate the large oncosomes from other microvesicles such as exosomes, the pore size of the filter may be any of 200 nm, 300 nm, 400 nm, 500 nm, 600 nm, 700 nm or 800 nm. In an embodiment, the pore size is 200 nm.

In various embodiments, large oncosomes are purified or enriched-for, if after filtration, the yield is about 100% large oncosomes, 90% large oncosomes, 80% large oncosomes, 70% larger oncosomes, 60% large oncosomes or 55% large oncosomes.

Methods for obtaining platelet-poor plasma will be apparent to a person of skill in the art. For example, platelet-poor plasma may be obtained by the methods described in Floryan, K. and Berghoff, W. (*AORN Journal* October 2004, Vol 80(4), pages 667-674) and/or Cai et al. (*Int J Radiat Oncol Biol Phys* 2010 Vol 77(3), pages 867-76).

Provided herein are methods for identifying large oncosomes in a tissue sample. The method includes providing a tissue sample from the subject, fixing and embedding the tissue (for example, formalin fixing and paraffin embedding tissue) and staining the tissue sample, wherein large oncosomes are identified as large membrane sacs attached to and surrounding the cells. In some embodiments, the tissue is stained with any one or more of hematoxylin and eosin (H&E), Alizarin red S (ARS), Periodic acid-Schiff (PAS), Masson's trichrome, Romanowsky stains, Silver stain, Sudan stain, or a combination thereof. In various embodiments, staining the tissue sample encompasses contacting the embedded tissue sample with reagents that react with any one or more of lipids, proteins, DNA, RNA or a combination thereof present in the large oncosomes. The reagent may be any one or more of a nucleic acid, an antibody, a small molecule, a lipid or a combination thereof. In some embodiments, the sample is contacted with a label to produce a signal so as to detect any one or more of proteins, DNA, RNA or a combination thereof present in the large oncosomes. In exemplary embodiments, the tissue is stained for any one or more of cytokeratins, PSA, PMSA, Cav-1, MCL2, CK18, FN1, membrane proteins, lipids, carbohydrates or a combination thereof. In some embodiments, the tissue may be stained for any one or more of the proteins that are described in FIG. 13, 15 or 16.

Also provided herein are methods for determining the likelihood of cancer metastasis in a subject in need thereof. The method includes providing a sample from a subject that has or previously had cancer and detecting large oncosomes in the sample. If the sample is a tissue sample, the method comprises detecting large oncosomes by staining the tissue, wherein the large oncosomes may be identified as large membrane sacs attached to and surrounding the cells. If the sample is a blood sample, the method comprises isolating large oncosomes by the methods described herein (for example, depicted in FIG. 10) and quantifying the isolated large oncosomes. In various embodiments, the subject has an increased likelihood of cancer metastasis if there is an increase in the number of large oncosomes in the sample from the subject relative to a reference sample, or the subject has a decreased likelihood of cancer metastasis if the number of large oncosomes in the sample from the subject is the same as or decreased relative to the reference sample. In some embodiments, increased likelihood of cancer metastasis may be indicative of poor prognosis.

Further provided are methods for determining the likelihood of prostate cancer metastasis in a subject in need thereof. The method includes providing a blood sample from a subject that has or previously had prostate cancer, detecting large oncosomes in the blood sample by isolating large oncosomes according to the methods described herein (for example, depicted in FIG. 10), quantifying the isolated large oncosomes, and determining that the subject has an increased likelihood of prostate cancer metastasis if there is an increase in the number of large oncosomes in the sample from the subject relative to a reference sample, or determining that the subject has a decreased likelihood of prostate cancer metastasis if the number of large oncosomes in the sample from the subject is the same as or decreased relative to the reference sample, so as to determine the likelihood of cancer metastasis in the subject. In some embodiments, increased likelihood of prostate cancer metastasis may be indicative of poor prognosis Also provided are methods for determining the likelihood of cancer metastasis (for example, prostate cancer metastasis) in a subject in need thereof. The method includes providing a tissue sample from a subject that has or previously had cancer (for example, prostate cancer), detecting large oncosomes in the tissue sample by identifying large oncosomes attached to the cells in the sample or not-attached but surrounding the cells in the sample and determining that the subject has an increased likelihood of cancer metastasis (for example, prostate cancer metastasis) if large oncosomes are present and/or there is an increase in the number of large oncosomes in the sample from the subject relative to a reference sample, or determining that the subject has a decreased likelihood of cancer metastasis (for example, prostate cancer metastasis) if large oncosomes are absent and/or there is a decrease in the number of large oncosomes in the sample from the subject relative to the reference sample, so as to determine the likelihood of cancer metastasis in the subject. In an embodiment, the tissue sample is a prostate tissue sample. In another embodiment, the tissue sample is a sample from any other organ suspected of being cancerous.

Provided herein is a method for determining the likelihood of cancer metastasis in a subject in need thereof. The method includes providing a sample from the subject with cancer, isolating large oncosomes from the samples, detecting the presence of proteins in the large onosomes, wherein the proteins are any one or more of GLS, ATP5O, PPP2R1A, SFXN1, ECI, HBA1, HINT2, TUFM, ANP32A, PGLS, ETFA, CRYZ, MGST1, CYB5R3, TMEM33, PHB, TOP2A, KIF5B, APEX1, RDH11, or a combination thereof and determining the likelihood of cancer metastasis in the subject. In some embodiments, the subject has an increased likelihood of cancer metastasis if the sample from the subject comprises an increased numbers of large oncosomes, and/or the proteins in the large oncosomes, and/or increased levels of the proteins in the large oncosomes relative to the reference sample. In some embodiments, the subject has a decreased likelihood of cancer metastasis if the sample from the subject has decreased numbers of large oncosomes, and/or the proteins are absent in the large oncosomes and/or the subject has decreased levels of the proteins relative to the reference value. In some embodiments, the large oncosomes are isolated by the methods described herein, for example in FIG. 10.

Also provided herein is a method for determining the likelihood of cancer metastasis in a subject in need thereof. The method includes providing a sample from the subject with cancer, isolating large oncosomes from the samples, detecting the presence of proteins in the large onosomes, wherein the proteins are any one or more of SLC25A6, PHB2, ATP5B, SLC25A3, VDAC1, GOT2, STOML2, MDH2, HSPA9, VDAC2, SLC25A5, FN1, SHMT2, H2AFX, HSPD1, ECH1, PRDX3, SLC25A11, HNRNPM, HIST2H2BF, TMX1, MMYH10, NCEH1, GPI, CK18 or a combination thereof and determining the likelihood of cancer metastasis in the subject. In some embodiments, the subject has an increased likelihood of cancer metastasis if the sample from the subject comprises an increased numbers of large oncosomes, and/or the proteins in the large oncosomes, and/or increased levels of the proteins in the large oncosomes relative to the reference sample. In some embodiments, the subject has a decreased likelihood of cancer metastasis if the sample from the subject has decreased numbers of large oncosomes, and/or the proteins are absent in the large oncosomes and/or the subject has decreased levels of the proteins relative to the reference value. In some embodiments, the large oncosomes are isolated by the methods described herein, for example in FIG. 10.

Also provided herein is a method for determining the likelihood of cancer metastasis in a subject in need thereof. The method includes providing a sample from the subject with cancer, isolating large oncosomes from the samples, detecting the presence of micro RNAs in the large onosomes, wherein the micro RNA is any one or more of miR-491-3p, miR-34b, miR-1228, miR-647, miR-1227 or a combination thereof and determining that the subject has an increased likelihood of cancer metastasis if the sample from the subject comprises increased levels of large oncosomes and the micro RNAs in the large oncosomes relative to the reference sample, or determining that the subject has a decreased likelihood of cancer metastasis if the sample from the subject comprises decreased levels large oncosomes and the micro RNA relative to the reference value so as to determine the likelihood of cancer metastasis in the subject.

In some embodiments, the large oncosomes are isolated by the methods described herein, for example, in FIG. 10.

In some embodiments, an increase in the number of large oncosomes in combination with the presence of any one or more of GLS, ATP5O, PPP2R1A, SFXN1, ECI, HBA1, HINT2, TUFM, ANP32A, PGLS, ETFA, CRYZ, MGST1, CYB5R3, TMEM33, PHB, TOP2A, KIF5B, APEX1, RDH11, or a combination thereof in large oncosomes isolated from the subject is indicative of increased likelihood of cancer metastasis in the subject.

In some embodiments, an increase in the number of large oncosomes in combination with an increase in the amount of any one or more of SLC25A6, PHB2, ATP5B, SLC25A3, VDAC1, GOT2, STOML2, MDH2, HSPA9, VDAC2, SLC25A5, FN1, SHMT2, H2AFX, HSPD1, ECH1, PRDX3, SLC25A11, HNRNPM, HIST2H2BF, TMX1, MMYH10, NCEH1, ECHS1, C19orf10, SSR4, PPIB, GPI, PLEC, PRKCSH, PSMB1, LRRC59, GPT1, HNRNPU, RPN1, KRT18, SRSF3, CALR, PDIA3, HIST1H4A, NPM1, PSMB5, P4HB, PDIA4, PSMB3, LRPPRC, HSPA5, ERP29, MYH9, MDH1, TKT, LDHB, GAPDH, RAN, PDIA6, RPS5, HNRNPC, CK18 or a combination thereof in large oncosomes isolated from the subject is indicative of increased likelihood of cancer metastasis.

In some embodiments, an increase in the number of large oncosomes in combination with an increase in the levels of one or more of miR-491-3p, miR-34b, miR-1228, miR-647, miR-1227 or a combination thereof in large oncosomes isolated from the subject is indicative of increased likelihood of cancer metastasis.

In some embodiments, an increase in the number of large oncosomes in combination with the presence of any one or more of GLS, ATP5O, PPP2R1A, SFXN1, ECI, HBA1, HINT2, TUFM, ANP32A, PGLS, ETFA, CRYZ, MGST1, CYB5R3, TMEM33, PHB, TOP2A, KIF5B, APEX1, RDH11, or a combination thereof in large oncosomes isolated from the subject, and increased levels of miR-491-3p, miR-34b, miR-1228, miR-647, miR-1227 or a combination thereof in large oncosomes isolated from the subject, is indicative of increased likelihood of cancer metastasis.

In some embodiments, an increase in the number of large oncosomes in combination with the presence of any one or more of SLC25A6, PHB2, ATP5B, SLC25A3, VDAC1, GOT2, STOML2, MDH2, HSPA9, VDAC2, SLC25A5, FN1, SHMT2, H2AFX, HSPD1, ECH1, PRDX3, SLC25A11, HNRNPM, HIST2H2BF, TMX1, MMYH10, NCEH1, ECHS1, C19orf10, SSR4, PPIB, GPI, PLEC, PRKCSH, PSMB1, LRRC59, GPT1, HNRNPU, RPN1, KRT18, SRSF3, CALR, PDIA3, HIST1H4A, NPM1, PSMB5, P4HB, PDIA4, PSMB3, LRPPRC, HSPA5, ERP29, MYH9, MDH1, TKT, LDHB, GAPDH, RAN, PDIA6, RPS5, HNRNPC, CK18 or a combination thereof in large oncosomes isolated from the subject, and increased levels of miR-491-3p, miR-34b, miR-1228, miR-647, miR-1227 or a combination thereof in large oncosomes isolated from the subject, is indicative of increased likelihood of cancer metastasis.

In some embodiments, an increase in the number of large oncosomes in combination with the presence of any one or more of caveolin-1, CK18, FN1, miR-1227 or a combination thereof, is indicative of increased likelihood of cancer metastasis.

In some embodiments, an increase in the number of large oncosomes in combination with increase in the level of any one or more of caveolin-1, CK18, FN1, miR-1227 or a combination thereof relative the reference value, is indicative of increased likelihood of cancer metastasis.

In some embodiments, an increase in the number of large oncosomes in combination with increase in the level of any one or more of CK18, Akt, miR-1227, PTEN or a combination thereof or a combination thereof relative the reference value, is indicative of increased likelihood of cancer metastasis.

The invention also provides methods for treating cancer (for example, prostate cancer) in a subject in need thereof. The method comprises providing a biological sample from the subject, isolating and/or detecting large oncosomes in the sample from the subject by the methods described herein, determining the likelihood of cancer metastasis in the subject by the methods described herein and prescribing a therapy and optionally administering the therapy to the subject if the subject has an increased likelihood of cancer metastasis. In some embodiments, the sample is blood or tissue. In an embodiment, the subject has an increased likelihood of cancer metastasis if large oncosomes are present or if there is an increase in the number of large oncosomes in the sample from the subject relative to a reference sample.

In various embodiments, the samples for use with the methods and processes described herein are obtained from human subjects that have cancer or have had cancer. In an embodiment, the cancer is prostate cancer. In various embodiments, the sample is any one or more of blood, plasma, tissue, urine or a combination thereof.

Detection of Large Oncosomes

As described herein, the determination of likelihood of cancer metastasis (for example, prostate cancer metastasis) in a subject and/or treatment of cancer in a subject (for example, prostate cancer and/or prostate cancer related metastasis) includes detecting and/or quantifying large oncosomes in samples obtained from the subject. In various embodiments, the samples are blood, tissue or a combination thereof.

Further, as described herein, large oncosomes comprise lipids, nucleic acid and proteins (collectively terms the "molecular content"), each of which or a combination thereof may be used to not only detect and/or quantify large oncosomes but may also be used to identify the type of cancer that may be metastasizing.

The nucleic acid component of the molecular content of large oncosomes includes DNA and/or variants thereof such as single-stranded DNA (ssDNA), double-stranded DNA (dsDNA), cDNA and/or genomic DNA. The nucleic acid component of the molecular content of large oncosomes also includes RNA and its variants including but not limited to mRNA, rRNA, tRNA, siRNA, miRNA and/or non-coding RNA. The nucleic acid component of the molecular content of large oncosomes also includes tandem repeats (such as satellite DNA/RNA, microsatellite DNA/RNA or minisatellite DNA/RNA), interspersed repeats (such as transposons (transposable elements), Short Interspersed Nuclear Elements (SINEs, such as Alu's), Long Interspersed Nuclear Elements (LINEs such LINE-1), global direct repeats, local direct simple repeats, local direct repeats, local direct repeats with spacer and/or endogenous retroviruses (endogenous viral elements). Examples of nucleic acids that may be found in the large oncosomes are shown in Table 1. Examples of microRNAs that may be found in large oncosomes are shown in Table 2 and FIG. 18.

For example, large oncosomes, isolated from prostate cancer cell lines, also contain genomic DNA. DNA has been described in exosomes, where it is present in small amounts and largely fragmented. The amount of DNA contained in large oncosomes is more than 30 times of that found in exosomes, whereas the ratio between single and double strand is 5:1 in both. Large oncosomes can be an important source of genomic information about the tumor, in a dynamic manner. For example, large oncosomes from PC3 cells report Myc amplification on chromosome 8 and PTEN deletion on chromosome 10.

The protein component of the molecular content of the large oncosomes includes peptides, polypeptides and/or variants thereof. As described herein, the presence of large oncosomes in a sample is indicative of increased likelihood of cancer metastasis. In some exemplary embodiments, the presence of PSA or the presence of Caveolin-1 in the large oncosomes from the subject may be indicative of prostate cancer metastasis or the presence of Arf6 in the large oncosomes may be indicative of breast cancer metastasis or the presence of both PSA and Arf6 may be indicative of prostate cancer metastasis. Other proteins present in large oncosomes may also be indicative of various cancer metastasis, including prostate cancer metastasis. In some embodiments, presence or increased presence of proteins in FIGS. 15 and 16 in large oncosomes is indicative of increased likelihood of cancer metastasis.

Polypeptides may be modified or unmodified. Modifications to the polypeptides include but are not limited to any one or more of myristoylation, palmitoylation, prenylation, farnesylation, geranylgeranylation, glypiation, glycosylphosphatidylinositol (GPI) lipoylation, addition of flavin moiety (FMN or FAD), addition of heme C, phosphopantetheinylation, diphthamide formation, addition of ethanolamine phosphoglycerol, hypusine formation, acylation, alkylation, amide bond formation, butyrylation, gamma-carboxylation, glycosylation, hydroxylysine, polysialylation, malonylation, hydroxylation, iodination, nucleotide addition (such as ADP-ribosylation), oxidation, phosphate ester (O-linked) or phosphoramidate (N-linked) formation, phosphorylation, adenylylation, propionylation, pyroglutamate formation, S-glutathionylation, S-nitrosylation, Succinylation, sulfation, selenoylation, ISGylation, SUMOylation, ubiquitination, Neddylation, Pupylation, citrullination, deamidation, eliminylation, carbamylation, disulfide bridges formation, proteolytic cleavage, racemization or a combination thereof.

The lipid component of the molecular content of the large oncosomes includes but is not limited to any one or more of fatty acids, glycerolipids, glycerophospholipids, sphingolipids, sterol lipids, prenol lipids, saccharolipids, polyketides, phosphoglycerides, glycolipids, or a combination thereof.

Large oncosomes may be isolated from biological material including but not limited to any one or more of tissue, cells, blood, plasma, serum, urine, sputum, spinal fluid, pleural fluid, nipple aspirate, lymph fluid, fluid of the respiratory tract, fluid of the intestinal tract, fluid of the genitourinary tract, fluid of the lymphatic system, semen, cerebrospinal fluid, tears, saliva, intra-organ system fluid, tumor cyst fluid, amniotic fluid or a combination thereof.

In some embodiments, large oncosomes are purified from a sample obtained from a subject and detected and/or quantified without labeling the large oncosomes. In an embodiment, unlabeled large oncosomes may be quantified using flow cytometry techniques, for example, using forward scatter flow cytometry. In an embodiment, forward scatter flow cytometry is used with 1 μm to 10 μm beads to enrich for detection large oncosomes. Methods for performing forward scatter flow cytometry would be apparent to a person of skill in the art and may be performed as described in, for example, Di Vizio et al. (*Cell Cycle*. 2009 August; 8(15):2420-4), Dragovic et al. (*Nanomedicine*. 2011 December; 7(6):780-8), Wysoczynski M and Ratajczak M Z (*Int J Cancer.* 2009 Oct. 1; 125(7):1595-603). Broadly, flow cytometry analysis of large oncosomes may be performed by setting forward scatter (FSC) and side scatter (SSC) voltages as low as that the background noise, determined by running double 0.2 µm filtered PBS at the highest flow rate available (in some embodiments, no higher that 0-4 events/second. After data acquisition, large oncosomes can be analyzed by setting FSC and SSC on a logarithmic scale.

In some embodiments, the labeled large oncosomes may be detected using microfluidic systems as described in Shao et al. (*Nature Medicine* December 2012 Vol 18(12) pages 1835-1841). The methods described in Shao et al. are applied to exosomes but as would be apparent to a person of skill in the art, these methods may be applied to large oncosomes as well. The larger size of the large oncosomes may facilitate better capture of the large oncosomes.

In some embodiments, the isolated/purified large oncosomes obtained from a sample from a subject may be labeled and then quantified and/or detected. In such instances, the nucleic acids, lipids and/or proteins in the large oncosomes are labeled. In an embodiment, flow cytometry is used to detect and quantify the labeled large oncosomes. In an embodiment, large oncosomes are labeled with antibodies that bind to specific proteins of interest. For example, in order to detect and/or quantify large oncosomes obtained from a subject that has or had prostate cancer, the isolated large oncosomes may be labeled with antibodies that bind antigens including but not limited to PSA, PMSA, PSMA, FASN, Cav-1 or a combination thereof. In an embodiment, the large oncosomes labeled with antibodies are detected and/or quantified using flow cytometry. Additional proteins that may be labeled with antibodies to quantify and/or detect large oncosomes are depicted in FIGS. 15 and 16.

In further embodiments, the isolated/purified large oncosomes may be denatured and the denatured material may be used as an analyte to detect the presence of one or more proteins of interest in the large oncosomes. For example, specific antibodies may be used to detect the presence of one or more proteins of interest. Any suitable immunoassay method may be utilized, including those which are commercially available, to ascertain the presence of, and optionally quantify the amount of, the protein of interest present in the analyte. The presence (and optionally the amount) of the protein of interest in the analyte is indicative of the presence of said protein in large oncosomes. In various embodiments, the proteins of interest may be the cancer specific markers, including but not limited to the markers described herein. In various embodiments, the antibody is any one or more of a monoclonal antibody or fragment thereof, a polyclonal antibody or a fragment thereof, chimeric antibodies, humanized antibodies, human antibodies, and a single chain antibody. Extensive discussion of the known immunoassay techniques is not required here since these are known to those of skill in the art. Typical suitable immunoassay techniques include Western blots, sandwich enzyme-linked immunoassays (ELISA), radioimmunoassays (RIA), competitive binding assays, homogeneous assays, heterogeneous assays, etc. Various known immunoassay methods are reviewed, e.g., in *Methods in Enzymology,* 70, pp. 30-70 and 166-198 (1980).

Further, "sandwich-type" assays may be used with the methods described herein. Some examples of sandwich-type assays are described in U.S. Pat. No. 4,168,146 and U.S. Pat. No. 4,366,241. Alternatively, "competitive-type" assays may be used with the methods described herein. In a competitive assay, the labeled probe is generally conjugated with a molecule that is identical to, or an analog of, the analyte. Thus, the labeled probe competes with the analyte of interest for the available receptive material. Competitive assays are typically used for detection of analytes such as haptens, each hapten being monovalent and capable of binding only one antibody molecule. Examples of competitive immunoassay devices are described in U.S. Pat. No. 4,235,601, U.S. Pat. No. 4,442,204 and U.S. Pat. No. 5,208,535.

Antibodies, that may be used to detect one or more proteins of interest in a large oncosome, may be labeled. In some embodiments, the detection antibody is labeled by covalently linking to an enzyme, labeled with a fluorescent compound or metal or is labeled with a chemiluminescent compound. For example, the detection antibody can be labeled with catalase and the conversion uses a colorimetric substrate composition comprises potassium iodide, hydrogen peroxide and sodium thiosulphate; the enzyme can be alcohol dehydrogenase and the conversion uses a colorimetric substrate composition comprises an alcohol, a pH indicator and a pH buffer, wherein the pH indicator is neutral red and the pH buffer is glycine-sodium hydroxide; the enzyme can also be hypoxanthine oxidase and the conversion uses a colorimetric substrate composition comprises xanthine, a tetrazolium salt and 4,5-dihydroxy-1,3-benzene disulphonic acid. In one embodiment, the detection antibody is labeled by covalently linking to an enzyme, label with a fluorescent compound or metal, or label with a chemiluminescent compound.

Direct and indirect labels can be used in immunoassays. A direct label can be defined as an entity, which in its natural state, is visible either to the naked eye or with the aid of an optical filter and/or applied stimulation, e.g., ultraviolet light, to promote fluorescence. Examples of colored labels which can be used include metallic sol particles, gold sol particles, dye sol particles, dyed latex particles or dyes encapsulated in liposomes. Other direct labels include radionuclides and fluorescent or luminescent moieties. Indirect labels such as enzymes can also be used according to the invention. Various enzymes are known for use as labels such as, for example, alkaline phosphatase, horseradish peroxidase, lysozyme, glucose-6-phosphate dehydrogenase, lactate dehydrogenase and urease. For a detailed discussion of enzymes in immunoassays see Engvall, Enzyme Immunoassay ELISA and EMIT, Methods of Enzymology, 70, 419-439 (1980).

The antibody can be attached to a surface. Examples of useful surfaces on which the antibody can be attached for the purposes of detecting the desired antigen include nitrocellulose, PVDF, polystyrene, and nylon. The surface or support may also be a porous support (see, e.g., U.S. Pat. No. 7,939,342). The assays can be carried out in various assay device formats including those described in U.S. Pat. Nos. 4,906,439; 5,051,237 and 5,147,609 to PB Diagnostic Systems, Inc.

In some embodiments of the processes and methods described herein, detecting the presence and/or level of antibodies reactive to cancer specific markers (for examples, cancer specific proteins) present in large oncosomes includes contacting the isolated large oncosomes from the cancer patient with an antibody or a fragment thereof that specifically binds to the cancer specific marker of interest, forming an antibody-protein complex between the antibody and marker present in the sample, washing the sample to remove the unbound antibody, adding a detection antibody that is labeled and is reactive to the antibody bound to marker in the sample, washing to remove the unbound labeled detection antibody and converting the label to a detectable signal, wherein the detectable signal is indicative of the presence and/or level of the cancer specific marker in the sample from the patient. In some embodiments, the effector component is a detectable moiety selected from the group consisting of a fluorescent label, a radioactive compound, an enzyme, a substrate, an epitope tag, electron-dense reagent, biotin, digonigenin, hapten and a combination thereof. In some embodiments, the detection antibody is labeled by covalently linking to an enzyme, labeled with a fluorescent compound or metal, labeled with a chemiluminescent compound. The level of the marker may be obtained by measuring a light scattering intensity resulting from the formation of an antibody-protein complex formed by a reaction of marker in the sample with the antibody, wherein the light scattering intensity of at least 10% above a control light scattering intensity indicates the likelihood of presence of the cancer specific marker and thereby, presence of large oncosomes in the sample and increased likelihood of cancer metastasis in the subject.

In some embodiments, the isolated/purified large oncosomes obtained from a sample from a subject may be labeled and then quantified and/or detected. In such instances, the nucleic acids, lipids and/or proteins in the large oncosomes are labeled. In some embodiments, the nucleic acids are labeled. For example, mRNA encoding PSA, PMSA, Cav-1 or a combination thereof may be detected with a polynucleotide capable of hybridizing with PSA specific mRNA, PMSA specific mRNA and/or Cav-1 specific mRNA, under stringent hybridization conditions. In various embodiments, micro RNA (miRNA) may also be used to detect and/or quantify large oncosomes. In some embodiments, some miRNAs such as miR-31, miR-145, miR-18a, miR-135a, which have been shown to be de-regulated in various types of cancers including bladder, prostate, breast, and colorectal cancer, may be markers for specific types of cancers may be markers for specific types of cancers. In certain embodiments, the RNA (for example, mRNA or miRNA) expression level is determined using microarray, SAGE, blotting, RT-PCR, quantitative PCR or qNPA.

Techniques that may be used to assess the amount of nucleic acid encoding cancer-specific marker of interest present in the large oncosomes isolated from a sample obtained from a subject include but are not limited to in situ hybridization (e.g., Angerer (1987) *Meth. Enzymol* 152: 649). Preferred hybridization-based assays include, but are not limited to, traditional "direct probe" methods such as Southern blots or in situ hybridization (e.g., FISH and FISH plus SKY), and "comparative probe" methods such as comparative genomic hybridization (CGH), e.g., cDNA-based or oligonucleotide-based CGH. The methods can be used in a wide variety of formats including, but not limited to, substrate (e.g. membrane or glass) bound methods or array-based approaches. Probes that may be used for nucleic acid analysis are typically labeled, e.g., with radioisotopes or fluorescent reporters. Preferred probes are sufficiently long so as to specifically hybridize with the target nucleic acid(s) under stringent conditions. The preferred size range is from about 200 bases to about 1000 bases. Hybridization protocols suitable for use with the methods of the invention are described, e.g., in Albertson (1984) *EMBO J.* 3: 1227-1234; Pinkel (1988) *Proc. Natl. Acad. Sci. USA* 85: 9138-9142; EPO Pub. No. 430,402; *Methods in Molecular Biology*, Vol. 33: In situ Hybridization Protocols, Choo, ed., Humana Press, Totowa, N.J. (1994), Pinkel, et al. (1998) *Nature Genetics* 20: 207-211, and/or Kallioniemi (1992) *Proc. Natl Acad Sci USA* 89:5321-5325 (1992).

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided in Innis, et al. (1990) PCR Protocols, *A Guide to Methods and Applications*, Academic Press, Inc. N.Y.). Measurement of DNA copy number at microsatellite loci using quantitative PCR anlaysis is described in Ginzonger, et al. (2000) *Cancer Research* 60:5405-5409. The known nucleic acid sequence for the genes is sufficient to enable one of skill in the art to routinely select primers to amplify any portion of the gene. Fluorogenic quantitative PCR may also be used in the methods of the invention. In fluorogenic quantitative PCR, quantitation is based on amount of fluorescence signals, e.g., TaqMan and sybr green.

Other suitable amplification methods include, but are not limited to, ligase chain reaction (LCR) (see Wu and Wallace (1989) *Genomics* 4: 560, Landegren, et al. (1988) *Science* 241:1077, and Barringer et al. (1990) *Gene* 89: 117), transcription amplification (Kwoh, et al. (1989) *Proc. Natl. Acad. Sci. USA* 86: 1173), self-sustained sequence replication (Guatelli, et al. (1990) *Proc. Nat. Acad. Sci. USA* 87: 1874), dot PCR, and linker adapter PCR, etc.

In certain embodiments, other techniques may be used to determine expression of a polynucleotide gene product, including microarray analysis (Han, M., et al., *Nat Biotechnol,* 19: 631-635, 2001; Bao, P., et al., *Anal Chem,* 74: 1792-1797, 2002; Schena et al., *Proc. Natl. Acad. Sci. USA* 93:10614-19, 1996; and Heller et al., *Proc. Natl. Acad. Sci. USA* 94:2150-55, 1997) and SAGE (serial analysis of gene expression). Like MPSS, SAGE is digital and can generate a large number of signature sequences. (see e.g., Velculescu, V. E., et al., *Trends Genet,* 16: 423-425., 2000; Tuteja R. and Tuteja N. *Bioessays.* 2004 August; 26(8):916-22), although orders of magnitude fewer than that are available from techniques such as MPSS.

In certain embodiments, the term "microarray" includes a "nucleic acid microarray" having a substrate-bound plurality of nucleic acids, hybridization to each of the plurality of bound nucleic acids being separately detectable. The substrate can be solid or porous, planar or non-planar, unitary or distributed. Nucleic acid microarrays include all the devices so called in Schena (ed.), *DNA Microarrays: A Practical Approach* (Practical Approach Series), Oxford University Press (1999); *Nature Genet.* 21(1) (suppl.): 1-60 (1999); Schena (ed.), *Microarray Biochip: Tools and Technology*, Eaton Publishing Company/BioTechniques Books Division (2000). Nucleic acid microarrays may include a substrate-bound plurality of nucleic acids in which the plurality of nucleic acids are disposed on a plurality of beads, rather than on a unitary planar substrate, as described, for example, in Brenner et al., *Proc. Natl. Acad. Sci. USA* 97(4): 1665-1670 (2000). Examples of nucleic acid microarrays may be found in, for example, U.S. Pat. Nos. 6,391,623, 6,383,754, 6,383, 749, 6,380,377, 6,379,897, 6,376,191, 6,372,431, 6,351,712 6,344,316, 6,316,193, 6,312,906, 6,309,828, 6,309,824, 6,306,643, 6,300,063.

Figure 13C:
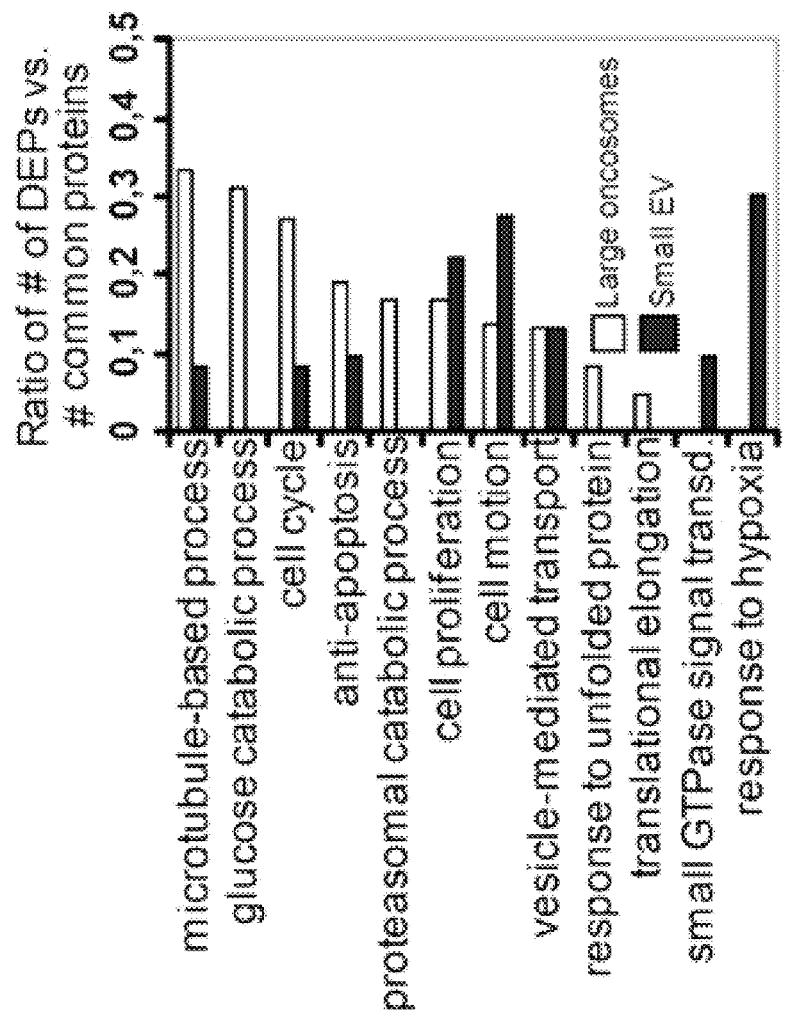

In further embodiments, the large oncosomes isolated from samples (for example, tissue, blood, plasma or a combination thereof) may be identified by detecting cancer specific (also referred to herein as cancer-specific) markers including but not limited to any one or more of cytokeratins (for example basic or neutral cytokeratins (including CK1, CK2, CK3, CK4, CK5, CK6, CK7, CK8 and CK9) and/or acidic cytokeratins (CK10, CK12, CK 13, CK14, CK16, CK17, CK18, CK19 and CK20)), prostate-specific antigen (PSA), prostate-specific membrane antigen (PSMA), caveolin-1 (Cav-1), MCL2, bladder-tumor antigen (BTA), NMP22, carcinoembryonic antigen (CEA), CA 125, CA 19-9, TPA, hormone receptors (for example estrogen and progesterone), HER2/neu antigen, CA15-3, CEA, CA27-29, bcr-abl, CA19-9, EGFR, human chorionic gonadotropin (HCG), alpha fetoprotein (AFP), neuron-specific enolase (NSE), epidermal growth factor receptor (EGFR), TA-90, S-100, immunoglobulins or free light chains, Bence Jones proteins, monoclonal protein (M-protein), CA 125, CA 72-4, LASA-P, HCG, CA 72-4, Lactate dehydrogenase (LDH), FASN or a combination thereof. Additional cancer specific markers include proteins encoded by genes set forth in Table 1. In various embodiments, the aforementioned markers may be detected in the isolated/purified large oncosomes by detecting the nucleic acids that encode the aforementioned cancer-specific markers or by detecting the proteins that encode the aforementioned cancer-specific markers. Additional embodiments of proteins that are present in large oncosomes or enriched in large oncosomes and used to identify large oncosomes are depicted in FIGS. 13, 15 and 16.

Suitable methods for assaying for the expression of various cancer-specific markers present in isolated large oncosomes (for example, non-denatured large oncosomes or denatured large oncosomes) isolated from samples obtained from subjects include but are not limited to any one or more of DNA sequencing, comparative genomic hybridization (CGH), array CGH (aCGH), SNP analysis, mRNA expression assay, RT-PCR, real-time PCR, or a combination thereof. In various embodiments, the assay for detection of nucleic acids encoding cancer-specific markers or protein levels of cancer-specific markers present in the isolated large oncosomes include any one or more of Northern blot analysis, Southern blot analysis, reverse transcription-polymerase chain reaction (RT-PCR), polymerase chain reaction (PCR), enzyme-linked immunosorbent assay (ELISA), radio-immuno assay (RIA), sodium dodecyl sulfate polyacrylamide gel electrophoresis (SDS-PAGE), Western blot analysis, mass spectrometry immune assays (MSIA), stable isotope standard capture with anti-peptide antibodies (SISCAPA), two-dimensional electrophoresis, PROTOMAP, which combines SDS-PAGE with shotgun proteomics, matrix-assisted laser desorption/ionization (MALDI), fast parallel proteolysis (FASTpp), yeast two-hybrid analysis, protein microarrays, immunoaffinity chromatography, immunoaffinity chromatography followed by mass spectrometry, dual polarization interferometry, microscale thermophoresis, phage display method, stable isotope labeling by amino acids in cell culture (SILAC) or a combination thereof. In some embodiments, the presence of cancer-specific markers in isolated large oncosomes may be ascertained by measuring the substrate upon which the marker may act, such that the substrate serves as a surrogate marker for the cancer specific marker.

In various embodiments, tissue samples obtained from a subject with cancer (for example, prostate cancer), may be analyzed for large oncosomes. Large oncosomes in the tissue sample may be identified by staining the tissue using any one or more of hematoxylin and eosin (H&E) stain, Periodic acid-Schiff (PAS) stain, Sudan stain, cytostain, Papanicolaou stain, Nissl stain, azocarmine stain, neutral red or janus green. In further embodiments, the tissue sample may be analyzed by immuno-histochemical staining Immuno-histochemical staining (IHS) may provide information about the presence, location and distribution of large oncosomes that may be bound to the tissue sample or may be present surrounding the tissue sample. Antigens for HIS include proteins, peptides, nucleic acids, small molecules or any other molecule that may be specifically recognized by an antibody. In various embodiments, the antibodies may specifically bind the cancer specific markers described herein. Unbound antibody may be removed by washing. The specifically bound antibody may be detected by treating the bound antibody with, for example a labeled secondary antibody or labeled avidin/streptavidin. Suitable labels for immunohistochemistry include but are not limited to fluorophores such as fluoroscein and rhodamine, enzymes such as alkaline phosphatase and horse radish peroxidase, and radionuclides such as $^{32}P$ and $^{125}I$. Examples of gene product markers that may be detected by immuno-histochemical staining include but are not limited to cytokeratins (for example basic or neutral cytokeratins (including CK1, CK2, CK3, CK4, CK5, CK6, CK7, CK8 and CK9) and/or acidic cytokeratins (CK10, CK12, CK 13, CK14, CK16, CK17, CK18, CK19 and CK20)), prostate-specific antigen (PSA), prostate-specific membrane antigen (PSMA), caveolin-1 (Cav-1), MCL2, bladder-tumor antigen (BTA), NMP22, carcinoembryonic antigen (CEA), CA 125, CA 19-9, TPA, hormone receptors (for example estrogen and progesterone), HER2/neu antigen, CA15-3, CEA, CA27-29, bcr-abl, CA19-9, EGFR, human chorionic gonadotropin (HCG), alpha fetoprotein (AFP), neuron-specific enolase (NSE), epidermal growth factor receptor (EGFR), TA-90, S-100, immunoglobulins or free light chains, Bence Jones proteins, monoclonal protein (M-protein), CA 125, CA 72-4, LASA-P, HCG, CA 72-4, Lactate dehydrogenase (LDH) or a combination thereof. Additional examples of gene-product markers that may be detected by immuno-histochemical staining include but are not limited those listed in FIGS. 13, 15 and 16. Additional cancer specific markers include proteins encoded by genes set forth in Table 1.

Reference Values

In various embodiments of the processes and methods described herein, the reference value is based on the presence and/or number of large oncosomes in a sample obtained from a subject having cancer (for example, prostate cancer). In one embodiment, large oncosomes are isolated from a blood sample obtained from a subject that has cancer or had cancer. In another embodiment, large oncosomes are detected in a tissue sample obtained from a subject that has cancer of had cancer. As used herein, "subjects that had cancer" refers to subjects that had cancer at any point in their lifetimes and the cancer is in remission.

In some embodiments, the reference value is the mean or median number of number of large oncosomes and the molecular content (such as proteins, nucleic acids, lipids) of the large oncosomes in a population of subjects that do not have cancer. In such subjects, complete absence of large oncosomes may be expected.

In some embodiments, the reference value is the mean or median number of large oncosomes and the molecular content (such as proteins, nucleic acids, lipids) of the large oncosomes in a population of subject that have cancer in remission.

In an additional embodiment, the reference value is the mean or median number of large oncosomes and the molecular content (such as proteins, nucleic acids, lipids) of large oncosomes in one or more samples from the subject wherein the one or more samples are obtained at a different (for example, an earlier) time point, such as during diagnosis, before treatment, after treatment or a combination thereof. In an embodiment, the cancer is prostate cancer.

Exemplary embodiments of the molecular content of large oncosomes include proteins depicted in FIGS. 13, 15 and 16, micro RNAs depicted in FIG. 18 or a combination thereof.

In various embodiments, the large oncosomes in the cancer subject compared to the reference value is increased by at least or about 10%, 20%, 30%, 40%, 50%, 60%, 70%, 80%, 90% or 100%. In various embodiments, the large oncosomes in the cancer subject compared to the reference value is increased by at least or about 1-fold, 2-fold, 3-fold, 4-fold, 5-fold, 10-fold, 15-fold, 20-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, 100-fold or a combination thereof.

Therapies

In accordance with various embodiments of the invention, the therapies that may be prescribed to a subject with increased likelihood of cancer metastases may be selected, used and/or administered to treat a cancer patient (for example a prostate cancer patient). In various embodiments, the therapy may be any one or more of surgery, radiation, chemotherapy, immunotherapy, vaccine or combinations thereof.

In some embodiments, chemotherapeutic agents may be selected from any one or more of cytotoxic antibiotics, antimetabolities, anti-mitotic agents, alkylating agents, arsenic compounds, DNA topoisomerase inhibitors, taxanes, nucleoside analogues, plant alkaloids, and toxins; and synthetic derivatives thereof. Exemplary compounds include, but are not limited to, alkylating agents: treosulfan, and trofosfamide; plant alkaloids: vinblastine, paclitaxel, docetaxol; DNA topoisomerase inhibitors: doxorubicin, epirubicin, etoposide, camptothecin, topotecan, irinotecan, teniposide, crisnatol, and mitomycin; anti-folates: methotrexate, mycophenolic acid, and hydroxyurea; pyrimidine analogs: 5-fluorouracil, doxifluridine, and cytosine arabinoside; purine analogs: mercaptopurine and thioguanine; DNA antimetabolites: 2'-deoxy-5-fluorouridine, aphidicolin glycinate, and pyrazoloimidazole; and antimitotic agents: halichondrin, colchicine, and rhizoxin. Compositions comprising one or more chemotherapeutic agents (e.g., FLAG, CHOP) may also be used. FLAG comprises fludarabine, cytosine arabinoside (Ara-C) and G-CSF. CHOP comprises cyclophosphamide, vincristine, doxorubicin, and prednisone. In another embodiments, PARP (e.g., PARP-1 and/or PARP-2) inhibitors are used and such inhibitors are well known in the art (e.g., Olaparib, ABT-888, BSI-201, BGP-15 (N-Gene Research Laboratories, Inc.); INO-1001 (Inotek Pharmaceuticals Inc.); PJ34 (Soriano et al., 2001; Pacher et al., 2002b); 3-aminobenzamide (Trevigen); 4-amino-1,8-naphthalimide; (Trevigen); 6(5H)-phenanthridinone (Trevigen); benzamide (U.S. Pat. No. Re. 36,397); and NU1025 (Bowman et al.).

In various embodiments, therapies include use of chemotherapeutic agents to treat prostate cancer. Such agents include but are not limited to Abiraterone Acetate, Cabazitaxel, Degarelix, Denosumab, Docetaxel, Enzalutamide, Jevtana (Cabazitaxel), Leuprolide Acetate, Lupron (Leuprolide Acetate), Lupron Depot (Leuprolide Acetate), Lupron Depot-3 Month (Leuprolide Acetate), Lupron Depot-4 Month (Leuprolide Acetate), Lupron Depot-Ped (Leuprolide Acetate), Prednisone, Prolia (Denosumab), Provenge (Sipuleucel-T), Radium 223 Dichloride, Sipuleucel-T, Taxotere (Docetaxel), Viadur (Leuprolide Acetate), Xgeva (Denosumab), Xofigo (Radium 223 Dichloride), Xtandi (Enzalutamide), Zytiga (Abiraterone Acetate) or a combination thereof.

In various embodiments, therapies include, for example, radiation therapy. The radiation used in radiation therapy can be ionizing radiation. Radiation therapy can also be gamma rays, X-rays, or proton beams. Examples of radiation therapy include, but are not limited to, external-beam radiation therapy, interstitial implantation of radioisotopes (I-125, palladium, iridium), radioisotopes such as strontium-89, thoracic radiation therapy, intraperitoneal P-32 radiation therapy, and/or total abdominal and pelvic radiation therapy. For a general overview of radiation therapy, see Hellman, Chapter 16: Principles of Cancer Management: Radiation Therapy, 6th edition, 2001, DeVita et al., eds., J. B. Lippencott Company, Philadelphia. The radiation therapy can be administered as external beam radiation or teletherapy wherein the radiation is directed from a remote source. The radiation treatment can also be administered as internal therapy or brachytherapy wherein a radioactive source is placed inside the body close to cancer cells or a tumor mass. Also encompassed is the use of photodynamic therapy comprising the administration of photosensitizers, such as hematoporphyrin and its derivatives, Vertoporfin (BPD-MA), phthalocyanine, photosensitizer Pc4, demethoxy-hypocrellin A; and 2BA-2-DMHA.

In various embodiments, therapies include, for example, immunotherapy. Immunotherapy may comprise, for example, use of cancer vaccines and/or sensitized antigen presenting cells. The immunotherapy can involve passive immunity for short-term protection of a host, achieved by the administration of pre-formed antibody directed against a cancer antigen or disease antigen (e.g., administration of a monoclonal antibody, optionally linked to a chemotherapeutic agent or toxin, to a tumor antigen). Immunotherapy can also focus on using the cytotoxic lymphocyte-recognized epitopes of cancer cell lines.

In various embodiments, therapies include, for example, hormonal therapy, Hormonal therapeutic treatments can comprise, for example, hormonal agonists, hormonal antagonists (e.g., flutamide, bicalutamide, tamoxifen, raloxifene, leuprolide acetate (LUPRON), LH-RH antagonists), inhibitors of hormone biosynthesis and processing, and steroids (e.g., dexamethasone, retinoids, deltoids, betamethasone, cortisol, cortisone, prednisone, dehydrotestosterone, glucocorticoids, mineralocorticoids, estrogen, testosterone, progestins), vitamin A derivatives (e.g., all-trans retinoic acid (ATRA)); vitamin D3 analogs; antigestagens (e.g., mifepristone, onapristone), or antiandrogens (e.g., cyproterone acetate).

As described herein, large oncosomes contain active Akt kinase that may serve as a prognostic marker and therapeutic target. LO contain active kinases (such as Akt) which may activate c-Myc when internalized by recipient cells, resulting in cell proliferation and angiogenesis (and therefore cancer metastasis). Therefore, kinase inhibitors may be used as therapeutic agents, for example, to target LO. Accordingly, in one embodiment, provided herein are methods for treating, preventing and/or reducing the severity of cancer metastasis in a subject in need thereof comprising providing one or more kinase inhibitor (for example, to target Akt kinase in large oncsomes) and administering an effective amount of the kinase inhibitor to the subject so as to treat, prevent and/or reduce the severity of cancer metastasis in the subject. In some embodiments, the kinase inhibitors are conjugated to antibodies so as to target the kinase inhibitors to the large oncosomes. Examples of tyrosinae kinases include but are not limited to Afatinib, Axitinib, Bosutinib, Cetuximab, Crizotinib, Dasatinib, Erlotinib, Fostamatinib, Gefitinib, Ibrutinib, Imatinib, Lapatinib, Lenvatinib, Mubritinib, Nilotinib, Pazopanib, Pegaptanib, Ruxolitinib, Sorafenib, SU6656, Sunitinib, Vandetanib and Vemurafenib.

The duration and/or dose of treatment with anti-cancer therapies may vary according to the particular anti-cancer agent or combination thereof. An appropriate treatment time for a particular cancer therapeutic agent will be appreciated by the skilled artisan. The invention contemplates the continued assessment of optimal treatment schedules for each cancer therapeutic agent, where the genetic signature of the cancer of the subject as determined by the methods of the invention is a factor in determining optimal treatment doses and schedules.

In various embodiments, the subject for whom predicted efficacy of an anti-cancer therapy is determined, is a mammal (e.g., mouse, rat, primate, non-human mammal, domestic animal such as dog, cat, cow, horse), and is preferably a human. In another embodiment of the methods of the invention, the subject has not undergone chemotherapy or radiation therapy. In alternative embodiments, the subject has undergone chemotherapy or radiation therapy. In related embodiments, the subject has not been exposed to levels of radiation or chemotoxic agents above those encountered generally or on average by the subjects of a species. In certain embodiments, the subject has had surgery to remove cancerous or precancerous tissue. In other embodiments, the cancerous tissue has not been removed, e.g., the cancerous tissue may be located in an inoperable region of the body, such as in a tissue that is essential for life, or in a region where a surgical procedure would cause considerable risk of harm to the patient, or e.g., the subject is given the anti-cancer therapy prior to removal of the cancerous tissue.

The invention provides a system for determining the likelihood of cancer metastasis wherein large oncosomes are isolated from biological samples obtained from cancer patients. The system includes a sample analyzer configured to produce a signal for mRNA encoding a cancer marker of interest or an miRNA that may be a cancer marker present in the isolated large oncosomes and a computer sub-system programmed to calculate, based on the mRNA or miRNA, whether the signal is greater than or not greater than a reference value.

The invention also provides a system for determining the likelihood of cancer metastasis wherein large oncosomes are isolated from biological samples obtained from cancer patients. The system comprises a sample analyzer configured to produce a signal when a cancer marker specific antibody binds the cancer marker in the isolated large and a computer sub-system programmed to calculate, based on the antibody binding whether the signal is greater than or not greater than a reference value.

In some embodiments, the computer sub-system is programmed to compare the aforementioned signals to reference values to determine a likelihood of cancer metastasis based on an algorithm that classifies the patient as likely to have metastasized form of cancer if the presence of large oncosomes is increased in the subject relative to a reference value.

The invention further provides a computer program product embodied in a computer readable medium that, when executed on a computer, performs steps comprising detecting cancer marker expression in a sample comprising isolated large oncosomes obtained from a cancer patient and comparing the cancer marker expression to a reference value.

The invention further provides combinations and kits comprising isolated large oncosomes and one or more reagents to react with the lipids, carbohydrates, proteins, DNA, RNA or a combination thereof, in the large oncosomes. The reagent may be any one or more of a nucleic acid, an antibody, a small molecule, a lipid or a combination thereof. The reagent may further comprises a label to produce a signal so as to detect the proteins, DNA, RNA or a combination thereof in the oncosomes. The label may be any one or more of a radiolabel, a chromophore, a fluorophore or a combination thereof.

Advantages

The "oncosomes" described in Di Vizio et al. (Cancer Res 2009 Vol 69(13) pages 5601-5609), are a mixture exosomes and large oncosomes. Specifically, as shown in FIGS. 10 and 11(a), the oncosome purification method described in DiVizio et al. results in a mixture of exosomes (FIG. 11(a) middle panel black bar) and large oncosomes (FIG. 11(a), middle panel white bars), compared to the filtration method described herein (FIG. 11(a) right panel) which yields an isolated population of large oncsomes.

As described herein, presence of large oncosomes in a subject is indicative of increased likelihood of cancer metastasis. The isolation methods described herein, such as (i) the filtration method described in FIG. 11(a), optionally followed by fluorescence-activated cell sorting (FACS) with size beads of 1 µm to 10 µm, and (ii) differential centrifugation followed by FACS with size beads of 1 µm to 10 µm, rapidly and selectively enrich for large oncosomes. The purified large oncosomes are selected away from other microvesicles, including exosomes to yield essentially purified large oncosomes (FIG. 1 and (FIG. 11(a) right panel)). Since presence and/or an increase in the number of large oncosomes are indicative of increased likelihood of cancer metastasis, the invention provides a quick and simple test (for example a blood test) that may be used to detect cancer metastasis. Since, as described herein, the large oncosomes are produced by cancer cells only and may be detected even without a label, metastasis of any cancer that results in formation and circulation of large oncosomes, may be detected by a simple blood test. Exosomes in contrast may be produced by any cell type (Cocucci et al, 2009; Momen-Heravi F et al. 2013) and exosomes are not necessarily indicative cancer metastasis (compare FIGS. 6C and 6D).

As shown in the exosome field, in vitro results are not necessarily predictive of in vivo events. For example, (see Peinado et al. (*Nature* Medicine 2012 Vol 18(6) pages 883-891) page 884 left column line 16). Di Vizio et al. described in vitro observations in a mixture of microvesicles shed by cultured cancer cells, but it wasn't until the large oncosomes were isolated by the methods described herein that it was apparent that not only are the large oncosomes not an in vitro artifact but are in fact, biologically active comparably if not superior to exosomes and are a marker for cancer metastasis.

EXAMPLES

Example 1

Methods of the Invention

Cell Culture

LNCaP, DU145, PC3 and WPMY-1 were from the American Type Culture Collection (ATCC) (Di Vizio D et al., Oncosome formation in prostate cancer: association with a region of frequent chromosomal deletion in metastatic disease, Cancer Res 2009, 69:5601-5609; Adam R M et al., Cholesterol sensitivity of endogenous and myristoylated Akt, Cancer Res 2007, 67:6238-6246; Di Vizio D et al., Caveolin-1 interacts with a lipid raft-associated population of fatty acid synthase, Cell Cycle 2008, 7:2257-2267).

LNCaP/LacZ and LNCaP/MyrAkt1 lines were described (Adam R M et al., Cholesterol sensitivity of endogenous and myristoylated Akt, Cancer Res 2007, 67:6238-6246). For the generation of LNCaP/Vo and LNCaP/Cav-1, parental LNCaP were plated at 70-80% confluence and transfected using Lipofectamine™ 2000 Tranfection Reagent (Invitrogen). Stable populations were isolated following selection with Gentamicin G418 0.5 mg/ml. LNCaP were cultured in RPMI-1640 medium supplemented with 10% fetal bovine serum (FBS; Valley Biomedical) 2 mmol/L L-glutamine, 100 U/ml penicillin, and 100 µg/ml streptomycin (all from Invitrogen). DU145 and PC3 were cultured in DMEM supplemented with 10% and 5% (WPMY-1) FBS, 2 mmol/L L-glutamine, 100 U/ml penicillin, and 100 µg/ml streptomycin.

DNA and RNA Extraction

Total nucleic acid was isolated by the TRIzol (Invitrogen) extraction method, and concentration determined by NanoDrop 2000c spectrophotometer (Biolab). RNA and DNA were fractionated by gel electrophoresis on a 2% agarose gel (Invitrogen) and nucleic acid purity was evaluated by RNase A (Invitrogen) and DNase 1 (Sigma) digestion. 100 ng nucleic acid from vesicles obtained from $2 \times 10^7$ LNCaP/MyrAkt1 cells was suspended in 15 µl buffer for gel electrophoresis.

Immunoblot Analysis

Cells and purified vesicles were lysed and analyzed by SDS-PAGE and western blotting with the following antibodies: rabbit polyclonal Cav-1 (N-20) (Santa Cruz); HA.11 mAb, clone 16B12 (Covance); Akt1 and p-Akt1 (S473), clone D9E (Cell Signaling), at a dilution of 1:1000; β-actin mAb, clone AC-15 (Sigma), at a dilution of 1:5000. ARF6 antibody was obtained from Brigham and Women Hospital, Boston, Mass. (Powelka A M et al., Stimulation-dependent recycling of integrin beta1 regulated by ARF6 and Rab11, Traffic 2004, 5:20-36; Di Vizio D et al., Oncosome formation in prostate cancer: association with a region of frequent chromosomal deletion in metastatic disease, Cancer Res 2009, 69:5601-5609). 15 µg protein per lane was loaded for western blotting.

Immunofluorescence Microscopy

Cells were incubated on ice with FITC-conjugated cholera toxin B (CTxB) subunit (Sigma) or Alexa 594-conjugated CTxB (Molecular Probes) and analyzed as previously described (Di Vizio D et al., Caveolin-1 interacts with a lipid raft-associated population of fatty acid synthase, Cell Cycle 2008, 7:2257-2267). For selected experiments, LNCaP/MyrAkt1 were then fixed in 4% paraformaldehyde (PFA), stained with FITC conjugated HA (MyrAkt1) tag (Santa Cruz Biotechnology), and imaged using an Axioplan 2 microscope (Zeiss) (Di Vizio D et al., Caveolin-1 interacts with a lipid raft-associated population of fatty acid synthase, Cell Cycle 2008, 7:2257-2267).

Animal Models and Tumor Xenografts

All experiments were performed in compliance with the guidelines of the Institutional Animal Care and Use Committee, Children's Hospital Boston. We established subcutaneous xenografts injecting $2 \times 10^6$ LNCaP/LacZ or LNCaP/MyrAkt1 cells into the flanks of 8 and 16 SCID mice, respectively. Tumor growth was monitored 3 times per week from detection of the first palpable tumors and the mice were sacrificed before reaching the maximum tumor burden of 2,000 cm$^3$ at all 4 sites (6 weeks post implantation). At necropsy, tumors were removed, weighed, fixed in 10% buffered formalin and embedded in paraffin for histological analysis. The colony of TRAMP and age-matched wild-type mice were maintained in a C57BL6/J background and genotyped as described (Wang S et al., Prostate-specific deletion of the murine Pten tumor suppressor gene leads to metastatic prostate cancer, Cancer Cell 2003, 4:209-221; Chen Z et al., Crucial role of p53-dependent cellular senescence in suppression of Pten-deficient tumorigenesis, Nature 2005, 436:725-730). In some experiments, TRAMP mice from an F1 C57BL6/J X FVB/N cross were used. Pten$^{PbKO}$/Trp53$^{PbKO}$ and Pten$^{PbKO}$/KRAS mice were maintained as described (Wang S et al., Prostate-specific deletion of the murine Pten tumor suppressor gene leads to metastatic prostate cancer, Cancer Cell 2003, 4:209-221).

Large Oncosome Isolation

Large oncosomes were purified from conditioned medium or from 500 µl of platelet-poor plasma as previously described (Di Vizio D et al., Oncosome formation in prostate cancer: association with a region of frequent chromosomal deletion in metastatic disease, Cancer Res 2009, 69:5601-5609). Briefly, cells and debris were eliminated by centrifugation at 2,800×g per 10 min. The supernatant was centrifuged at 100,000×g for 80 min. Purified oncosomes were washed in PBS, stained with the indicated antibodies, fixed and permeabilized in ethanol, then analyzed by FACS and sorted using 1 and 10 µm bead standards, followed by microscopic examination. In selected experiments, unfixed large oncosomes were sorted using size gates with 1 and 10 µm bead standards and used for biological experiments.

Gelatin Zymography and In Vitro Degradation Assay

Lysed particles isolated from growth media were analyzed by gelatin zymography (substrate gel electrophoresis) (Braunhut S J and Moses M A. Retinoids modulate endothelial cell production of matrix-degrading proteases and tissue inhibitors of metalloproteinases (TIMP), J Biol Chem 1994, 269:13472-13479). The gelatin degradation assay was performed by seeding isolated particles (1-5 µg) on FITC-labeled gelatin coated coverslips for 1.5 hr, at 37° C. using a modification of a published protocol (Ramachandran A et al., An Akt- and Fra-1-dependent pathway mediates platelet-derived growth factor-induced expression of thrombomodulin, a novel regulator of smooth muscle cell migration, Am J Pathol 2010, 177:119-131).

Migration Assays $1 \times 10^5$ mouse dermal endothelial cells (MDEC), tumor endothelial cells (TEC), or DU145 cells treated with vesicles shed from cells (10 µg/mL) were stained with CellTracker RED CMPTX (Invitrogen), and assayed in Transwell FluoroBlok inserts for 16 hours. Cell migration was measured as described (Ramachandran A et al., An Akt- and Fra-1-dependent pathway mediates platelet-derived growth factor-induced expression of thrombomodulin, a novel regulator of smooth muscle cell migration, Am J Pathol 2010, 177:119-131). Alternatively, WPMY-1 cells ($1.5 \times 10^5$) were seeded into the bottom of 24-well plates and treated for 24 hr with 10 µg/mL LNCaP/MyrAkt1 vesicles. DU145 cells ($1 \times 10^5$), labeled with CellTracker, were seeded into FluoroBlok inserts placed into the WPMY-1-conditioned media and migration monitored as above. Vesicles were unfixed when used in migration assays. Results represent fold-changes from the average of biological triplicates performed in technical duplicate.

Flow Cytometry

Purified vesicles were stained with propidium iodide (PI) Staining Buffer (BD Bioscience) or with the indicated antibodies, were processed on a Moflo High-Speed Cell Sorter (Beckman-Coulter) and analyzed using FlowJo software (Treestar). 1 and 10 µm bead standards (Spherotech Inc.) were used to set size gates. At least 3,000 events were recorded (Wersto R P et al., Doublet discrimination in DNA cell-cycle analysis, Cytometry 2001, 46:296-306). The following antibodies were used: HA-probe (F-7) FITC (Santa Cruz), at a dilution of 1:200, Cav-1 (N-20) (Santa Cruz), at dilution 1:200.

Electron Microscopy

Large Oncosomes.

Purified material was adsorbed to glow-discharged, carbon-coated copper grids and stained with 0.75% (w/v) uranyl formate as described (Ohi M et al. Negative Staining and Image Classification—Powerful Tools in Modern Electron Microscopy, Biol Proced Online 2004, 6:23-34). Images were collected on a Philips CM10 electron microscope (FEI) operated at an acceleration voltage of 100 kV. Images were recorded on a 1K CCD camera (Gatan) at a magnification of 50,000× and a defocus of about −1.5 µm.

Human Xenografts.

Sections from the paraffin embedded subcutaneous tumors were deparaffinized and fixed for 2 hours in Karnovsky fixative before post-fixation with 1% OsO4 and 0.03 g/4 ml of potassium ferrocyanide. Sections were then stained overnight with 2% uranyl acetate, dehydrated and embedded overnight with a 1:1 mixture of LX 112 resin and 100% ethanol. Electron micrographs were collected on a JEOL 1400 TEM operated at an acceleration voltage of 120 kV.

Immunohistochemistry

Sections from the paraffin embedded mice tumors, human core biopsies, and human TMA were stained (Adam R M et al., Cholesterol sensitivity of endogenous and myristoylated Akt, Cancer Res 2007, 67:6238-6246; Di Vizio D et al., Caveolin-1 interacts with a lipid raft-associated population of fatty acid synthase, Cell Cycle 2008, 7:2257-2267Di Vizio D et al., Caveolin-1 is required for the upregulation of fatty acid synthase (FASN), a tumor promoter, during prostate cancer progression, Cancer Biol Ther 2007, 6:1263-1268) with the following antibodies: Akt mAb (Cell Signaling) at a dilution of 1:500; HA.11 mAb, clone 16B12 (Covance), at a dilution of 1:100, CK18 rabbit polyclonal Ab (Epitomics), at dilution of 1:200.

Patients and Samples

Three human tissue cohorts were used: 1) core biopsies with localized prostate cancer from 15 patients from the Department of Pathology of University of Naples, Italy; 2) a TMA from Ulm, Germany, containing 26 multifocal specimens, with at least 2 distinct cancer foci in the prostate gland and 1 lymph node metastasis; 3) a TMA containing 36 benign prostate samples, 36 organ confined, and 36 metastatic tumors, of which 11, 20 and 23 samples, respectively, were available for the analysis (Di Vizio D et al., Caveolin-1 interacts with a lipid raft-associated population of fatty acid synthase, Cell Cycle 2008, 7:2257-2267; Di Vizio D et al., An absence of stromal caveolin-1 is associated with advanced prostate cancer, metastatic disease and epithelial Akt activation, Cell Cycle 2009, 8:2420-2424; Mukhopadhyay N K et al., Heterogeneous nuclear ribonucleoprotein K is a novel regulator of androgen receptor translation, Cancer Res 2009, 69:2210-2218; Cinar B et al., The pro-apoptotic kinase Mst1 and its caspase cleavage products are direct inhibitors of Akt1, EMBO J 2007, 26:4523-4534). Informed consent was obtained from all subjects.

Statistical Analysis

Comparisons between experimental groups were performed using two-tailed, unpaired Student's t test. Pearson's chi-square test was used to assess the correlation between percentage of MyrAkt1-positive events and tumor weight. Fisher exact test was applied to assess association between presence of large oncosome-like structures and Gleason score groups and metastases. In all experiments, a $p<0.05$ was considered significant.

Protein Separation and Digestion

Proteins were separated and digested as described (Yang, W. et al., *Molecular & cellular proteomics: MCP* 2011, 10(6), M110 007492). SILAC-labeled proteins were mixed at a 1:1 ratio, separated by 10% SDS-PAGE, and stained with Coomassie Brilliant Blue solution (Bio-Rad). Each lane was cut into ten gel slices of similar size and further cut into about 1 mm3 particles. Proteins were reduced by 10 mM dithiothreitol (DTT), alkylated by 55 mM iodoacetamide, and digested with mass spectrometry-grade trypsin (Promega) at 37° C. for 16 h. Tryptic peptides were successively extracted with 100 µL of 5% acetic acid, 100 µL of 2.5% acetic acid and 50% acetonitrile, and 100 µL of 100% acetonitrile. Samples were dried in a SpeedVac concentrator (Thermo Scientific) and stored at −80° C. until MS analysis.

LC-MS/MS Analysis

Tryptic peptides were redissolved with 20 µL 1.5% acetic acid and 5% acetonitrile. Samples (10 µL each) were analyzed by online C18 nanoflow reversed-phase HPLC (Eksigent nanoLC·2D™) connected to an LTQ Orbitrap XL mass spectrometer (Thermo Scientific) as described previously (Yang, W et al, *Molecular & cellular proteomics: MCP* 2010, 9(1), 54-70.27; Dowal L. et al., *Blood* 2011, 118, (13), e62-73). Briefly, samples were loaded onto a 15 cm nanospray column (75 µm inner diameter, Magic C18 AQ, 3 µm particle size, 200 Å pore size, Precision Capillary Columns) and separated at 300 nL/min with a 60-min gradient from 5 to 35% acetonitrile in 0.1% formic acid. MS data were acquired in a data-dependent manner selecting the fragmentation events based on the precursor abundance in the survey scan (350-1600 Th). The resolution of the survey scan was set at 30,000 at m/z 400 Th. Dynamic exclusion was 90 s. After each survey scan, up to ten collision-induced dissociation (CID) MS/MS spectra were acquired in the linear ion trap. The mass spectrometry proteomics data have been deposited to the ProteomeXchange Consortium (http://proteomecentral.proteomexchange.org) via the PRIDE partner repository (Vizcaino et al., Nucleic Acids Res. January 2013; 41(D1): D1063-D1069) with the dataset identifier PXD000776.

Protein Identification and Quantitation

The MS data were analyzed using MaxQuant (v1.3.0.5) (Cox, J. et al., *Nature biotechnology* 2008, 26(12), 1367-72). Proteins were identified by searching MS/MS spectra against the Uniprot database for Human (released on Sep. 11, 2012, 84,680 entries) combined with 262 common contaminants by the Andromeda search engine (Cox, J. et al., *Journal of proteome research* 2011, 10(4), 1794-805), with second peptide identification enabled. Carbamidomethylation of cysteines was set as a fixed modification, oxidation of methionines and acetylation of the protein N-terminus as variable modifications. Trypsin allowing for cleavage N-terminal to proline was chosen as the enzyme specificity. A maximum of two missed cleavages were allowed. The minimum peptide length was specified to be seven amino acids. The maximal mass tolerance in MS mode was set to 20 ppm for first search and 6 ppm for main search, and in MS/MS mode 0.7 Da. The maximum false discovery rates (FDR) for peptide and protein identifications were specified as 0.01.

Identification of Differentially Expressed Proteins (DEPs)

To identify differentially expressed proteins (DEPs) in large oncosomes (10K fraction) compared to small EVs (100K fraction), we first normalized the intensities of proteins identified with more than two sibling peptides in at least one out of two replicates, in either the large or small EV fractions, using a quantile normalization method (Bolstad, B M et al., Bioinformatics 2003, 19(2), 185-93). From these normalized intensities, the proteins differentially expressed between large and small EVs were identified using an integrative statistical testing method, as previously reported (Moon, P G et al., Proteomics 2011, 11(12), 2459-75; Lee H J et al., The Journal of biological chemistry 2010, 285(12), 9262-72). Briefly, for each protein, we performed 1) two independent tests, a test and a log 2 median ratio test; 2) adjusted P values from each two-tailed tests were computed using an empirical distribution of the null hypothesis (that the means of the genes are not different), which was obtained from random permutations of the samples; 3) the individual adjusted P values were combined to compute the FDR using Stouffer's method (Hwang D et al., PNAS 2005, 102, (48), 17296-301). Note that when using this integrative statistical testing, for the peptides for which the T-test is not applicable due to the availability of only one intensity value in a given condition, the adjusted P-value from the log 2 median ratio test becomes the FDR. We identified large oncosome and small EV proteins, with a FDR<0.05 and a fold change ≥2. In addition, to identify proteins uniquely detected in large oncosomes or small EVs, we employed the following criteria: 1) being identified in at least one replicate with more than two sibling peptides and 2) being quantified in one single condition, not quantified in the other condition.

Functional Enrichment Analysis

To explore cellular functions and localizations of proteins that were identified and differentially regulated, we performed functional enrichment analysis using the Database for Annotation, Visualization and Integrated Discovery (DAVID) software (Dennis, G. Jr. et al., Genome biology 2003, 4(5), P3). Gene Ontology (GO) terms (Biological Processes and Cellular Compartments) and Kyoto Encyclopedia of Genes and Genomes (KEGG) pathways enriched in all identified proteins and DEPs were selected with P<0.05.

Example 2

Filtration-Based Isolation Protocol

Serum-free conditioned media or human platelet-poor plasma are centrifuged at low speed (2,800 g/10 min) to eliminate cells and cell-debris. In comparison with the ultra-centrifugation based protocol, in which extracellular vesicles (EV) are recovered from the supernatant after centrifugation at 10,000 g/30 min or 100,000 g/60 min, in our new protocol supernatant is filtered at 8,000 g/30 sec using Vivaspin ultrafiltration spin columns. Large oncosomes are recovered form the top of the filter membrane (upper chamber), whereas small EV, are eluted (lower chamber) (FIGS. 10 and 11).

Figure 1G:
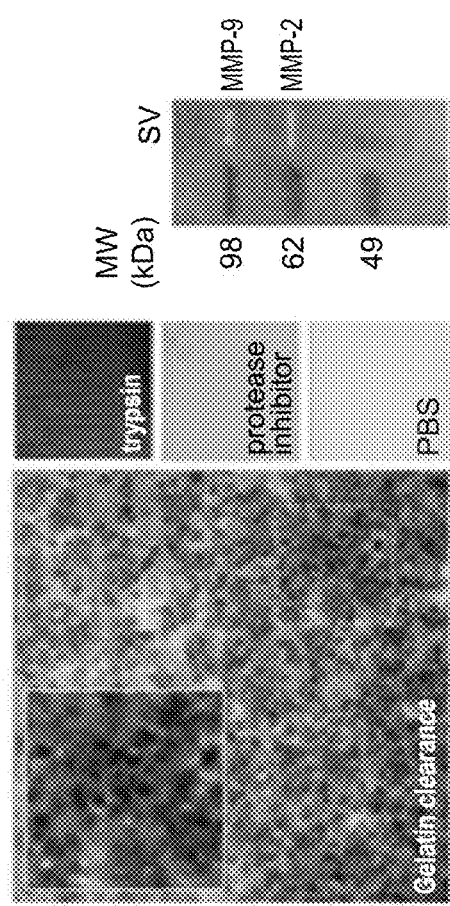
Figure 1H:
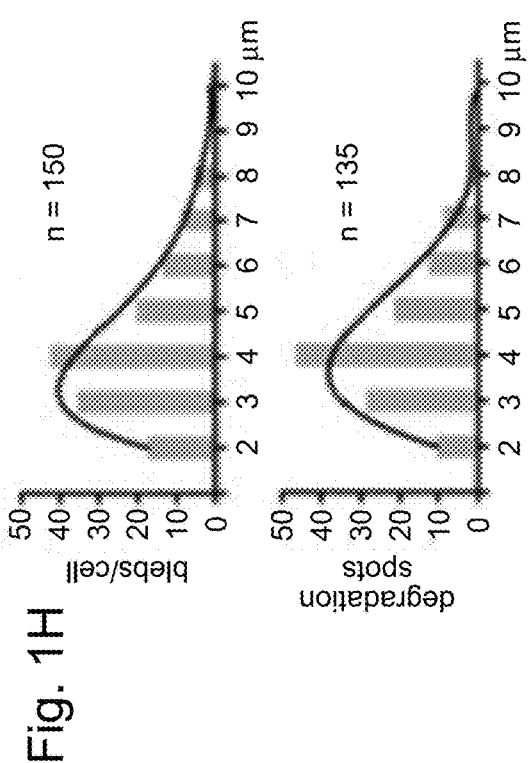

Tumor cells that exhibit the amoeboid feature of membrane blebbing can release large, plasma membrane-derived vesicles into the extracellular space (Di Vizio D et al., Oncosome formation in prostate cancer: association with a region of frequent chromosomal deletion in metastatic disease, Cancer Res 2009, 69:5601-5609) (FIGS. 1A, 1B, 2A). To determine whether these vesicles can be isolated and analyzed, shed vesicles were purified from the conditioned medium of LNCaP human prostate cancer cells stably expressing the potent oncogene MyrAkt1 (Adam R M et al., Cholesterol sensitivity of endogenous and myristoylated Akt, Cancer Res 2007, 67:6238-6246), and from WPMY-1 prostate stromal cells. The contents of the purified vesicles reacted with propidium iodide (PI) (FIG. 7A), consistent with the presence of RNA (FIG. 1C). This allowed detection of a PI-positive vesicle population by fluorescence activated cell sorting (FACS). The stromal cells produced substantially fewer vesicles than LNCaP/MyrAkt1 cells (p<0.001) (FIG. 1D). Biochemical purification coupled with FACS sorting was thus in agreement with results using a visual quantitative bleb-formation assay (Di Vizio D et al., Oncosome formation in prostate cancer: association with a region of frequent chromosomal deletion in metastatic disease, Cancer Res 2009, 69:5601-5609). Shed vesicles from LNCaP/MyrAkt1 cells produced zones of proteolytic clearance in a fluorescent gelatin matrix assay (Ayala I et al., Multiple regulatory inputs converge on cortactin to control invadopodia biogenesis and extracellular matrix degradation, J Cell Sci 2008, 121:369-378) (FIG. 1E) in a similar size range (2-4 µm) and modal distribution to >1 µm diameter membrane blebs observed microscopically (FIGS. 1F, G). MMP zymography showed that the vesicle preparations contained bioactive MMP9 and MMP2, two key proteases involved in tumor cell invasion (FIG. 1E).

Shed vesicles isolated from LNCaP/MyrAkt1 cells contained abundant, membrane-localized MyrAkt1 as demonstrated by FACS and immunofluorescence staining (IF) (FIG. 2A) and by western blotting (FIG. 2B). These results indicated that MyrAkt1 is a potentially useful marker with which to track large shed vesicles produced by LNCaP/MyrAkt1 cells in vivo. Vesicles shed and purified from U87 glioma cells, which exhibit amoeboid properties, contained Caveolin-1 (Cav-1), similar to DU145 prostate cancer cell-derived vesicles (Di Vizio D et al., Oncosome formation in prostate cancer: association with a region of frequent chromosomal deletion in metastatic disease, Cancer Res 2009, 69:5601-5609). DU145- and LNCaP/MyrAkt1 vesicle preparations also contained ARF6 (FIG. 2B), a GTPase shown recently to mediate large microvesicle shedding from tumor cells and to be enriched in TMV (Muralidharan-Chari V. et al., ARF6-regulated shedding of tumor cell-derived plasma membrane microvesicles, Curr Biol 2009, 19:1875-1885). As reported previously (Di Vizio D., et al., Oncosome formation in prostate cancer: association with a region of frequent chromosomal deletion in metastatic disease, Cancer Res 2009, 69:5601-5609), silencing of the GTPase-regulated form in DIAPH3 in DU145 cells potentiated shedding of large microvesicles (FIG. 2B). As reported in another recent study, DIAPH3 loss in DU145 and other tumor cell backgrounds results in amoeboid behavior[10], providing further evidence that shedding of large TMV are a feature of the amoeboid tumor phenotype.

Figure 7G:
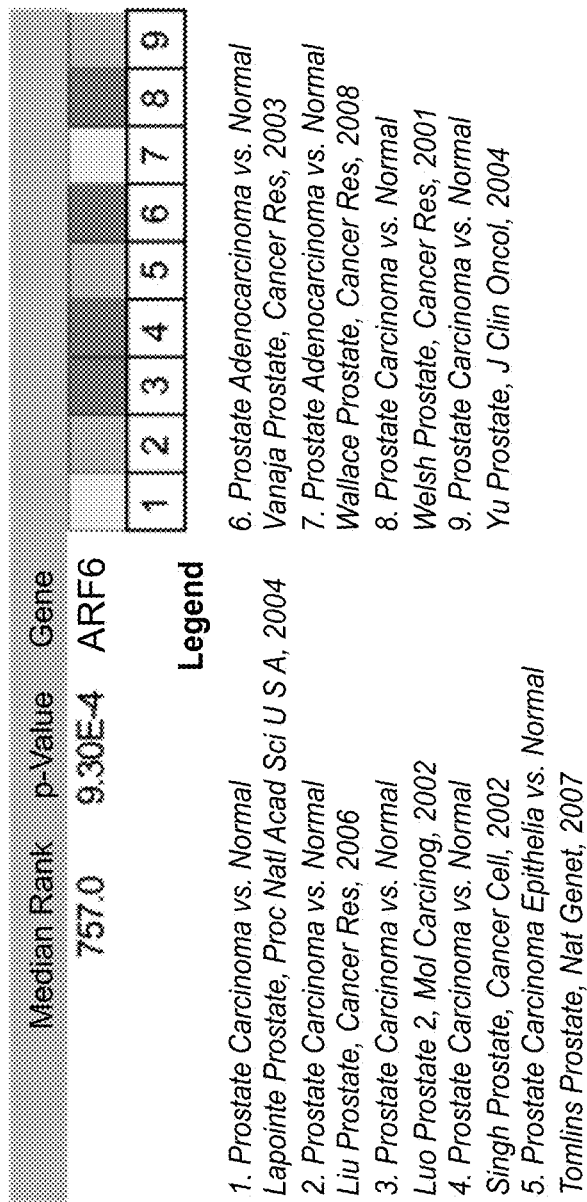

Sustained ARF6 activation enhances tumor cell invasion in cell and animal model systems and vesicle shedding may be a potential mechanism for ARF6-induced acquisition of invasive potential. Interrogation of publicly available prostate cancer expression data sets demonstrated that ARF6 mRNA levels are higher in prostate cancer in comparison with benign tissue (FIG. 7). ARF6 ranked in the top 10 percentile of overexpressed genes in these data sets, and ARF6 mRNA was significantly upregulated in metastases and in recurrent disease.

The MMP activity seen with large vesicles shed from LNCaP/MyrAkt1 cells (FIGS. 1F-H) indicates that they are bioactive. In separate bioactivity tests, these vesicle preparations stimulated migration of mouse tumor endothelial cells (TEC), mouse dermal endothelial cells (MDEC) (Dudley A C et al., Calcification of multipotent prostate tumor endothelium, Cancer Cell 2008, 14:201-211) (FIG. 2C) and DU145 cells (FIG. 2D). LNCaP/MyrAkt1 vesicles also activated WPMY-1 stromal cells to produce factors that stimulated migration of DU145 cells (FIG. 2E). LNCaP/MyrAkt1 vesicles also activated Akt1 in WPMY-1 stromal cells (FIG. 2F). Finally, incubation of mouse prostatic fibroblastic cells with LNCaP/MyrAkt1 vesicles resulted in increased expression of the pro-metastatic factors BDNF, CXCL12, and osteopontin (FIG. 2G). Collectively, these data indicate that LNCaP/MyrAkt1 cells shed oncosomes, including particles considerably larger than nanosized microvesicles, with the potential to contribute to oncogenic signaling by acting as paracrine effectors of inter-tumor cell, tumor cell-endothelial cell, and epithelial-stromal reaction.

Example 3

Large Oncosomes in the Circulation and In Situ

Figure 3B:
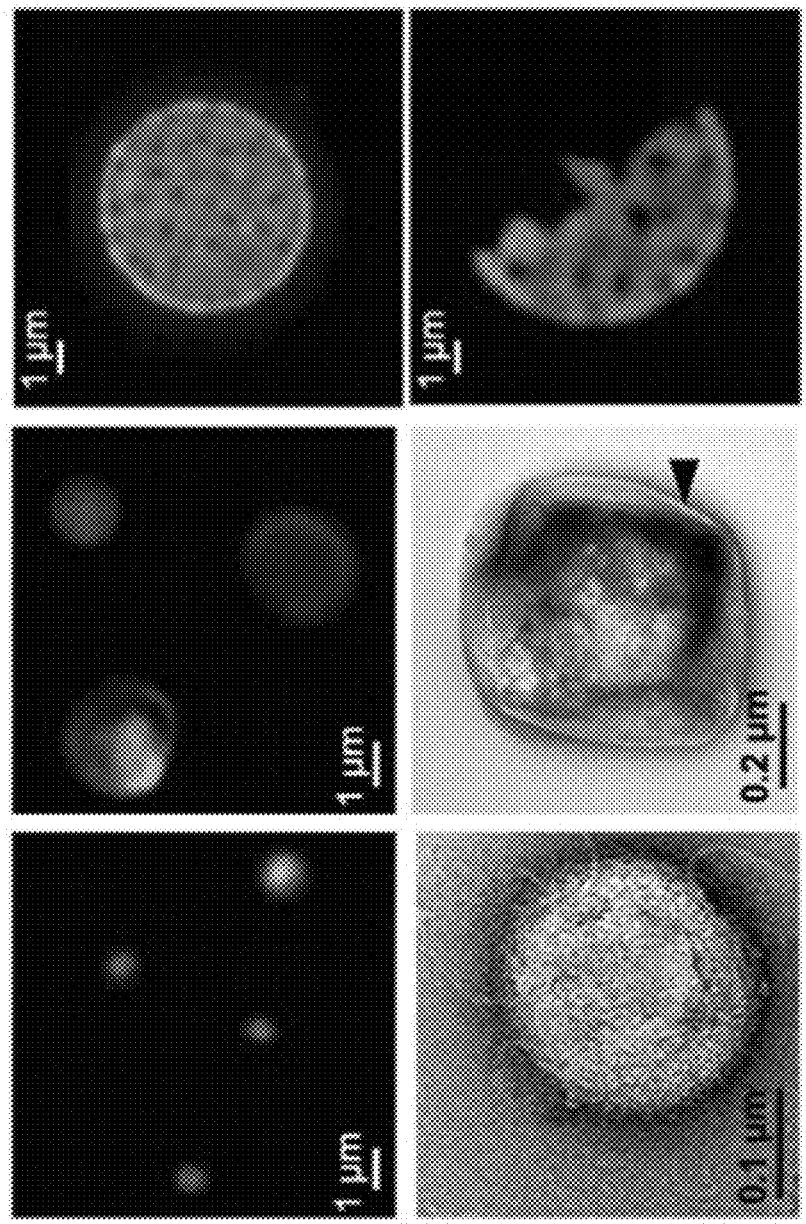

Microvesicles range from about 20 nm to about 10 µm. Exosomes (a type of microvesicles) range from about 20 nm to about 100 nm. Large oncosomes (another type of microvesicles) range in size from about 1 µm to about 10 µm. To distinguish large oncosomes from smaller TMV unequivocally, ultracentrifugation and immuno-flow cytometry were used in combination with sizing beads to create a calibrated domain of analysis based on size. Following biochemical purification, shed vesicles were stained with DAPI to verify the absence of cellular contamination and subsequently labeled with an HA antibody, for detection of membrane-localized MyrAkt1. MyrAkt1-negative and -positive populations were then distinguished on a cell sorter, with gates set using 1 and 10 µm beads (FIG. 3A). Because aggregates may potentially be a significant component of the vesicle preparation, we excluded them from the analysis. To do this, forward scatter signal (FSS) was plotted against pulse width (PW) of the same signal on a linear scale (FIG. 3A). Electronic signal pulses are composed of pulse height (PH) and PW, and the latter is a function of the time necessary to traverse the laser beam, which is shorter for single particles. Electric pulses from a flow cytometer detector with narrow PW identify a singlet (bottom), whereas those with broader PW identify doublets or possibly clumps (top). In order to restrict our analysis to single vesicles, we delineated a region in which only single events were analyzed based on their smaller and more homogeneous PW signals and their corresponding forward scatter signals (FIG. 3A, dotted line). Only these events were gated and considered for further analysis (FIG. 3A, right bottom panel). Electric pulses generated from aggregates, as indicated by increased PW (FIG. 3A, right top panel), were excluded from the analysis, as validated microscopically (FIG. 3A, B).

Sorted single events <1 µm and >1 µm were visualized by both fluorescence and electron microscopy (EM), indicating that large, single vesicles can be distinguished within a mixed population. Microscopic analysis of retrieved vesicles following ultracentrifugation and other sorting procedures indicated that they were not aggregates of smaller particles and they had a definable structure (FIGS. 3A,B). These results indicate that large vesicles can be isolated as discrete events using a tumor cell-specific marker.

Figure 4A:
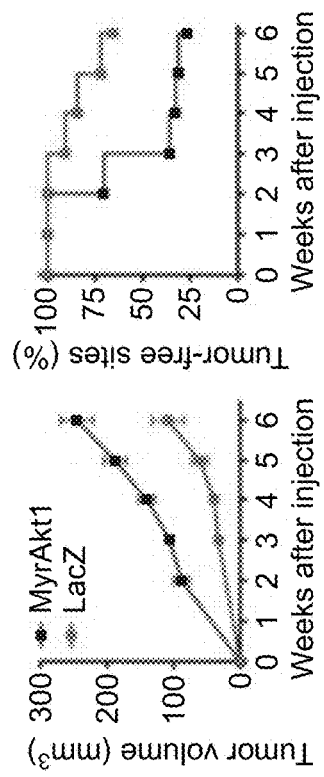
Figure 4B:
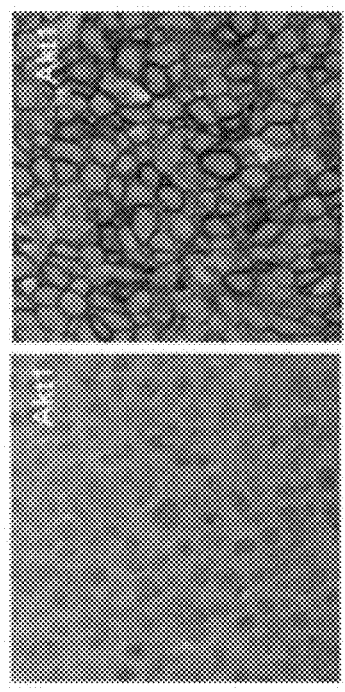
Figure 4C:
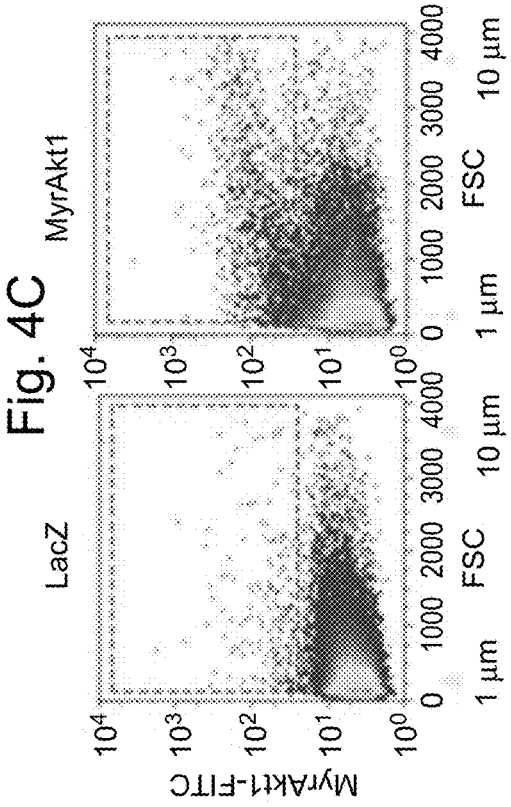
Figure 4D:
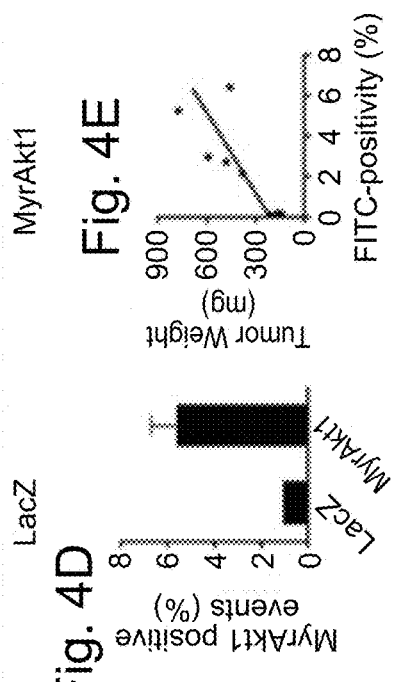
Figure 4E:
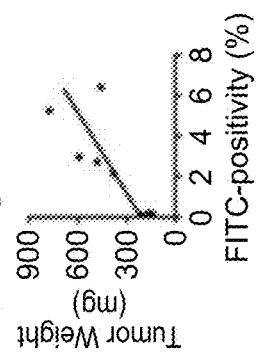

Having demonstrated that membrane blebs shed by cells can be sorted by FACS as discrete large vesicles, a similar approach was used to isolate and quantify these in the circulation of SCID mice carrying LNCaP/MyrAkt1 xenograft tumors. All mice injected subcutaneously with either LNCaP/MyrAkt1 or LNCaP/LacZ control cells in Matrigel developed tumors; however, LNCaP/MyrAkt1 tumors were significantly larger than LNCaP/LacZ tumors (FIG. 4A). Akt1 was membrane localized in LNCaP/MyrAkt1 tumors as detected with both Akt1 and HA antibodies (FIG. 4B). Plasma from mice carrying LNCaP/MyrAkt1 tumors contained MyrAkt1-positive events in the 1-10 µm size range that were sorted with the HA antibody (FIGS. 4C, D). The number of MyrAkt1 events detected by FACS correlated with tumor weight (p<0.01) (FIG. 4e). Because the HA antibody does not recognize an endogenous epitope in the mouse, these data indicate that tumor-derived large vesicles from the subcutaneous xenografts gain access to the circulation.

Figure 4F:
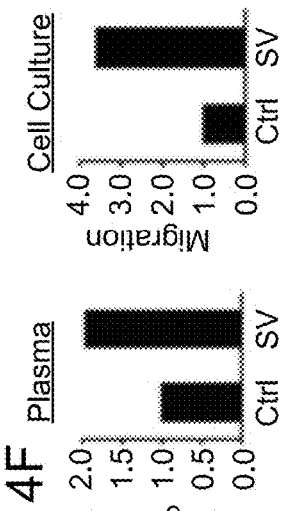

MyrAkt1-positive vesicles isolated from the blood of mice with MyrAkt1 tumors stimulated migration of normal endothelial cells (FIG. 4F, left panel), suggesting the capability of oncosomes in the circulation to evoke progression-related changes in the microvasculature. A similar result was obtained with MyrAkt1-positive vesicles sorted by FACS in the 1-10 µm size range from the medium of LNCaP/MyrAkt1 cells (FIG. 4F, right panel), indicating that large oncosomes are bioactive.

High magnification microscopy of LNCaP/MyrAkt1 tumors revealed membrane vesicles within a similar size range to the large oncosomes identified in vitro and in the circulation of the same animals (FIG. 4G). To our knowledge, this type of membrane vesicle has not been previously described in paraffin sections of prostate tumors. Large oncosome-like structures were evident when sections of LNCaP/MyrAkt1 tumors were stained with hematoxylin and eosin, and immunostained with Akt1 and HA antibodies (FIG. 4G). Morphological features with the appearance of intravasating amoeboid cells were identifiable by immunostaining with Akt1 antibody (FIG. 4G, right panels). Akt1-positive vesicles in tumor tissues were also positive for ARF6, thus resembling large oncosomes secreted from LNCaP/MyrAkt1, and DU145 cells (FIG. 2B), and in accordance with the amoeboid character of these cell lines. Transmission electron microscopy (TEM) of LNCaP/MyrAkt1 tumor sections showed that the tumor cells produced large, bulbous structures with the appearance of membrane sacs, often in the proximity of vascular lacunae (FIG. 4H). Higher magnification revealed internal structures with features resembling polyribosomes. These results suggest that MyrAkt1-positive vesicles detected in the circulation of tumor-bearing mice arise from membrane blebs similar or identical to amoeboid blebs produced in cell culture.

Example 4

Large Oncosome-Like Vesicles as a Feature of Metastatic Prostate Cancer

Identification of similar large vesicles in human prostate cancer specimens was investigated. ARF6 staining revealed vesicular structures in the 1-10 µm size range. Initially a small cohort of human core biopsies (n=15) with localized prostate cancer was examined, and ARF6-positive large oncosome-like structures in the tumor tissue of 3 specimens were identified. Significantly, similar vesicular structures were also identified using a CK18 antibody, which detects prostate luminal epithelial cells (FIG. 5A). To determine whether the identification of ARF6-positive vesicles in tissues may reflect clinical status, a tissue microarray (TMA) containing over 120 punches from foci of localized and metastatic human prostate cancer was examined (Perner S et al., ERG rearrangement metastasis patterns in locally advanced prostate cancer, Urology 2010, 75:762-767). High magnification revealed ARF6-positive vesicles more frequently in foci of Gleason score >7 in comparison with foci of lower Gleason score (p=0.02), suggesting that identification of large oncosome-like structures in situ may indicate tumor progression. Notably, metastatic foci exhibited significantly more vesicles (p=0.001) (FIG. 5B). These characteristics represent a previously unrecognized histologic feature of aggressive prostate cancer.

To determine whether the presence of vesicular structures identified using similar criteria can differentiate indolent vs. fatal cancer, two models of Pten-deficient mice with greatly different biological course were used. $Pten^{PbKO}/Trp53^{PbKO}$ mice develop prostate adenocarcinoma that remains organ-confined within 10-16 weeks after gestation. In comparison, $Pten^{PbKO}/KRAS$ mice develop distant metastases in the liver and lung, and also develop castrate resistance following androgen ablation. ARF6-positive vesicles, similar in appearance and size to those seen in the LNCaP/MyrAkt1 tumors, were abundant in $Pten^{PbKO}/KRAS$ tissues but were absent in the $Pten^{PbKO}/Trp53^{PbKO}$ prostatic tissues. These findings suggest that large oncosome features in prostate tumors may generally report aggressive disease.

Also analyzed was an additional human prostate TMA containing benign samples, organ confined tumors, and metastatic tumors. FIG. 5C shows representative images of absence (left) and presence (right) of large oncosome-like structures detected using anti-ARF6. These features present in less than 30% of the tumors and were not detected in benign prostate tissue. A significant correlation between the presence of large oncosome-like features and metastasis (p=0.0008) was observed. The presence of these features also discriminated between benign and tumor tissue (p<0.0001) (FIG. 5D).

Example 5

Large Oncosomes Containing Caveolin-1 Identify Aggressive Prostate Cancer

Figure 8B:
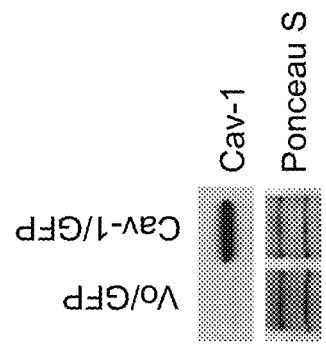
FIG. 8A to FIG. 8D depict, in accordance with an embodiment of the invention the establishment of LNCaP cells overexpessing Cav-1/GFP.
Figure 8A:
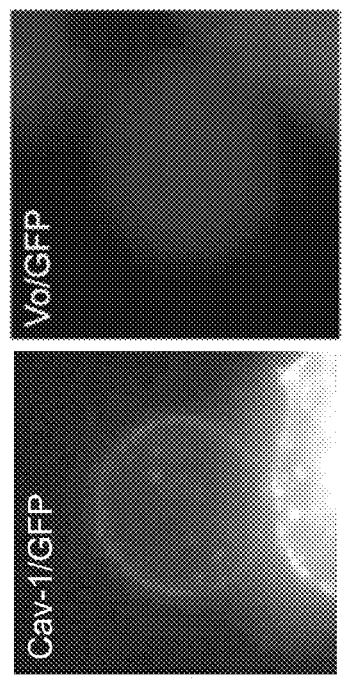
Figure 8D:
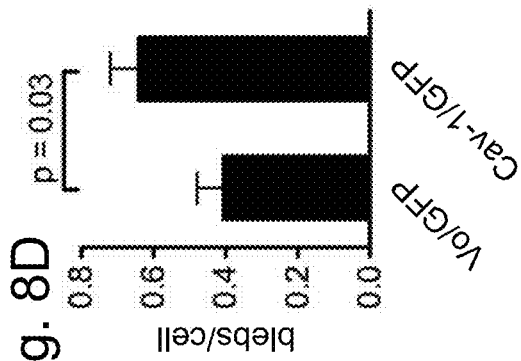
Figure 8C:
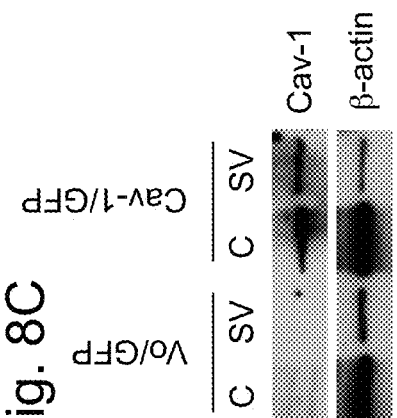
Figure 9A:
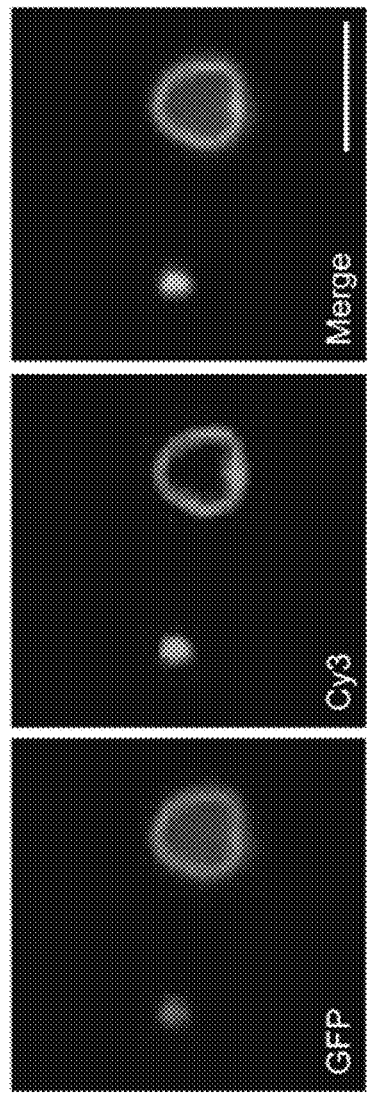
FIG. 9A to FIG. 9B depict in accordance with an embodiment of the invention that particles purified from LNCaP cells overexpressing Cav-1/GFP can be sorted by flow cytometry and visualized by microscopy.
Figure 9B:
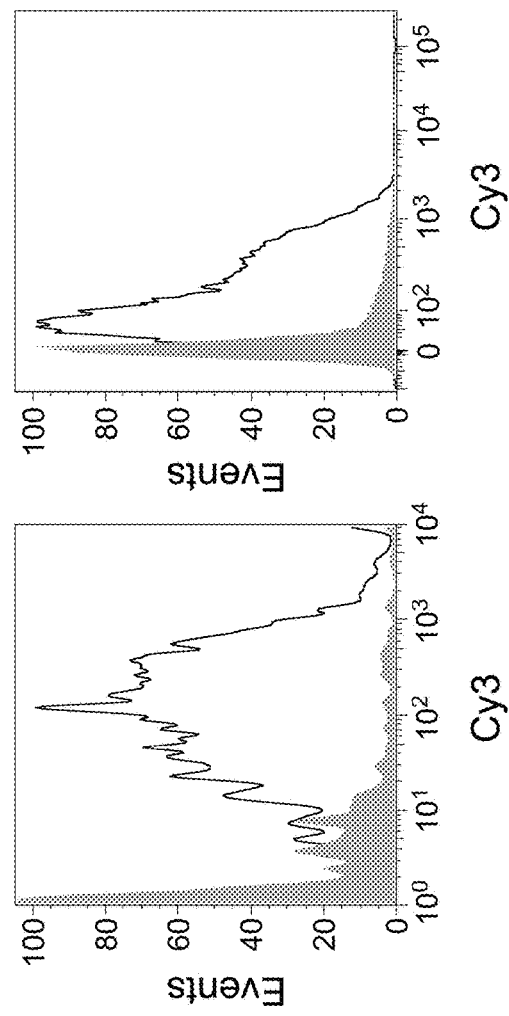

To determine whether large oncosomes can be identified using an endogenous tumor progression marker, large shed vesicles were sorted using Cav-1, a validated prostate cancer biomarker found in the circulation of patients with advanced disease (Tahir S A et al., Secreted caveolin-1 stimulates cell survival/clonal growth and contributes to metastasis in androgen-insensitive prostate cancer, Cancer Res 2001, 61:3882-3885). Cav-1 was present in membrane vesicles produced by DU145 cells, suggesting that large shed vesicles are a mobile vehicle for circulating Cav-1 (FIG. 2B). Cav-1-null LNCaP cells stably expressing Cav-1-GFP produced membrane vesicles that were shed and which contained the fluorescent GFP fusion protein (FIGS. 8A-C). Enforced expression of Cav-1 in LNCaP cells significantly increased the rate of membrane blebbing and shedding (FIG. 8D), suggesting that Cav-1 may play an active role in vesiculation. The ability to sort Cav-1-GFP-positive particles by FACS in the 1-10 µm size range was validated with a Cav-1-Cy3 antibody, which decorated large oncosome-like GFP-positive vesicles (FIG. 9A). Using the same approach, endogenous Cav-1 in shed vesicle preparations from DU145 cells was detected (FIG. 9B). These results suggest that Cav-1 is a viable target for identifying large oncosomes.

Figure 6B:
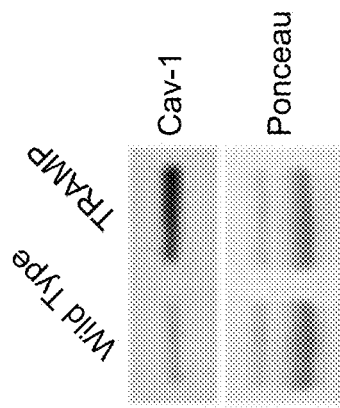
Figure 6A:
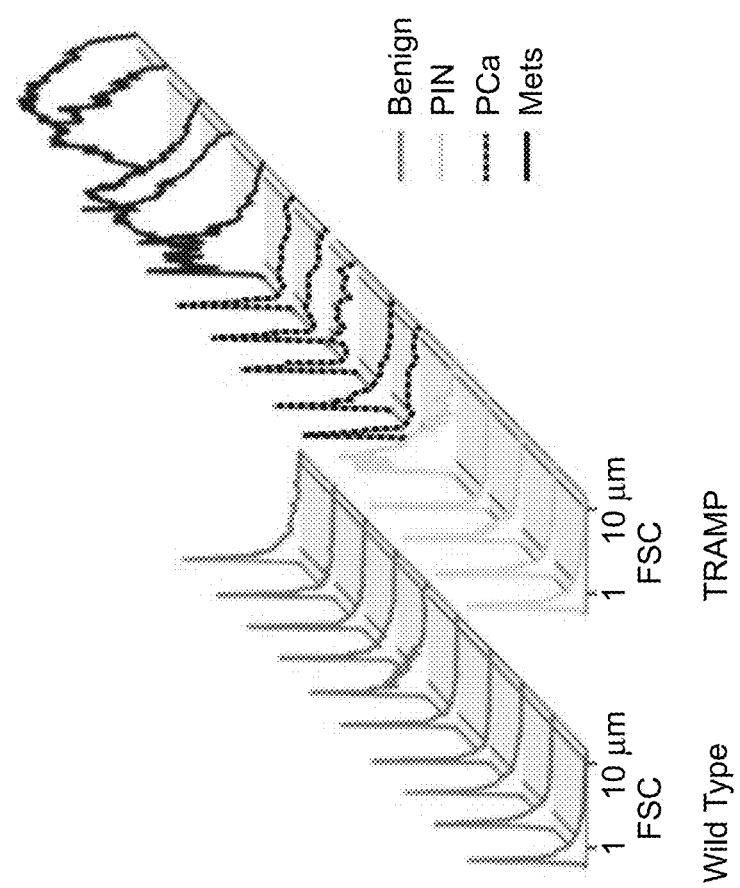

Cav-1-positive vesicles from the plasma of transgenic mice with autochthonous prostate tumors (TRAMP) were sorted. TRAMP prostate tissues express high levels of intra-tumoral Cav-1 (Di Vizio D et al., Caveolin-1 is required for the upregulation of fatty acid synthase (FASN), a tumor promoter, during prostate cancer progression, Cancer Biol Ther 2007, 6:1263-1268; Williams T M et al., Caveolin-1 promotes tumor progression in an autochthonous mouse model of prostate cancer: genetic ablation of Cav-1 delays advanced prostate tumor development in tramp mice, J Biol Chem 2005, 280:25134-25145). Age-matched, non-transgenic littermates were used as controls. Analysis was focused on vesicles of 1-10 µm in diameter. As a validation method, Cav-1-positive vesicles >2-3 µm detected in plasma were sorted by FACS and visualized by direct optical imaging. Vesicles meeting these criteria were detected in plasma from TRAMP mice with prostate cancer, but levels were negligible in plasma of non-transgenic animals and of TRAMP animals with prostate intraepithelial neoplasia (PIN) (FIG. 6A), as confirmed by western blotting (FIG. 6B). These vesicles were substantially more abundant in the circulation of TRAMP mice with lymph node and lung metastases (p=0.03) (FIGS. 6A, C). These results suggest that large oncosomes containing Cav-1 reach the circulation of mice with prostate cancer and their presence can reflect the extent of disease progression. Notably, the presence of Cav-1-positive vesicles <1 µm, which were also detected in the plasma, were not correlated with disease progression in this model (FIG. 6D). Significantly, large oncosome-like vesicles recognized using ARF6 staining were also identified in situ in metastatic TRAMP tumors (FIG. 6E), whereas they were not detected in organ-confined tumors or in benign tissue.

Example 6

In order to understand the degree to which the large oncosomes resemble or are distinct from smaller microvesicles, next generation sequencing (whole genome and RNA-seq) and quantitative proteomics studies (LC-MS/MS SILAC) were performed. The results demonstrated the feasibility of RNA-seq analysis of microvesicles purified from human platelet-poor plasma and have obtained a minimum of 50 million paired end reads per sample. Mapping to RefSeq-annotated human gene loci and quantification as FPKM (fragments per kilobase of exon per million fragments mapped) identified a number of transcripts as differentially expressed between patients with breast cancer and normal subjects (FDR <0.05). Whole genome paired-end sequencing (Illumina) of large oncosome DNA demonstrated that single nucleotide mutations, insertions/deletions, and translocations present in donor cells can be identified in the large oncosome DNA. Stable isotope labeling by amino acids in cell culture (SILAC) profiling of tumor cell-derived large oncosomes in comparison with smaller microvesicles demonstrated enrichment in large oncosomes of cell cycle, anti-apoptosis, and cell motility-associated proteins. Among classes of microvesicle proteins, significant cohorts of the exosome biomarkers were enriched in large oncosomes. These findings identify large oncosomes as a novel class of mircovesicles that harbor clinically relevant biomarkers.

Example 7

LC-MS/MS SILAC Analysis of Large Oncosomes Versus Small EV from Amoeboid Cancer Cells Reveals Specific Oncosome Markers We have previously demonstrated that DIAPH3 silencing induces a rapidly migratory, amoeboid phenotype in prostate cancer cells, which undergo a massive non-apoptotic membrane blebbing. This results in the shedding of atypically large bioactive extracellular vesicles (EV), termed large oncosomes, whose abundance in tumor tissues and in the circulation correlates with tumor aggressiveness. The finding of a correlation of Cav-1 positive large oncosomes with prostate cancer progression in animal models and patients will prostate cancer prompted us to perform a deeper characterization of these vesicles in an attempt to identify a prognostic signature of disease progression.

We performed a robust proteomic analysis of large oncosomes using a quantitative SILAC approach. Of the 400 proteins identified in large oncosomes and 387 proteins identified in small EV, 20 were uniquely attributed to large oncosomes and 7 to small EV, based on identification of each peptide in at least one replicate with more than two sibling peptides, with an FDR <0.05 (FIG. 13). Most of the proteins that were identified exclusively in large oncosomes are involved in metabolic/catabolic processes (i.e. EC11 and PGLS) and in redox processes (i.e. MGST1 and CYB5R3), as demonstrated by GO analysis. Some of the large oncosome proteins have been described as mitochondrial, although most can also shuttle through different subcellular compartments. For example, PHB, while mitochondrial-associated, is also described as a transcription factor with pro-proliferative abilities. Interestingly, PPP2R1A, one of the regulatory subunits of PP2A in mammals, mediate aberrant DNA duplication and aneuploidy. TOP2 is often overexpressed in cancer and has been suggested as a therapeutic target. KIF5B is a microtubule binding protein with motogenic activity, and ANP32A, highly expressed in prostate cancer is involved in proliferation and mRNA trafficking Additional prostate cancer-related targets are CYB5R3, involved in cholesterol synthesis, and RDH11, exhibiting high expression levels in PCa. Given the low number of proteins identified exclusively in the small EV population (n=7), we were not able to perform GO analysis. Interestingly, LAMB2 is involved in cell differentiation, adhesion, migration, GPR126 is a member of the adhesion family of G-protein coupled receptors, ITGA6, another well known adhesion molecule, plays a role in prostate cancer and has been identified as an abundant protein in exosomes.

Figure 12A:
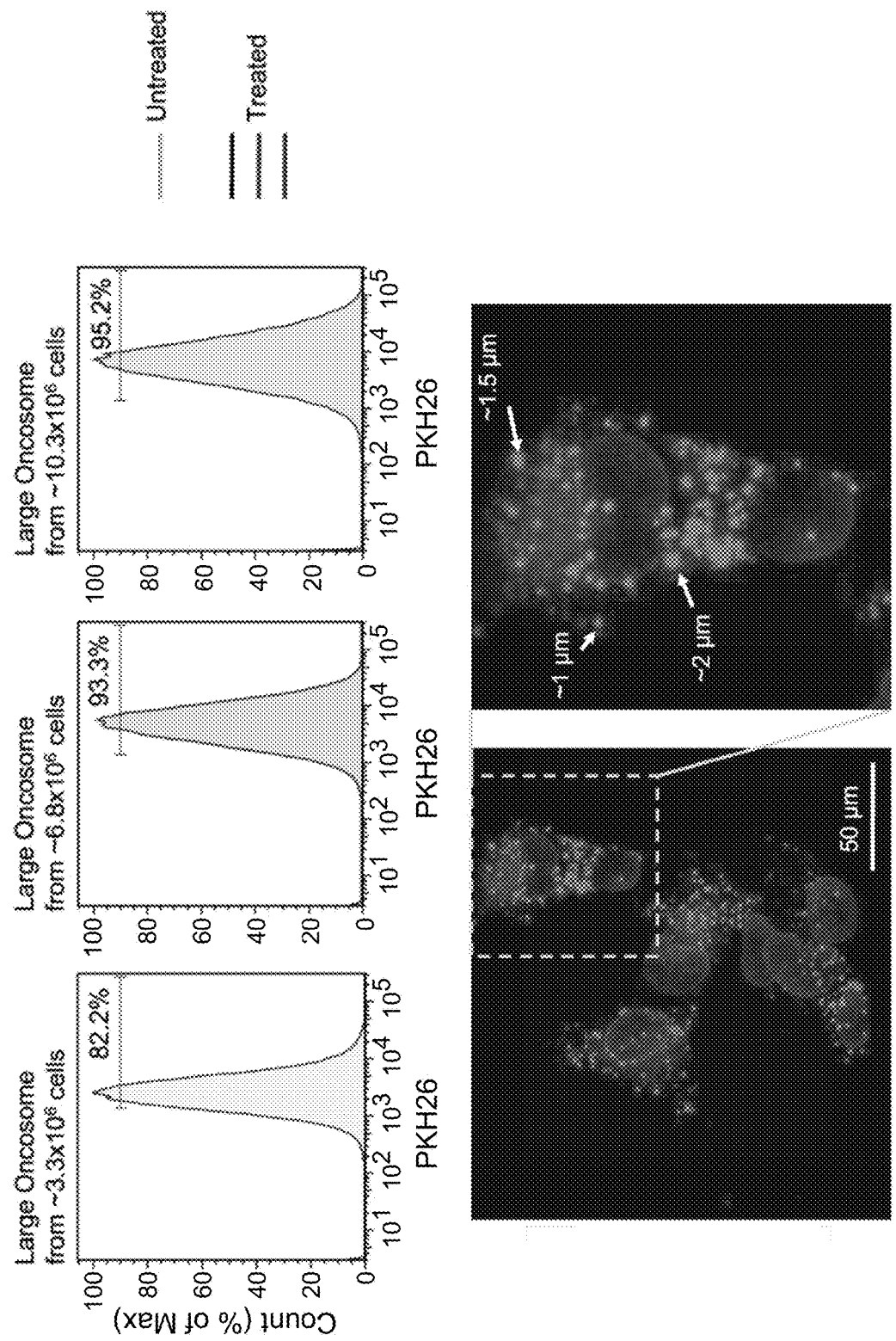

Large oncosomes are internalized by stromal cells (FIG. 12). Large oncosomes isolated from LNCaP MyrAkt1 cells, a prostate cell line overexpressing Myristoilated Akt1, were used for the treatment of WPMY-1, human immortalized fibroblasts. In all the experiments the fibroblasts were treated with large oncosomes for 1 h at 37° C. Top panel of FIG. 12A shows a dose-dependent response to internalization of large oncosomes. The bottom panel of FIG. 12A shows confocal images of sorted fibroblast positive for large oncosome internalization. FIG. 12B shows the follow up of fibroblasts that were sorted after the treatment with large oncosomes. The cells were fixed and imaged by confocal respectively 16 h, 72 h and 7 days after sorting. 3D reconstruction was performed to understand the position of large oncosomes once they enter into the cell and as shown, more large oncosomes are internalized.

Figure 17B:
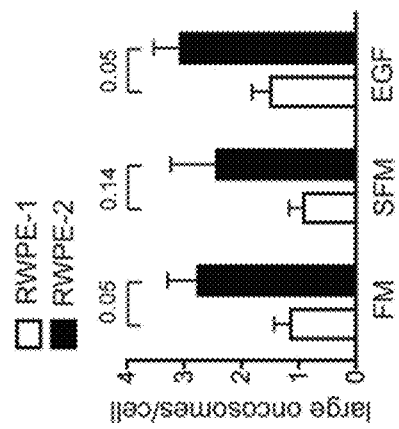
Figure 17A:
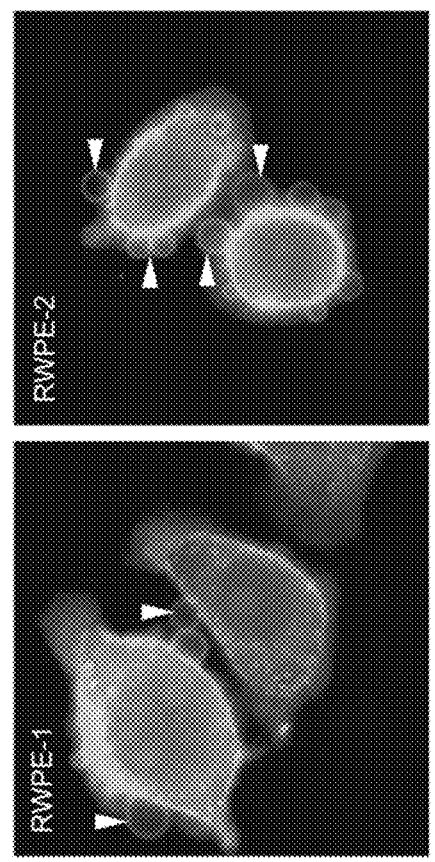

Oncosome formation in CTxB-FITC labeled RWPE-1 and RWPE-2 cells, was quantitatively analysed in presence or absence of full medium (FM), serum free medium (SFM) and EGF. As shown in FIGS. 17A and 17B, cancer cells lines (RWPE-2) form more large oncosomes than non-cancer cell lines (RWPE-1). FIG. 17C depicts the expression levels of 847 miRNAs in cells and extracellular vesicle. Scatter plots data show the correlation between: RWPE-2 versus RWPE-1 cells (R=0.944), EV2 versus EV1 (R=0.895), EV1 versus RWPE-1 cells (R=0.706) and EV2 versus RWPE-2 cells (R=0.649). The difference between EV2 versus RWPE-2 cells and EV1 versus RWPE-1 cells indicate an active selection and secretion of miRNA into EV.

Figure 18A:
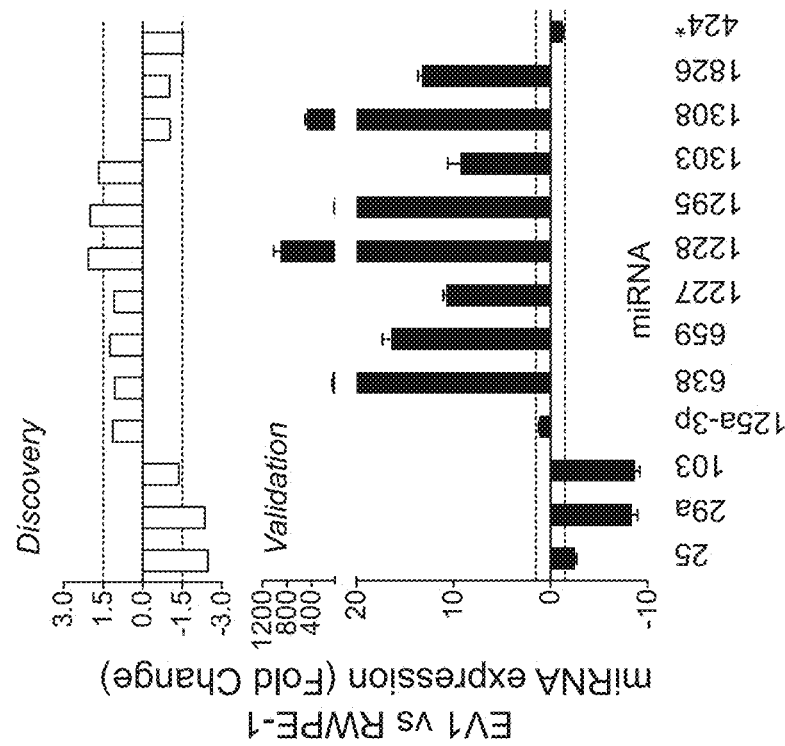
Figure 18B:
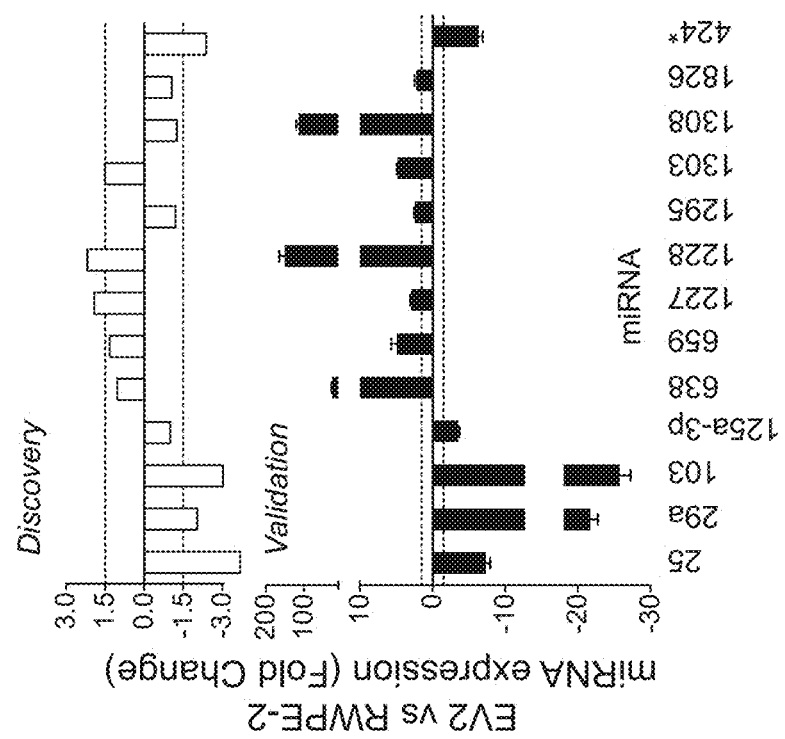

FIG. 18 depicts qRT-PCR validation of the miRNA results using the filtration method, and relative quantitation of miRNAs detected in both EV and donor cells. FIG. 18A shows the TaqMan qRT-PCR levels of miRNAs in EV2 versus RWPE-2 cells. FIG. 18B shows the TaqMan qRT-PCR levels of miRNAs in EV1 versus RWPE-1 cells. FIG. 18C depicts the relative quantitation of the miRNAs with at least 1.5-fold expression change (dotted lines) in EV2 versus RWPE-2 cells (left panel), and in EV1 versus RWPE-1 cells (right panel); boxes at the top show the top 5 expressed miRNAs and boxes at the bottom show the bottom 5 expressed miRNAs.

FIG. 19 shows the quantitation of miR-1227. In FIG. 19(A) qRT-PCR analysis using miR-1227 specific primers was performed on total miRNA isolated from large and small EVs (10 000 and 100 000 g) from RWPE-2 overexpressing miR-1227 mimic. This transient overexpression in cells results in the enrichment of the miRNA in large oncosomes but not in the small EVs. FIG. 19B shows that migration of cancer associated fibroblasts was enhanced by large EVs overexpressing miR-1227.

Large oncosomes, isolated from prostate cancer cell lines, also contain genomic DNA. DNA has been described in exosomes, where it is present in small amounts and largely fragmented. The amount of DNA contained in large oncosomes is more than 30 times of that found in exosomes, whereas the ratio between single and double strand is 5:1 in both. Whole genome paired end sequencing (Illumina HiSeq-2000) of large oncosomes and their donor cells identified, in large oncosomes, 527 out of 5027 indels (insertion, deletion or translocation) present in the donor cells, suggesting that large oncosomes carry about 10% of the genomic alterations present in the donor cell. These results suggest that large oncosomes can be an important source of genomic information about the tumor, in a dynamic manner. For example, large oncosomes from PC3 cells report Myc amplification on chromosome 8 and PTEN deletion on chromosome 10.

As demonstrated herein, large oncosomes represent a distinct population of extracellular vesicles. We can selectively identify specific molecules (such as proteins) carried in large oncosomes which are tumor specific extracellular vesicles. Large oncosomes, identified using specific markers, can be stronger reporters of disease status in the body (plasma). We have a large signature that comprises 20 proteins that are uniquely identified in large oncosomes and over 50 proteins that are significantly enriched in large oncsomes; this provides several markers which may be used as biomarkers in the clinic, and that may be involved in the biogenesis and function of large oncosomes.

Figure 14B:
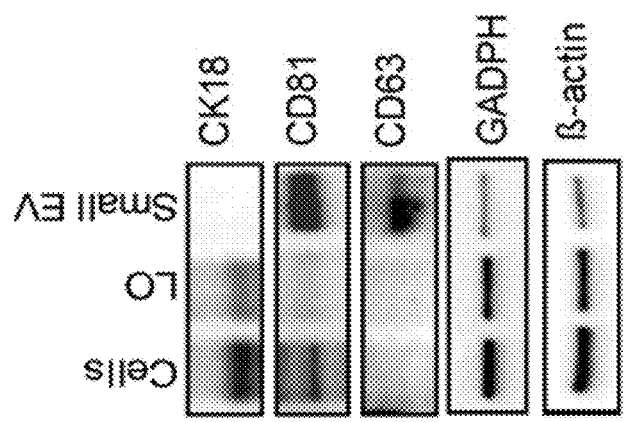
FIG. 14A to FIG. 14B depict, in accordance with an embodiment of the invention, the validation of the proteomics data using immuno-flow cytometry and western blotting.
Figure 14A:
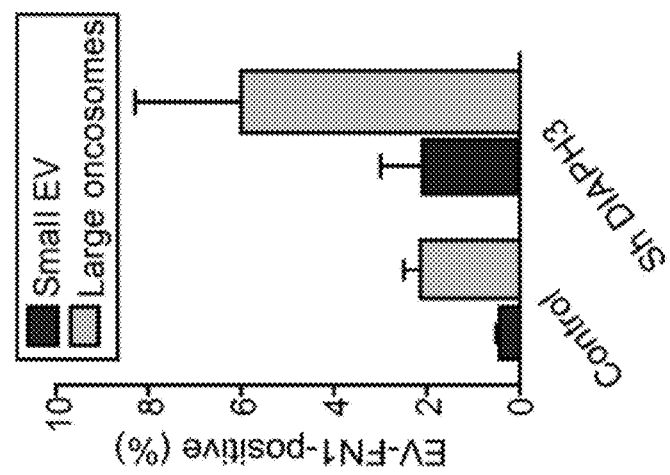

We then focused on additional proteins that were found significantly enriched in one of the two EV populations and identified 57 proteins with a significantly higher SILAC ratio in large oncosomes and 44 proteins with a significantly higher SILAC ratio in small EV (FDR <0.05) (FIG. 16). GPI, LDHB, GOT, FN1 and CK18 were significantly enriched in large oncosomes, whereas the SILAC ratio for CD9, CD81 ITGA3, ITAGV and TGFB1 was higher in small EV. The different roles that these proteins have in the cellular biology suggest a specialized function of the two different vesicles preparation. Enrichment of CK18 and FN1 in large oncosomes and of CD9 and CD81 in small EV was validated by western blotting and flow cytometry (FIG. 14). Importantly, several proteins that were highly enriched in large oncosomes, have been shown to play a functional role in cancer metastasis and response to the therapy (FIG. 15). Interestingly, proteins belonging to categories such as membrane proteins, GTPases, chaperones, and RNA-binding proteins, identified in and frequently considered specific for exosomes, appeared in both EV populations, and occasional were enriched in large oncosomes.

Example 8

This study describes a type of bioactive membrane vesicle previously unrecognized in vivo, which can originate from amoeboid tumor cells. This class of microvesicle is large (~1-10 μm diameter) in comparison to other types of bioactive vesicles (<1 μm), in particular, the substantially smaller exosome-sized vesicles (Duijvesz D et al., Exosomes as biomarker treasure chests for prostate cancer, Eur Urol 2011, 59:823-831) (30-100 nm). Consequently, we propose the term "large oncosome" as a descriptor.

The data herein describes several independent approaches for the detection of large oncosomes in the circulation and in formalin-fixed paraffin embedded (FFPE) sections from mouse models and human tumors. Unlike smaller particles, shown herein is that large oncosome-like structures are visible in tissues using conventional methods, including detection with a clinical biomarker (CK18, FIG. 4D) in FFPE tissue sections, suggesting that a method for detecting these pathologic features could be adapted for routine histopathology. Also described herein is that large oncosomes can be quantified in platelet poor plasma. In several prostate cancer models, as well as in human TMAs and core biopsies, large oncosome-like structures are a feature associated with high Gleason grade and metastatic disease. The results described herein using the LNCaP/MyrAkt1 model, in which the oncosomes can be followed from the point of secretion in tissues to circulation in the blood stream in vivo, support the conclusion that large oncosomes are produced by aggressive tumor cells and gain access to the circulation. The present study focused on prostate cancer models. However, because similar processes occur in other solid tumors, we believe it is likely that similar particles may be detected in other malignancies using comparable approaches.

Using specific markers and a FACS method that allowed sorting of vesicles of 1-10 μm diameter and exclusion of aggregates, the results herein show a correlation between the abundance of large oncosomes in the plasma and tumor weight, in mice carrying LNCaP/MyrAkt1 xenograft tumors. In tissues, large vesicles were detected by direct inspection of H&E-stained tumor sections. ARF6 immunostaining facilitated the detection of similar structures in paraffin-embedded tissue, including in $Pten^{PbKO}$/KRAS metastatic prostate tumors, whereas they were not observed in organ-confined $Pten^{PbKO}$ tumors. $Pten^{PbKO}$/KRAS mice develop resistance to androgen ablation, suggesting that quantification of large oncosome-like features may facilitate assessment of tumor aggressiveness at initial presentation or disease progression during therapy. In TRAMP mice, the abundance of Cav-1-positive circulating large oncosome-like structures was highly associated with the presence of metastatic tumors, and similar vesicular structures were observed in paraffin sections only from advanced tumors (FIG. 6). Notably, the number of smaller events (<1 μm) in the circulation of TRAMP mice did not correlate with disease progression.

Using independent cohorts of human prostate cancer tissues, the findings herein demonstrate that the large oncosome features discriminate between tumor and benign tissue, including benign prostatic hyperplasia (BPH), and also between organ-confined and metastatic tumors. Identifying predictive criteria for prostate tumor progression has been extremely problematic, and current paradigms, including PSA levels, Gleason score and clinical stage, are inadequate as predictive tools. In particular, serum PSA can be elevated in benign conditions such as inflammation and BPH. Collectively, these observations indicate that assessment of large oncosome features in tumor sections or in the circulation may inform clinical evaluation. Identification of proteins other than Cav-1 and ARF6 in oncosomes, as well as discrete RNA species, may result in additional biomarker tools applicable to clinical medicine. Cav-1 is expressed by normal endothelial cells and has been identified as a constituent of circulating nanovesicles. For this reason, it is possible that gating particle size above 1 μm when Cav-1 is used as a sorting marker will provide information about disease course that collection of smaller TMV may not.

Quantitation of circulating tumor cells (CTCs) is currently being evaluated to assess the risk of disease progression for prostate and other types of cancer. However, the clinical significance of CTCs remains to be established because of their extremely small number in peripheral blood as compared with the number of blood cells (Park Y, et al., Expected clinical applications of circulating tumor cells in breast cancer, World J Clin Oncol 2011, 2:303-310). We have demonstrated that large oncosome-like structures can be separated from plasma in a manner that does not require the capture of CTCs or other cells. The molecular characterization of large oncosomes may potentially offer a more sensitive and specific 'liquid biopsy' than CTCs for patient selection, monitoring of treatment efficacy and assessment of drug-resistance.

TABLE 1

Examples of cancer genes

| Gene | Description | Chr | Chr Band | Tumor Types |
|---|---|---|---|---|
| ABL1 | v-abl Abelson murine leukemia viral oncogene homolog 1 | 9 | 9q34.1 | CML, ALL, T-ALL |
| ABL2 | v-abl Abelson murine leukemia viral oncogene homolog 2 | 1 | 1q24-q25 | AML |
| ACSL3 | acyl-CoA synthetase long-chain family member 3 | 2 | 2q36 | prostate |
| AF15Q14 | AF15q14 protein | 15 | 15q14 | AML |
| AF1Q | ALL1-fused gene from chromosome 1q | 1 | 1q21 | ALL |
| AF3p21 | SH3 protein interacting with Nck, 90 kDa (ALL1 fused gene from 3p21) | 3 | 3p21 | ALL |

TABLE 1-continued

Examples of cancer genes

| Gene | Description | Chr | Chr Band | Tumor Types |
|---|---|---|---|---|
| AF5q31 | ALL1 fused gene from 5q31 | 5 | 5q31 | ALL |
| AKAP9 | A kinase (PRKA) anchor protein (yotiao) 9 | 7 | 7q21-q22 | papillary thyroid |
| AKT1 | v-akt murine thymoma viral oncogene homolog 1 | 14 | 14q32.32 | breast, colorectal, ovarian, NSCLC |
| AKT2 | v-akt murine thymoma viral oncogene homolog 2 | 19 | 19q13.1-q13.2 | ovarian, pancreatic |
| ALDH2 | aldehyde dehydrogenase 2 family (mitochondrial) | 12 | 12q24.2 | leiomyoma |
| ALK | anaplastic lymphoma kinase (Ki-1) | 2 | 2p23 | ALCL, NSCLC, neuroblastoma |
| ALO17 | KIAA1618 protein | 17 | 17q25.3 | ALCL |
| APC | adenomatous polyposis of the colon gene | 5 | 5q21 | colorectal, pancreatic, desmoid, hepatoblastoma, glioma, other CNS |
| ARHGEF12 | RHO guanine nucleotide exchange factor (GEF) 12 (LARG) | 11 | 11q23.3 | AML |
| ARHH | RAS homolog gene family, member H (TTF) | 4 | 4p13 | NHL |
| ARID1A | AT rich interactive domain 1A (SWI-like) | 1 | 1p35.3 | clear cell ovarian carcinoma, RCC |
| ARID2 | AT rich interactive domain 2 | 12 | 12q12 | hepatocellular carcinoma |
| ARNT | aryl hydrocarbon receptor nuclear translocator | 1 | 1q21 | AML |
| ASPSCR1 | alveolar soft part sarcoma chromosome region, candidate 1 | 17 | 17q25 | alveolar soft part sarcoma |
| ASXL1 | additional sex combs like 1 | 20 | 20q11.1 | MDS, CMML |
| ATF1 | activating transcription factor 1 | 12 | 12q13 | malignant melanoma of soft parts, angiomatoid fibrous histiocytoma |
| ATIC | 5-aminoimidazole-4-carboxamide ribonucleotide formyltransferase/IMP cyclohydrolase | 2 | 2q35 | ALCL |
| ATM | ataxia telangiectasia mutated | 11 | 11q22.3 | T-PLL |
| ATRX | alpha thalassemia/mental retardation syndrome X-linked | X | Xq21.1 | Pancreatic neuroendocrine tumours, paediatric GBM |
| AXIN1 | axin 1 | 16 | 16p13.3 | colorectal, endometrial, prostate and hepatocellular carcinomas, hepatoblastoma, sporadic medulloblastoma |
| BAP1 | BRCA1 associated protein-1 (ubiquitin carboxy-terminal hydrolase) | 3 | 3p21.31-p21.2 | uveal melanoma, breast, NSCLC, RCC |
| BCL10 | B-cell CLL/lymphoma 10 | 1 | 1p22 | MALT |
| BCL11A | B-cell CLL/lymphoma 11A | 2 | 2p13 | B-CLL |
| BCL11B | B-cell CLL/lymphoma 11B (CTIP2) | 14 | 14q32.1 | T-ALL |
| BCL2 | B-cell CLL/lymphoma 2 | 18 | 18q21.3 | NHL, CLL |
| BCL3 | B-cell CLL/lymphoma 3 | 19 | 19q13 | CLL |
| BCL5 | B-cell CLL/lymphoma 5 | 17 | 17q22 | CLL |
| BCL6 | B-cell CLL/lymphoma 6 | 3 | 3q27 | NHL, CLL |
| BCL7A | B-cell CLL/lymphoma 7A | 12 | 12q24.1 | BNHL |
| BCL9 | B-cell CLL/lymphoma 9 | 1 | 1q21 | B-ALL |
| BCOR | BCL6 corepressor | X | Xp11.4 | retinoblastoma, AML, APL (translocation) |
| BCR | breakpoint cluster region | 22 | 22q11.21 | CML, ALL, AML |
| BHD | folliculin, Birt-Hogg-Dube syndrome | 17 | 17p11.2 | |
| BIRC3 | baculoviral IAP repeat-containing 3 | 11 | 11q22-q23 | MALT |
| BLM | Bloom Syndrome | 15 | 15q26.1 | |
| BMPR1A | bone morphogenetic protein receptor, type IA | 10 | 10q22.3 | |
| BRAF | v-raf murine sarcoma viral oncogene homolog B1 | 7 | 7q34 | melanoma, colorectal, papillary thyroid, borderline ovarian, NSCLC, cholangiocarcinoma, pilocytic astrocytoma |

TABLE 1-continued

Examples of cancer genes

| Gene | Description | Chr | Chr Band | Tumor Types |
|---|---|---|---|---|
| BRCA1 | familial breast/ovarian cancer gene 1 | 17 | 17q21 | ovarian |
| BRCA2 | familial breast/ovarian cancer gene 2 | 13 | 13q12 | breast, ovarian, pancreatic |
| BRD3 | bromodomain containing 3 | 9 | 9q34 | lethal midline carcinoma of young people |
| BRD4 | bromodomain containing 4 | 19 | 19p13.1 | lethal midline carcinoma of young people |
| BRIP1 | BRCA1 interacting protein C-terminal helicase 1 | 17 | 17q22 | |
| BTG1 | B-cell translocation gene 1, anti-proliferative | 12 | 12q22 | BCLL |
| BUB1B | BUB1 budding uninhibited by benzimidazoles 1 homolog beta (yeast) | 15 | 15q15 | |
| C12orf9 | chromosome 12 open reading frame 9 | 12 | 12q14.3 | lipoma |
| C15orf21 | chromosome 15 open reading frame 21 | 15 | 15q21.1 | prostate |
| C15orf55 | chromosome 15 open reading frame 55 | 15 | 15q14 | lethal midline carcinoma |
| C16orf75 | chromosome 16 open reading frame 75 | 16 | 16p13.13 | PMBL, Hodgkin lymphoma |
| C2orf44 | chromosome 2 open reading frame 44 | 2 | 2p23.3 | NSCLC |
| CAMTA1 | calmodulin binding transcription activator 1 | 1 | 1p36.31-p36.23 | epithelioid haemangioendothelioma |
| CANT1 | calcium activated nucleotidase 1 | 17 | 17q25 | prostate |
| CARD11 | caspase recruitment domain family, member 11 | 7 | 7p22 | DLBCL |
| CARS | cysteinyl-tRNA synthetase | 11 | 11p15.5 | ALCL |
| CBFA2T1 | core-binding factor, runt domain, alpha subunit 2; translocated to, 1 (ETO) | 8 | 8q22 | AML |
| CBFA2T3 | core-binding factor, runt domain, alpha subunit 2; translocated to, 3 (MTG-16) | 16 | 16q24 | AML |
| CBFB | core-binding factor, beta subunit | 16 | 16q22 | AML |
| CBL | Cas-Br-M (murine) ecotropic retroviral transforming | 11 | 11q23.3 | AML, JMML, MDS |
| CBLB | Cas-Br-M (murine) ecotropic retroviral transforming sequence b | 3 | 3q13.11 | AML |
| CBLC | Cas-Br-M (murine) ecotropic retroviral transforming sequence c | 19 | 19q13.2 | AML |
| CCDC6 | coiled-coil domain containing 6 | 10 | 10q21 | NSCLC |
| CCNB1IP1 | cyclin B1 interacting protein 1, E3 ubiquitin protein ligase | 14 | 14q11.2 | leiomyoma |
| CCND1 | cyclin D1 | 11 | 11q13 | CLL, B-ALL, breast |
| CCND2 | cyclin D2 | 12 | 12p13 | NHL, CLL |
| CCND3 | cyclin D3 | 6 | 6p21 | MM |
| CCNE1 | cyclin E1 | 19 | 19q12 | serous ovarian |
| CD273 | programmed cell death 1 ligand 2 | 9 | 9p24.2 | PMBL, Hodgkin lymphoma |
| CD274 | CD274 molecule | 9 | 9p24 | PMBL, Hodgkin lymphoma |
| CD74 | CD74 molecule, major histocompatibility complex, class II invariant chain | 5 | 5q32 | NSCLC |
| CD79A | CD79a molecule, immunoglobulin-associated alpha | 19 | 19q13.2 | DLBCL |
| CD79B | CD79b molecule, immunoglobulin-associated beta | 17 | 17q23 | DLBCL |
| CDH1 | cadherin 1, type 1, E-cadherin (epithelial) (ECAD) | 16 | 16q22.1 | lobular breast, gastric |

TABLE 1-continued

Examples of cancer genes

| Gene | Description | Chr | Chr Band | Tumor Types |
|---|---|---|---|---|
| CDH11 | cadherin 11, type 2, OB-cadherin (osteoblast) | 16 | 16q22.1 | aneurysmal bone cyst |
| CDK12 | cyclin-dependent kinase 12 | 17 | 17q12 | serous ovarian |
| CDK4 | cyclin-dependent kinase 4 | 12 | 12q14 | |
| CDK6 | cyclin-dependent kinase 6 | 7 | 7q21-q22 | ALL |
| CDKN2A | cyclin-dependent kinase inhibitor 2A (p16(INK4a)) gene | 9 | 9p21 | melanoma, multiple other tumour types |
| CDKN2a(p14) | cyclin-dependent kinase inhibitor 2A-- p14ARF protein | 9 | 9p21 | melanoma, multiple other tumour types |
| CDKN2C | cyclin-dependent kinase inhibitor 2C (p18, inhibits CDK4) | 1 | 1p32 | glioma, MM |
| CDX2 | caudal type homeo box transcription factor 2 | 13 | 13q12.3 | AML |
| CEBPA | CCAAT/enhancer binding protein (C/EBP), alpha | 19 | 19q13.1 | AML, MDS |
| CEP1 | centrosomal protein 1 | 9 | 9q33 | MPD, NHL |
| CHCHD7 | coiled-coil-helix-coiled-coil-helix domain containing 7 | 8 | 8q11.2 | salivary gland adenoma |
| CHEK2 | CHK2 checkpoint homolog (*S. pombe*) | 22 | 22q12.1 | |
| CHIC2 | cysteine-rich hydrophobic domain 2 | 4 | 4q11-q12 | AML |
| CHN1 | chimerin (chimaerin) 1 | 2 | 2q31-q32.1 | extraskeletal myxoid chondrosarcoma |
| CIC | capicua homolog | 19 | 19q13.2 | oligodendroglioma, soft tissue sarcoma |
| CIITA | class II, major histocompatibility complex, transactivator | 16 | 16p13 | PMBL, Hodgkin lymphoma |
| CLTC | clathrin, heavy polypeptide (Hc) | 17 | 17q11-qter | ALCL, renal |
| CLTCL1 | clathrin, heavy polypeptide-like 1 | 22 | 22q11.21 | ALCL |
| CMKOR1 | chemokine orphan receptor 1 | 2 | 2q37.3 | lipoma |
| CNOT3 | CCR4-NOT transcription complex subunit 3 | 19 | 19q13.4 | T-ALL |
| COL1A1 | collagen, type I, alpha 1 | 17 | 17q21.31-q22 | dermatofibrosarcoma protuberans, aneurysmal bone cyst |
| COPEB | core promoter element binding protein (KLF6) | 10 | 10p15 | prostate, glioma |
| COX6C | cytochrome c oxidase subunit VIc | 8 | 8q22-q23 | uterine leiomyoma |
| CREB1 | cAMP responsive element binding protein 1 | 2 | 2q34 | clear cell sarcoma, angiomatoid fibrous histiocytoma |
| CREB3L1 | cAMP responsive element binding protein 3-like 1 | 11 | 11p11.2 | myxofibrosarcoma |
| CREB3L2 | cAMP responsive element binding protein 3-like 2 | 7 | 7q34 | fibromyxoid sarcoma |
| CREBBP | CREB binding protein (CBP) | 16 | 16p13.3 | ALL, AML, DLBCL, B-NHL |
| CRLF2 | cytokine receptor-like factor 2 | X, Y | Xp22.3; Yp11.3 | B-ALL, Downs associated ALL |
| CRTC3 | CREB regulated transcription coactivator 3 | 15 | 15q26.1 | salivary gland mucoepidermoid |
| CTNNB1 | catenin (cadherin-associated protein), beta 1 | 3 | 3p22-p21.3 | colorectal, ovarian, hepatoblastoma, pleomorphic salivary gland adenoma, other tumour types |
| CYLD | familial cylindromatosis gene | 16 | 16q12-q13 | cylindroma |
| D10S170 | DNA segment on chromosome 10 (unique) 170, H4 gene (PTC1) | 10 | 10q21 | papillary thyroid, CML |
| DAXX | death-domain associated protein | 6 | 6p21.3 | pancreatic neuroendocrine tumour, paediatric glioblastoma |
| DDB2 | damage-specific DNA binding protein 2 | 11 | 11p12 | |
| DDIT3 | DNA-damage-inducible transcript 3 | 12 | 12q13.1-q13.2 | liposarcoma |

TABLE 1-continued

Examples of cancer genes

| Gene | Description | Chr | Chr Band | Tumor Types |
|---|---|---|---|---|
| DDX10 | DEAD (Asp-Glu-Ala-Asp) box polypeptide 10 | 11 | 11q22-q23 | AML* |
| DDX5 | DEAD (Asp-Glu-Ala-Asp) box polypeptide 5 | 17 | 17q21 | prostate |
| DDX6 | DEAD (Asp-Glu-Ala-Asp) box polypeptide 6 | 11 | 11q23.3 | B-NHL |
| DEK | DEK oncogene (DNA binding) | 6 | 6p23 | AML |
| DICER1 | dicer 1, ribonuclease type III | 14 | 14q32.13 | sex cord-stromal tumour, TGCT, embryonal rhabdomyosarcoma |
| DNM2 | dynamin 2 | 19 | 19p13.2 | ETP ALL |
| DNMT3A | DNA (cytosine-5-)-methyltransferase 3 alpha | 2 | 2p23 | AML |
| DUX4 | double homeobox, 4 | 4 | 4q35 | soft tissue sarcoma |
| EBF1 | early B-cell factor 1 | 5 | 5q34 | lipoma |
| ECT2L | epithelial cell transforming sequence 2 oncogene-like | 6 | 6q24.1 | ETP ALL |
| EGFR | epidermal growth factor receptor (erythroblastic leukemia viral (v-erb-b) oncogene homolog, avian) | 7 | 7p12.3-p12.1 | glioma, NSCLC |
| EIF4A2 | eukaryotic translation initiation factor 4A, isoform 2 | 3 | 3q27.3 | NHL |
| ELF4 | E74-like factor 4 (ets domain transcription factor) | X | Xq26 | AML |
| ELK4 | ELK4, ETS-domain protein (SRF accessory protein 1) | 1 | 1q32 | prostate |
| ELKS | ELKS protein | 12 | 12p13.3 | papillary thyroid |
| ELL | ELL gene (11-19 lysine-rich leukemia gene) | 19 | 19p13.1 | AL |
| ELN | elastin | 7 | 7q11.23 | B-ALL |
| EML4 | echinoderm microtubule associated protein like 4 | 2 | 2p21 | NSCLC |
| EP300 | 300 kd E1A-Binding protein gene | 22 | 22q13 | colorectal, breast, pancreatic, AML, ALL, DLBCL |
| EPS15 | epidermal growth factor receptor pathway substrate 15 (AF1p) | 1 | 1p32 | ALL |
| ERBB2 | v-erb-b2 erythroblastic leukemia viral oncogene homolog 2, neuro/glioblastoma derived oncogene homolog (avian) | 17 | 17q21.1 | breast, ovarian, other tumour types, NSCLC, gastric |
| ERCC2 | excision repair cross-complementing rodent repair deficiency, complementation group 2 (xeroderma pigmentosum D) | 19 | 19q13.2-q13.3 | |
| ERCC3 | excision repair cross-complementing rodent repair deficiency, complementation group 3 (xeroderma pigmentosum group B complementing) | 2 | 2q21 | |
| ERCC4 | excision repair cross-complementing rodent repair deficiency, complementation group 4 | 16 | 16p13.3-p13.13 | |
| ERCC5 | excision repair cross-complementing rodent repair deficiency, complementation group 5 (xeroderma pigmentosum, complementation group G (Cockayne syndrome)) | 13 | 13q33 | |
| ERG | v-ets erythroblastosis virus E26 oncogene like (avian) | 21 | 21q22.3 | Ewing sarcoma, prostate, AML |
| ETV1 | ets variant gene 1 | 7 | 7p22 | Ewing sarcoma, prostate |
| ETV4 | ets variant gene 4 (E1A enhancer binding protein, E1AF) | 17 | 17q21 | Ewing sarcoma, prostate carcinoma |

TABLE 1-continued

Examples of cancer genes

| Gene | Description | Chr | Chr Band | Tumor Types |
|---|---|---|---|---|
| ETV5 | ets variant gene 5 | 3 | 3q28 | prostate |
| ETV6 | ets variant gene 6 (TEL oncogene) | 12 | 12p13 | congenital fibrosarcoma, multiple leukaemia and lymphoma, secretory breast, MDS, ALL |
| EVI1 | ecotropic viral integration site 1 | 3 | 3q26 | AML, CML |
| EWSR1 | Ewing sarcoma breakpoint region 1 (EWS) | 22 | 22q12 | Ewing sarcoma, desmoplastic small round cell tumour, ALL, clear cell sarcoma, sarcoma, myoepithelioma |
| EXT1 | multiple exostoses type 1 gene | 8 | 8q24.11-q24.13 | |
| EXT2 | multiple exostoses type 2 gene | 11 | 11p12-p11 | |
| EZH2 | enhancer of zeste homolog 2 | 7 | 7q35-q36 | DLBCL |
| EZR | ezrin | 6 | 6q25.3 | NSCLC |
| FACL6 | fatty-acid-coenzyme A ligase, long-chain 6 | 5 | 5q31 | AML, AEL |
| FAM22A | family with sequence similarity 22, member A | 10 | 10q23.2 | endometrial stromal sarcoma |
| FAM22B | family with sequence similarity 22, member B | 10 | 10q22.3 | endometrial stromal sarcoma |
| FAM46C | family with sequence similarity 46, member C | 1 | 1p12 | MM |
| FANCA | Fanconi anemia, complementation group A | 16 | 16q24.3 | |
| FANCC | Fanconi anemia, complementation group C | 9 | 9q22.3 | |
| FANCD2 | Fanconi anemia, complementation group D2 | 3 | 3p26 | |
| FANCE | Fanconi anemia, complementation group E | 6 | 6p21-p22 | |
| FANCF | Fanconi anemia, complementation group F | 11 | 11p15 | |
| FANCG | Fanconi anemia, complementation group G | 9 | 9p13 | |
| FBXO11 | F-box protein 11 | 2 | 2p16.3 | DLBCL |
| FBXW7 | F-box and WD-40 domain protein 7 (archipelago homolog, *Drosophila*) | 4 | 4q31.3 | colorectal, endometrial, T-ALL |
| FCGR2B | Fc fragment of IgG, low affinity IIb, receptor for (CD32) | 1 | 1q23 | ALL |
| FEV | FEV protein - (HSRNAFEV) | 2 | 2q36 | Ewing sarcoma |
| FGFR1 | fibroblast growth factor receptor 1 | 8 | 8p11.2-p11.1 | MPD, NHL |
| FGFR1OP | FGFR1 oncogene partner (FOP) | 6 | 6q27 | MPD, NHL |
| FGFR2 | fibroblast growth factor receptor 2 | 10 | 10q26 | gastric, NSCLC, endometrial |
| FGFR3 | fibroblast growth factor receptor 3 | 4 | 4p16.3 | bladder, MM, T-cell lymphoma |
| FH | fumarate hydratase | 1 | 1q42.1 | |
| FHIT | fragile histidine triad gene | 3 | 3p14.2 | pleomorphic salivary gland adenoma |
| FIP1L1 | FIP1 like 1 (*S. cerevisiae*) | 4 | 4q12 | idiopathic hypereosinophilic syndrome |
| FLI1 | Friend leukemia virus integration 1 | 11 | 11q24 | Ewing sarcoma |
| FLJ27352 | BX648577, FLJ27352 hypothetical LOC145788 | 15 | 15q21.3 | PMBL, Hodgkin lymphoma |
| FLT3 | fms-related tyrosine kinase 3 | 13 | 13q12 | AML, ALL |
| FNBP1 | formin binding protein 1 (FBP17) | 9 | 9q23 | AML |
| FOXL2 | forkhead box L2 | 3 | 3q23 | granulosa-cell tumour of the ovary |
| FOXO1A | forkhead box O1A (FKHR) | 13 | 13q14.1 | alveolar rhabdomyosarcoma |
| FOXO3A | forkhead box O3A | 6 | 6q21 | AL |
| FOXP1 | forkhead box P1 | 3 | 3p14.1 | ALL |
| FSTL3 | follistatin-like 3 (secreted glycoprotein) | 19 | 19p13 | B-CLL |
| FUBP1 | far upstream element (FUSE) binding protein 1 | 1 | 1p13.1 | oligodendroglioma |

TABLE 1-continued

Examples of cancer genes

| Gene | Description | Chr | Chr Band | Tumor Types |
|---|---|---|---|---|
| FUS | fusion, derived from t(12; 16) malignant liposarcoma | 16 | 16p11.2 | liposarcoma, AML, Ewing sarcoma, angiomatoid fibrous histiocytoma, fibromyxoid sarcoma |
| FVT1 | follicular lymphoma variant translocation 1 | 18 | 18q21.3 | B-NHL |
| GAS7 | growth arrest-specific 7 | 17 | 17p | AML* |
| GATA1 | GATA binding protein 1 (globin transcription factor 1) | X | Xp11.23 | megakaryoblastic leukaemia of Downs syndrome |
| GATA2 | GATA binding protein 2 | 3 | 3q21.3 | AML (CML blast transformation) |
| GATA3 | GATA binding protein 3 | 10 | 10p15 | breast |
| GMPS | guanine monophosphate synthetase | 3 | 3q24 | AML |
| GNA11 | guanine nucleotide binding protein (G protein), alpha 11 (Gq class) | 19 | 19p13.3 | uveal melanoma |
| GNAQ | guanine nucleotide binding protein (G protein), q polypeptide | 9 | 9q21 | uveal melanoma |
| GNAS | guanine nucleotide binding protein (G protein), alpha stimulating activity polypeptide 1 | 20 | 20q13.2 | pituitary adenoma |
| GOLGA5 | golgi autoantigen, golgin subfamily a, 5 (PTC5) | 14 | 14q | papillary thyroid |
| GOPC | golgi associated PDZ and coiled-coil motif containing | 6 | 6q21 | glioblastoma |
| GPC3 | glypican 3 | X | Xq26.1 | |
| GPHN | gephyrin (GPH) | 14 | 14q24 | AL |
| GRAF | GTPase regulator associated with focal adhesion kinase pp125(FAK) | 5 | 5q31 | AML, MDS |
| H3F3A | H3 histone, family 3A | 1 | 1q42.12 | glioma |
| HCMOGT-1 | sperm antigen HCMOGT-1 | 17 | 17p11.2 | JMML |
| HEAB | ATP_GTP binding protein | 11 | 11q12 | AML |
| HERPUD1 | homocysteine-inducible, endoplasmic reticulum stress-inducible, ubiquitin-like domain member 1 | 16 | 16q12.2-q13 | prostate |
| HEY1 | hairy/enhancer-of-split related with YRPW motif 1 | 8 | 8q21 | mesenchymal chondrosarcoma |
| HIP1 | huntingtin interacting protein 1 | 7 | 7q11.23 | CMML |
| HIST1H3B | histone cluster 1, H3b | 6 | 6p22.1 | glioma |
| HIST1H4I | histone 1, H4i (H4FM) | 6 | 6p21.3 | NHL |
| HLF | hepatic leukemia factor | 17 | 17q22 | ALL |
| HLXB9 | homeo box HB9 | 7 | 7q36 | AML |
| HMGA1 | high mobility group AT-hook 1 | 6 | 6p21 | microfollicular thyroid adenoma, various benign mesenchymal tumours |
| HMGA2 | high mobility group AT-hook 2 (HMGIC) | 12 | 12q15 | lipoma, leiomyoma, pleomorphic salivary gland adenoma |
| HNRNPA2B1 | heterogeneous nuclear ribonucleoprotein A2/B1 | 7 | 7p15 | prostate |
| HOOK3 | hook homolog 3 | 8 | 8p11.21 | papillary thyroid |
| HOXA11 | homeo box A11 | 7 | 7p15-p14.2 | CML |
| HOXA13 | homeo box A13 | 7 | 7p15-p14.2 | AML |
| HOXA9 | homeo box A9 | 7 | 7p15-p14.2 | AML* |
| HOXC11 | homeo box C11 | 12 | 12q13.3 | AML |
| HOXC13 | homeo box C13 | 12 | 12q13.3 | AML |
| HOXD11 | homeo box D11 | 2 | 2q31-q32 | AML |
| HOXD13 | homeo box D13 | 2 | 2q31-q32 | AML* |
| HRAS | v-Ha-ras Harvey rat sarcoma viral oncogene homolog | 11 | 11p15.5 | infrequent sarcomas, rare other tumour types |
| HRPT2 | hyperparathyroidism 2 | 1 | 1q21-q31 | parathyroid adenoma |
| HSPCA | heat shock 90 kDa protein 1, alpha | 14 | 14q32.31 | NHL |
| HSPCB | heat shock 90 kDa protein 1, beta | 6 | 6p12 | NHL |

TABLE 1-continued

Examples of cancer genes

| Gene | Description | Chr | Chr Band | Tumor Types |
|---|---|---|---|---|
| IDH1 | isocitrate dehydrogenase 1 (NADP+), soluble | 2 | 2q33.3 | glioblastoma |
| IDH2 | socitrate dehydrogenase 2 (NADP+), mitochondrial | 15 | 15q26.1 | glioblastoma |
| IGH@ | immunoglobulin heavy locus | 14 | 14q32.33 | MM, Burkitt lymphoma, NHL, CLL, B-ALL, MALT, MLCLS |
| IGK@ | immunoglobulin kappa locus | 2 | 2p12 | Burkitt lymphoma, B-NHL |
| IGL@ | immunoglobulin lambda locus | 22 | 22q11.1-q11.2 | Burkitt lymphoma |
| IKZF1 | IKAROS family zinc finger 1 | 7 | 7p12.2 | ALL, DLBCL |
| IL2 | interleukin 2 | 4 | 4q26-q27 | intestinal T-cell lymphoma |
| IL21R | interleukin 21 receptor | 16 | 16p11 | NHL |
| IL6ST | interleukin 6 signal transducer (gp130, oncostatin M receptor) | 5 | 5q11 | hepatocellular carcinoma |
| IL7R | interleukin 7 receptor | 5 | 5p13 | ALL, ETP ALL |
| IRF4 | interferon regulatory factor 4 | 6 | 6p25-p23 | MM |
| IRTA1 | immunoglobulin superfamily receptor translocation associated 1 | 1 | 1q21 | B-NHL |
| ITK | IL2-inducible T-cell kinase | 5 | 5q31-q32 | peripheral T-cell lymphoma |
| JAK1 | Janus kinase 1 | 1 | 1p32.3-p31.3 | ALL |
| JAK2 | Janus kinase 2 | 9 | 9p24 | ALL, AML, MPD, CML |
| JAK3 | Janus kinase 3 | 19 | 19p13.1 | acute megakaryocytic leukaemia, ETP ALL |
| JAZF1 | juxtaposed with another zinc finger gene 1 | 7 | 7p15.2-p15.1 | endometrial stromal tumour |
| JUN | jun oncogene | 1 | 1p32-p31 | sarcoma |
| KCNJ5 | potassium inwardly-rectifying channel, subfamily J, member 5 | 11 | 11q24 | adrenal |
| KDM5A | lysine (K)-specific demethylase 5A, JARID1A | 12 | 12p11 | AML |
| KDM5C | lysine (K)-specific demethylase 5C (JARID1C) | X | Xp11.22-p11.21 | clear cell renal carcinoma |
| KDM6A | lysine (K)-specific demethylase 6A, UTX | X | Xp11.2 | renal, oesophageal SCC, MM |
| KDR | vascular endothelial growth factor receptor 2 | 4 | 4q11-q12 | NSCLC, angiosarcoma |
| KIAA1549 | KIAA1549 | 7 | 7q34 | pilocytic astrocytoma |
| KIF5B | kinesin family member 5B | 10 | 10p11.22 | NSCLC |
| KIT | v-kit Hardy-Zuckerman 4 feline sarcoma viral oncogene homolog | 4 | 4q12 | GIST, AML, TGCT, mastocytosis, mucosal melanoma |
| KLF4 | Kruppel-like factor 4 | 9 | 9q31 | meningioma |
| KLK2 | kallikrein-related peptidase 2 | 19 | 19q13.41 | prostate |
| KRAS | v-Ki-ras2 Kirsten rat sarcoma 2 viral oncogene homolog | 12 | 12p12.1 | pancreatic, colorectal, lung, thyroid, AML, other tumour types |
| KTN1 | kinectin 1 (kinesin receptor) | 14 | 14q22.1 | papillary thyroid |
| LAF4 | lymphoid nuclear protein related to AF4 | 2 | 2q11.2-q12 | ALL, T-ALL |
| LASP1 | LIM and SH3 protein 1 | 17 | 17q11-q21.3 | AML |
| LCK | lymphocyte-specific protein tyrosine kinase | 1 | 1p35-p34.3 | T-ALL |
| LCP1 | lymphocyte cytosolic protein 1 (L-plastin) | 13 | 13q14.1-q14.3 | NHL |
| LCX | leukemia-associated protein with a CXXC domain | 10 | 10q21 | AML |
| LHFP | lipoma HMGIC fusion partner | 13 | 13q12 | lipoma |
| LIFR | leukemia inhibitory factor receptor | 5 | 5p13-p12 | salivary adenoma |
| LMO1 | LIM domain only 1 (rhombotin 1) (RBTN1) | 11 | 11p15 | T-ALL, neuroblastoma |
| LMO2 | LIM domain only 2 (rhombotin-like 1) (RBTN2) | 11 | 11p13 | T-ALL |

TABLE 1-continued

Examples of cancer genes

| Gene | Description | Chr | Chr Band | Tumor Types |
|---|---|---|---|---|
| LPP | LIM domain containing preferred translocation partner in lipoma | 3 | 3q28 | lipoma, leukaemia |
| LRIG3 | leucine-rich repeats and immunoglobulin-like domains 3 | 12 | 12q14.1 | NSCLC |
| LYL1 | lymphoblastic leukemia derived sequence 1 | 19 | 19p13.2-p13.1 | T-ALL |
| MADH4 | Homolog of *Drosophila* Mothers Against Decapentaplegic 4 gene | 18 | 18q21.1 | colorectal, pancreatic, small intestine |
| MAF | v-maf musculoaponeurotic fibrosarcoma oncogene homolog | 16 | 16q22-q23 | MM |
| MAFB | v-maf musculoaponeurotic fibrosarcoma oncogene homolog B (avian) | 20 | 20q11.2-q13.1 | MM |
| MALT1 | mucosa associated lymphoid tissue lymphoma translocation gene 1 | 18 | 18q21 | MALT |
| MAML2 | mastermind-like 2 (*Drosophila*) | 11 | 11q22-q23 | salivary gland mucoepidermoid |
| MAP2K1 | mitogen-activated protein kinase kinase 1 | 15 | 15q22.1-q22.33 | NSCLC, melanoma, colorectal |
| MAP2K2 | mitogen-activated protein kinase kinase 2 | 19 | 19p13.3 | NSCLC, melanoma |
| MAP2K4 | mitogen-activated protein kinase kinase 4 | 17 | 17p11.2 | pancreatic, breast, colorectal |
| MAX | Myc associated factor X | 14 | 14q23 | pheochromocytoma |
| MDM2 | Mdm2 p53 binding protein homolog | 12 | 12q15 | sarcoma, glioma, colorectal, other tumour types |
| MDM4 | Mdm4 p53 binding protein homolog | 1 | 1q32 | glioblastoma, bladder, retinoblastoma |
| MDS1 | myelodysplasia syndrome 1 | 3 | 3q26 | MDS, AML |
| MDS2 | myelodysplastic syndrome 2 | 1 | 1p36 | MDS |
| MECT1 | mucoepidermoid translocated 1 | 19 | 19p13 | salivary gland mucoepidermoid |
| MED12 | mediator complex subunit 12 | X | Xq13 | uterine leiomyoma |
| MEN1 | multiple endocrine neoplasia type 1 gene | 11 | 11q13 | parathyroid tumours, pancreatic neuroendocrine tumour |
| MET | met proto-oncogene (hepatocyte growth factor receptor) | 7 | 7q31 | papillary renal, head-neck squamous cell |
| MITF | microphthalmia-associated transcription factor | 3 | 3p14.1 | melanoma |
| MKL1 | megakaryoblastic leukemia (translocation) 1 | 22 | 22q13 | acute megakaryocytic leukaemia |
| MLF1 | myeloid leukemia factor 1 | 3 | 3q25.1 | AML |
| MLH1 | *E. coli* MutL homolog gene | 3 | 3p21.3 | colorectal, endometrial, ovarian, CNS |
| MLL | myeloid/lymphoid or mixed-lineage leukemia (trithorax homolog, *Drosophila*) | 11 | 11q23 | AML, ALL |
| MLL2 | myeloid/lymphoid or mixed-lineage leukemia 2 | 12 | 12q12-q14 | medulloblastoma, renal |
| MLL3 | myeloid/lymphoid or mixed-lineage leukemia 3 | 7 | 7q36.1 | medulloblastoma |
| MLLT1 | myeloid/lymphoid or mixed-lineage leukemia (trithorax homolog, *Drosophila*); translocated to, 1 (ENL) | 19 | 19p13.3 | AL |
| MLLT10 | myeloid/lymphoid or mixed-lineage leukemia (trithorax homolog, *Drosophila*); translocated to, 10 (AF10) | 10 | 10p12 | AL |
| MLLT2 | myeloid/lymphoid or mixed-lineage leukemia (trithorax homolog, *Drosophila*); translocated to, 2 (AF4) | 4 | 4q21 | AL |

TABLE 1-continued

Examples of cancer genes

| Gene | Description | Chr | Chr Band | Tumor Types |
|---|---|---|---|---|
| MLLT3 | myeloid/lymphoid or mixed-lineage leukemia (trithorax homolog, *Drosophila*); translocated to, 3 (AF9) | 9 | 9p22 | ALL |
| MLLT4 | myeloid/lymphoid or mixed-lineage leukemia (trithorax homolog, *Drosophila*); translocated to, 4 (AF6) | 6 | 6q27 | AL |
| MLLT6 | myeloid/lymphoid or mixed-lineage leukemia (trithorax homolog, *Drosophila*); translocated to, 6 (AF17) | 17 | 17q21 | AL |
| MLLT7 | myeloid/lymphoid or mixed-lineage leukemia (trithorax homolog, *Drosophila*); translocated to, 7 (AFX1) | X | Xq13.1 | AL |
| MN1 | meningioma (disrupted in balanced translocation) 1 | 22 | 22q13 | AML, meningioma |
| MPL | myeloproliferative leukemia virus oncogene, thrombopoietin receptor | 1 | p34 | MPD |
| MSF | MLL septin-like fusion | 17 | 17q25 | AML* |
| MSH2 | mutS homolog 2 (*E. coli*) | 2 | 2p22-p21 | colorectal, endometrial, ovarian |
| MSH6 | mutS homolog 6 (*E. coli*) | 2 | 2p16 | colorectal |
| MSI2 | musashi homolog 2 (*Drosophila*) | 17 | 17q23.2 | CML |
| MSN | moesin | X | Xq11.2-q12 | ALCL |
| MTCP1 | mature T-cell proliferation 1 | X | Xq28 | T cell prolymphocytic leukaemia |
| MUC1 | mucin 1, transmembrane | 1 | 1q21 | B-NHL |
| MUTYH | mutY homolog (*E. coli*) | 1 | 1p34.3-1p32.1 | |
| MYB | v-myb myeloblastosis viral oncogene homolog | 6 | 6q22-23 | adenoid cystic carcinoma |
| MYC | v-myc myelocytomatosis viral oncogene homolog (avian) | 8 | 8q24.12-q24.13 | Burkitt lymphoma, amplified in other cancers, B-CLL |
| MYCL1 | v-myc myelocytomatosis viral oncogene homolog 1, lung carcinoma derived (avian) | 1 | 1p34.3 | small cell lung carcinoma |
| MYCN | v-myc myelocytomatosis viral related oncogene, neuroblastoma derived (avian) | 2 | 2p24.1 | neuroblastoma |
| MYD88 | myeloid differentiation primary response gene (88) | 3 | 3p22 | ABC-DLBCL |
| MYH11 | myosin, heavy polypeptide 11, smooth muscle | 16 | 16p13.13-p13.12 | AML |
| MYH9 | myosin, heavy polypeptide 9, non-muscle | 22 | 22q13.1 | ALCL |
| MYST4 | MYST histone acetyltransferase (monocytic leukemia) 4 (MORF) | 10 | 10q22 | AML |
| NACA | nascent-polypeptide-associated complex alpha polypeptide | 12 | 12q23-q24.1 | NHL |
| NBS1 | Nijmegen breakage syndrome 1 (nibrin) | 8 | 8q21 | |
| NCOA1 | nuclear receptor coactivator 1 | 2 | 2p23 | alveolar rhabdomyosarcoma |
| NCOA2 | nuclear receptor coactivator 2 (TIF2) | 8 | 8q13.1 | AML, chondrosarcoma |
| NCOA4 | nuclear receptor coactivator 4 - PTC3 (ELE1) | 10 | 10q11.2 | papillary thyroid |
| NDRG1 | N-myc downstream regulated 1 | 8 | 8q24.3 | prostate |
| NF1 | neurofibromatosis type 1 gene | 17 | 17q12 | neurofibroma, glioma |

TABLE 1-continued

Examples of cancer genes

| Gene | Description | Chr | Chr Band | Tumor Types |
|---|---|---|---|---|
| NF2 | neurofibromatosis type 2 gene | 22 | 22q12.2 | meningioma, acoustic neuroma, renal |
| NFE2L2 | nuclear factor (erythroid-derived 2)-like 2 (NRF2) | 2 | 2q31 | NSCLC, HNSCC |
| NFIB | nuclear factor I/B | 9 | 9p24.1 | adenoid cystic carcinoma, lipoma |
| NFKB2 | nuclear factor of kappa light polypeptide gene enhancer in B-cells 2 (p49/p100) | 10 | 10q24 | B-NHL |
| NIN | ninein (GSK3B interacting protein) | 14 | 14q24 | MPD |
| NKX2-1 | NK2 homeobox 1 | 14 | 14q13 | NSCLC |
| NONO | non-POU domain containing, octamer-binding | X | Xq13.1 | papillary renal |
| NOTCH1 | Notch homolog 1, translocation-associated (*Drosophila*) (TAN1) | 9 | 9q34.3 | T-ALL |
| NOTCH2 | Notch homolog 2 | 1 | 1p13-p11 | marginal zone lymphoma, DLBCL |
| NPM1 | nucleophosmin (nucleolar phosphoprotein B23, numatrin) | 5 | 5q35 | NHL, APL, AML |
| NR4A3 | nuclear receptor subfamily 4, group A, member 3 (NOR1) | 9 | 9q22 | extraskeletal myxoid chondrosarcoma |
| NRAS | neuroblastoma RAS viral (v-ras) oncogene homolog | 1 | 1p13.2 | melanoma, MM, AML, thyroid |
| NSD1 | nuclear receptor binding SET domain protein 1 | 5 | 5q35 | AML |
| NT5C2 | 5'-nucleotidase, cytosolic II | 10 | 10q24.32 | relapse ALL |
| NTRK1 | neurotrophic tyrosine kinase, receptor, type 1 | 1 | 1q21-q22 | papillary thyroid |
| NTRK3 | neurotrophic tyrosine kinase, receptor, type 3 | 15 | 15q25 | congenital fibrosarcoma, secretory breast |
| NUMA1 | nuclear mitotic apparatus protein 1 | 11 | 11q13 | APL |
| NUP214 | nucleoporin 214 kDa (CAN) | 9 | 9q34.1 | AML, T-ALL |
| NUP98 | nucleoporin 98 kDa | 11 | 11p15 | AML |
| OLIG2 | oligodendrocyte lineage transcription factor 2 (BHLHB1) | 21 | 21q22.11 | T-ALL |
| OMD | osteomodulin | 9 | 9q22.31 | aneurysmal bone cyst |
| P2RY8 | purinergic receptor P2Y, G-protein coupled, 8 | X, Y | Xp22.3; Yp11.3 | B-ALL, Down syndrome associated ALL |
| PAFAH1B2 | platelet-activating factor acetylhydrolase, isoform Ib, beta subunit 30 kDa | 11 | 11q23 | MLCLS |
| PALB2 | partner and localizer of BRCA2 | 16 | 16p12.1 | |
| PAX3 | paired box gene 3 | 2 | 2q35 | alveolar rhabdomyosarcoma |
| PAX5 | paired box gene 5 (B-cell lineage specific activator protein) | 9 | 9p13 | NHL, ALL, B-ALL |
| PAX7 | paired box gene 7 | 1 | 1p36.2-p36.12 | alveolar rhabdomyosarcoma |
| PAX8 | paired box gene 8 | 2 | 2q12-q14 | follicular thyroid |
| PBRM1 | polybromo 1 | 3 | 3p21 | clear cell renal carcinoma, breast |
| PBX1 | pre-B-cell leukemia transcription factor 1 | 1 | 1q23 | pre B-ALL, myoepithelioma |
| PCM1 | pericentriolar material 1 (PTC4) | 8 | 8p22-p21.3 | papillary thyroid, CML, MPD |
| PCSK7 | proprotein convertase subtilisin/kexin type 7 | 11 | 11q23.3 | MLCLS |
| PDE4DIP | phosphodiesterase 4D interacting protein (myomegalin) | 1 | 1q12 | MPD |
| PDGFB | platelet-derived growth factor beta polypeptide (simian sarcoma viral (v-sis) oncogene homolog) | 22 | 22q12.3-q13.1 | DFSP |
| PDGFRA | platelet-derived growth factor, alpha-receptor | 4 | 4q11-q13 | GIST, idiopathic hypereosinophilic syndrome, paediatric glioblastoma |

TABLE 1-continued

Examples of cancer genes

| Gene | Description | Chr | Chr Band | Tumor Types |
|---|---|---|---|---|
| PDGFRB | platelet-derived growth factor receptor, beta polypeptide | 5 | 5q31-q32 | MPD, AML, CMML, CML |
| PER1 | period homolog 1 (Drosophila) | 17 | 17p13.1-17p12 | AML, CMML |
| PHF6 | PHD finger protein 6 | X | Xq26.3 | ETP ALL |
| PHOX2B | paired-like homeobox 2b | 4 | 4p12 | neuroblastoma |
| PICALM | phosphatidylinositol binding clathrin assembly protein (CALM) | 11 | 11q14 | TALL, AML, |
| PIK3CA | phosphoinositide-3-kinase, catalytic, alpha polypeptide | 3 | 3q26.3 | colorectal, gastric, glioblastoma, breast |
| PIK3R1 | phosphoinositide-3-kinase, regulatory subunit 1 (alpha) | 5 | 5q13.1 | glioblastoma, ovarian, colorectal |
| PIM1 | pim-1 oncogene | 6 | 6p21.2 | NHL |
| PLAG1 | pleiomorphic adenoma gene 1 | 8 | 8q12 | salivary adenoma |
| PML | promyelocytic leukemia | 15 | 15q22 | APL, ALL |
| PMS1 | PMS1 postmeiotic segregation increased 1 (S. cerevisiae) | 2 | 2q31-q33 | |
| PMS2 | PMS2 postmeiotic segregation increased 2 (S. cerevisiae) | 7 | 7p22 | |
| PMX1 | paired mesoderm homeo box 1 | 1 | 1q24 | AML |
| PNUTL1 | peanut-like 1 (Drosophila) | 22 | 22q11.2 | AML |
| POT1 | protection of telomeres 1 | 7 | 7q31.33 | CLL |
| POU2AF1 | POU domain, class 2, associating factor 1 (OBF1) | 11 | 11q23.1 | NHL |
| POU5F1 | POU domain, class 5, transcription factor 1 | 6 | 6p21.31 | sarcoma |
| PPARG | peroxisome proliferative activated receptor, gamma | 3 | 3p25 | follicular thyroid |
| PPP2R1A | protein phosphatase 2, regulatory subunit A, alpha | 19 | 19q13.41 | clear cell ovarian carcinoma |
| PRCC | papillary renal cell carcinoma (translocation-associated) | 1 | 1q21.1 | papillary renal |
| PRDM1 | PR domain containing 1, with ZNF domain | 6 | 6q21 | DLBCL |
| PRDM16 | PR domain containing 16 | 1 | 1p36.23-p33 | MDS, AML |
| PRF1 | perforin 1 (pore forming protein) | 10 | 10q22 | |
| PRKAR1A | protein kinase, cAMP-dependent, regulatory, type I, alpha (tissue specific extinguisher 1) | 17 | 17q23-q24 | papillary thyroid |
| PRO1073 | PRO1073 protein (ALPHA) | 11 | 11q31.1 | renal cell carcinoma (childhood epithelioid) |
| PSIP2 | PC4 and SFRS1 interacting protein 2 (LEDGF) | 9 | 9p22.2 | AML |
| PTCH | Homolog of Drosophila Patched gene | 9 | 9q22.3 | skin basal cell, medulloblastoma |
| PTEN | phosphatase and tensin homolog gene | 10 | 10q23.3 | glioma, prostate, endometrial |
| PTPN11 | protein tyrosine phosphatase, non-receptor type 11 | 12 | 12q24.1 | JMML, AML, MDS |
| RAB5EP | rabaptin, RAB GTPase binding effector protein 1 (RABPT5) | 17 | 17p13 | CMML |
| RAC1 | ras-related C3 botulinum toxin substrate 1 (rho family, small GTP binding protein Rac1) | 7 | 7p22 | melanoma |
| RAD51L1 | RAD51-like 1 (S. cerevisiae) (RAD51B) | 14 | 14q23-q24.2 | lipoma, uterine leiomyoma |
| RAF1 | v-raf-1 murine leukemia viral oncogene homolog 1 | 3 | 3p25 | pilocytic astrocytoma |
| RALGDS | ral guanine nucleotide dissociation stimulator | 9 | 9q34.3 | PMBL, Hodgkin lymphoma, |
| RANBP17 | RAN binding protein 17 | 5 | 5q34 | ALL |
| RAP1GDS1 | RAP1, GTP-GDP dissociation stimulator 1 | 4 | 4q21-q25 | T-ALL |

TABLE 1-continued

Examples of cancer genes

| Gene | Description | Chr | Chr Band | Tumor Types |
|---|---|---|---|---|
| RARA | retinoic acid receptor, alpha | 17 | 17q12 | APL |
| RB1 | retinoblastoma gene | 13 | 13q14 | retinoblastoma, sarcoma, breast, small cell lung carcinoma |
| RBM15 | RNA binding motif protein 15 | 1 | 1p13 | acute megakaryocytic leukaemia |
| RECQL4 | RecQ protein-like 4 | 8 | 8q24.3 | |
| REL | v-rel reticuloendotheliosis viral oncogene homolog (avian) | 2 | 2p13-p12 | Hodgkin lymphoma |
| RET | ret proto-oncogene | 10 | 10q11.2 | medullary thyroid, papillary thyroid, pheochromocytoma, NSCLC |
| RNF43 | Ring finger protein 43 | 17 | 17q22 | cholangiocarcinoma, ovary, pancreas |
| ROS1 | v-ros UR2 sarcoma virus oncogene homolog 1 (avian) | 6 | 6q22 | glioblastoma, NSCLC |
| RPL10 | ribosomal protein L10 | X | Xq28 | T-ALL |
| RPL22 | ribosomal protein L22 (EAP) | 1 | 1p36.31 | AML, CML |
| RPL5 | ribososomal protein L5 | 1 | 1p22.1 | T-ALL |
| RPN1 | ribophorin I | 3 | 3q21.3-q25.2 | AML |
| RUNDC2A | RUN domain containing 2A | 16 | 16p13.13 | PMBL, Hodgkin lymphoma |
| RUNX1 | runt-related transcription factor 1 (AML1) | 21 | 21q22.3 | AML, preB-ALL, T-ALL |
| RUNXBP2 | runt-related transcription factor binding protein 2 (MOZ/ZNF220) | 8 | 8p11 | AML |
| SBDS | Shwachman-Bodian-Diamond syndrome protein | 7 | 7q11 | |
| SDC4 | syndecan 4 | 20 | 20q12 | NSCLC |
| SDH5 | chromosome 11 open reading frame 79 | 11 | 11q12.2 | |
| SDHB | succinate dehydrogenase complex, subunit B, iron sulfur (Ip) | 1 | 1p36.1-p35 | |
| SDHC | succinate dehydrogenase complex, subunit C, integral membrane protein, 15 kDa | 1 | 1q21 | |
| SDHD | succinate dehydrogenase complex, subunit D, integral membrane protein | 11 | 11q23 | |
| SEPT6 | septin 6 | X | Xq24 | AML |
| SET | SET translocation | 9 | 9q34 | AML |
| SETBP1 | SET binding protein 1 | 18 | 18q21.1 | atypical CML |
| SETD2 | SET domain containing 2 | 3 | 3p21.31 | clear cell renal carcinoma |
| SF3B1 | splicing factor 3b, subunit 1, 155 kDa | 2 | 2q33.1 | myelodysplastic syndrome |
| SFPQ | splicing factor proline/glutamine rich(polypyrimidine tract binding protein associated) | 1 | 1p34.3 | papillary renal |
| SFRS3 | splicing factor, arginine/serine-rich 3 | 6 | 6p21 | follicular lymphoma |
| SH2B3 | SH2B adaptor protein 3 | 12 | 12q24.12 | MPD, sAML, erythrocytosis, B-ALL |
| SH3GL1 | SH3-domain GRB2-like 1 (EEN) | 19 | 19p13.3 | AL |
| SIL | TAL1 (SCL) interrupting locus | 1 | 1p32 | T-ALL |
| SLC34A2 | solute carrier family 34 (sodium phosphate), member 2 | 4 | 4p15.2 | NSCLC |
| SLC45A3 | solute carrier family 45, member 3 | 1 | 1q32 | prostate |
| SMARCA4 | SWI/SNF related, matrix associated, actin dependent regulator of chromatin, subfamily a, member 4 | 19 | 19p13.2 | NSCLC |

TABLE 1-continued

Examples of cancer genes

| Gene | Description | Chr | Chr Band | Tumor Types |
|---|---|---|---|---|
| SMARCB1 | SWI/SNF related, matrix associated, actin dependent regulator of chromatin, subfamily b, member 1 | 22 | 22q11 | malignant rhabdoid |
| SMARCE1 | SWI/SNF related, matrix associated, actin dependent regulator of chromatin, subfamily e, member 1 | 17 | 17q21.2 | |
| SMO | smoothened homolog (Drosophila) | 7 | 7q31-q32 | skin basal cell |
| SOCS1 | suppressor of cytokine signaling 1 | 16 | 16p13.13 | Hodgkin lymphoma, PMBL |
| SOX2 | SRY (sex determining region Y)-box 2 | 3 | 3q26.3-q27 | NSCLC, oesophageal squamous carcinoma |
| SRGAP3 | SLIT-ROBO Rho GTPase activating protein 3 | 3 | 3p25.3 | pilocytic astrocytoma |
| SRSF2 | serine/arginine-rich splicing factor 2 | 17 | 17q25 | MDS, CLL |
| SS18 | synovial sarcoma translocation, chromosome 18 | 18 | 18q11.2 | synovial sarcoma |
| SS18L1 | synovial sarcoma translocation gene on chromosome 18-like 1 | 20 | 20q13.3 | synovial sarcoma |
| SSH3BP1 | spectrin SH3 domain binding protein 1 | 10 | 10p11.2 | AML |
| SSX1 | synovial sarcoma, X breakpoint 1 | X | Xp11.23-p11.22 | synovial sarcoma |
| SSX2 | synovial sarcoma, X breakpoint 2 | X | Xp11.23-p11.22 | synovial sarcoma |
| SSX4 | synovial sarcoma, X breakpoint 4 | X | Xp11.23 | synovial sarcoma |
| STAT3 | signal transducer and activator of transcription 3 (acute-phase response factor) | 17 | 17q21.31 | T-cell large granular lymphocytic lymphoma |
| STK11 | serine/threonine kinase 11 gene (LKB1) | 19 | 19p13.3 | NSCLC, pancreatic |
| STL | Six-twelve leukemia gene | 6 | 6q23 | B-ALL |
| SUFU | suppressor of fused homolog (Drosophila) | 10 | 10q24.32 | medulloblastoma |
| SUZ12 | suppressor of zeste 12 homolog (Drosophila) | 17 | 17q11.2 | endometrial stromal tumour |
| SYK | spleen tyrosine kinase | 9 | 9q22 | MDS, peripheral T-cell lymphoma |
| TAF15 | TAF15 RNA polymerase II, TATA box binding protein (TBP)-associated factor, 68 kDa | 17 | 17q11.1-q11.2 | extraskeletal myxoid chondrosarcoma, ALL |
| TAL1 | T-cell acute lymphocytic leukemia 1 (SCL) | 1 | 1p32 | lymphoblastic leukaemia/biphasic |
| TAL2 | T-cell acute lymphocytic leukemia 2 | 9 | 9q31 | T-ALL |
| TCEA1 | transcription elongation factor A (SII), 1 | 8 | 8q11.2 | salivary adenoma |
| TCF1 | transcription factor 1, hepatic (HNF1) | 12 | 12q24.2 | hepatic adenoma, hepatocellular |
| TCF12 | transcription factor 12 (HTF4, helix-loop-helix transcription factors 4) | 15 | 15q21 | Extraskeletal, myxoid chondrosarcoma |
| TCF3 | transcription factor 3 (E2A immunoglobulin enhancer binding factors E12/E47) | 19 | 19p13.3 | pre B-ALL |
| TCF7L2 | transcription factor 7-like 2 | 10 | 10q25.3 | colorectal |
| TCL1A | T-cell leukemia/lymphoma 1A | 14 | 14q32.1 | T-CLL |
| TCL6 | T-cell leukemia/lymphoma 6 | 14 | 14q32.1 | T-ALL |
| TERT | telomerase reverse transcriptase | 5 | 5p15.33 | melanoma |
| TET2 | tet oncogene family member 2 | 4 | 4q24 | MDS |
| TFE3 | transcription factor binding to IGHM enhancer 3 | X | Xp11.22 | papillary renal, alveolar soft part sarcoma, renal |
| TFEB | transcription factor EB | 6 | 6p21 | renal cell carcinoma (childhood epithelioid) |

TABLE 1-continued

Examples of cancer genes

| Gene | Description | Chr | Chr Band | Tumor Types |
|---|---|---|---|---|
| TFG | TRK-fused gene | 3 | 3q11-q12 | papillary thyroid, ALCL, NSCLC |
| TFPT | TCF3 (E2A) fusion partner (in childhood leukaemia) | 19 | 19q13 | pre-B ALL |
| TFRC | transferrin receptor (p90, CD71) | 3 | 3q29 | NHL |
| THRAP3 | thyroid hormone receptor associated protein 3 (TRAP150) | 1 | 1p34.3 | aneurysmal bone cyst |
| TIF1 | transcriptional intermediary factor 1 (PTC6, TIF1A) | 7 | 7q32-q34 | APL |
| TLX1 | T-cell leukemia, homeobox 1 (HOX11) | 10 | 10q24 | T-ALL |
| TLX3 | T-cell leukemia, homeobox 3 (HOX11L2) | 5 | 5q35.1 | T-ALL |
| TMPRSS2 | transmembrane protease, serine 2 | 21 | 21q22.3 | prostate |
| TNFAIP3 | tumor necrosis factor, alpha-induced protein 3 | 6 | 6q23 | marginal zone B-cell lymphomas, Hodgkin lymphoma, PMBL |
| TNFRSF14 | tumor necrosis factor receptor superfamily, member 14 (herpesvirus entry mediator) | 1 | 1p36.32 | follicular lymphoma |
| TNFRSF17 | tumor necrosis factor receptor superfamily, member 17 | 16 | 16p13.1 | intestinal T-cell lymphoma |
| TNFRSF6 | tumor necrosis factor receptor superfamily, member 6 (FAS) | 10 | 10q24.1 | TGCT, nasal NK/T lymphoma, skin squamous cell carcinoma-burn scar related |
| TOP1 | topoisomerase (DNA) I | 20 | 20q12-q13.1 | AML* |
| TP53 | tumor protein p53 | 17 | 17p13 | breast, colorectal, lung, sarcoma, adrenocortical, glioma, multiple other tumour types |
| TPM3 | tropomyosin 3 | 1 | 1q22-q23 | papillary thyroid, ALCL, NSCLC |
| TPM4 | tropomyosin 4 | 19 | 19p13.1 | ALCL |
| TPR | translocated promoter region | 1 | 1q25 | papillary thyroid |
| TRA@ | T cell receptor alpha locus | 14 | 14q11.2 | T-ALL |
| TRAF7 | tumour necrosis factor receptor-associated factor 7 | 16 | 16p13.3 | meningioma |
| TRB@ | T cell receptor beta locus | 7 | 7q35 | T-ALL |
| TRD@ | T cell receptor delta locus | 14 | 14q11 | T-cell leukaemia |
| TRIM27 | tripartite motif-containing 27 | 6 | 6p22 | papillary thyroid |
| TRIM33 | tripartite motif-containing 33 (PTC7, TIF1G) | 1 | 1p13 | papillary thyroid |
| TRIP11 | thyroid hormone receptor interactor 11 | 14 | 14q31-q32 | AML |
| TSC1 | tuberous sclerosis 1 gene | 9 | 9q34 | renal cell carcinoma, bladder carcinoma |
| TSC2 | tuberous sclerosis 2 gene | 16 | 16p13.3 | pulmonary lymphangioleiomyomatosis (LAM), renal angiomyolipoma and head and neck cancer |
| TSHR | thyroid stimulating hormone receptor | 14 | 14q31 | toxic thyroid adenoma |
| TTL | tubulin tyrosine ligase | 2 | 2q13 | acute lymphocytic leukaemia |
| U2AF1 | U2 small nuclear RNA auxiliary factor 1 | 21 | 21q22.3 | chronic lymphatic leukaemia, myelodysplastic syndrome |
| USP6 | ubiquitin specific peptidase 6 (Tre-2 oncogene) | 17 | 17p13 | aneurysmal bone cyst |
| VHL | von Hippel-Lindau syndrome gene | 3 | 3p25 | renal, haemangioma, pheochromocytoma |
| VTI1A | vesicle transport through interaction with t-SNAREs homolog 1A | 10 | 10q25.2 | colorectal |
| WAS | Wiskott-Aldrich syndrome | X | Xp11.23-p11.22 | |
| WHSC1 | Wolf-Hirschhorn syndrome candidate 1 (MMSET) | 4 | 4p16.3 | Multiple myeloma |

TABLE 1-continued

Examples of cancer genes

| Gene | Description | Chr | Chr Band | Tumor Types |
|---|---|---|---|---|
| WHSC1L1 | Wolf-Hirschhorn syndrome candidate 1-like 1 (NSD3) | 8 | 8p12 | AML |
| WIF1 | WNT inhibitory factor 1 | 12 | 12q14.3 | pleomorphic salivary gland adenoma |
| WRN | Werner syndrome (RECQL2) | 8 | 8p12-p11.2 | |
| WT1 | Wilms tumour 1 gene | 11 | 11p13 | Wilms tumour, desmoplastic small round cell tumour |
| WTX | family with sequence similarity 123B (FAM123B) | X | Xq11.1 | Wilms tumour |
| WWTR1 | WW domain containing transcription regulator 1 | 3 | 3q23-q24 | epithelioid haemangioendothelioma |
| XPA | xeroderma pigmentosum, complementation group A | 9 | 9q22.3 | |
| XPC | xeroderma pigmentosum, complementation group C | 3 | 3p25 | |
| XPO1 | exportin 1 (CRM1 homolog, yeast) | 2 | 2p15 | CLL |
| YWHAE | tyrosine 3-monooxygenase/tryptophan 5-monooxygenase activation protein, epsilon polypeptide (14-3-3 epsilon) | 17 | 17p13.3 | edometrial stromal sarcoma |
| ZNF145 | zinc finger protein 145 (PLZF) | 11 | 11q23.1 | APL |
| ZNF198 | zinc finger protein 198 | 13 | 13q11-q12 | MPD, NHL |
| ZNF278 | zinc finger protein 278 (ZSG) | 22 | 22q12-q14 | Ewing sarcoma |
| ZNF331 | zinc finger protein 331 | 19 | 19q13.3-q13.4 | follicular thyroid adenoma |
| ZNF384 | zinc finger protein 384 (CIZ/NMP4) | 12 | 12p13 | ALL |
| ZNF521 | zinc finger protein 521 | 18 | 18q11.2 | ALL |
| ZNF9 | zinc finger protein 9 (a cellular retroviral nucleic acid binding protein) | 3 | 3q21 | aneurysmal bone cyst |
| ZRSR2 | zinc finger (CCCH type), RNA-binding motif and serine/arginine rich 2 | X | Xp22.1 | MDS, CLL |

TABLE 2

Exemplary microRNAs

| | | | | |
|---|---|---|---|---|
| hsa-miR-197 | hsa-miR-99b | hsa-miR-422a | hsa-miR-663b | hsa-miR-1272 |
| hsa-miR-23b | hsa-miR-30b | hsa-miR-375 | hsa-miR-325 | hsa-miR-20b |
| hsa-miR-1295 | hsa-miR-488* | hsa-miR-222 | hsa-miR-224 | hsa-miR-9 |
| hsa-miR-567 | hsa-miR-588 | hsa-miR-548d-5p | hsa-miR-875-3p | hsa-miR-1183 |
| hsa-miR-1268 | hsa-miR-1279 | hsa-miR-10a* | hsa-miR-181a* | hsa-miR-379* |
| hsa-miR-15b | hsa-miR-132 | hsa-miR-151-5p | hsa-miR-518e | hsa-miR-603 |
| hsa-miR-1246 | hsa-miR-185* | hsa-let-7a-1 | hsa-let-7a-2 | hsa-let-7a-3 |
| hsa-let-7e | hsa-let-7f-1 | hsa-let-7f-2 | hsa-let-7g | hsa-let-7i |
| hsa-mir-101-1 | hsa-mir-101-2 | hsa-mir-103-1 | hsa-mir-103-2 | hsa-mir-105-1 |
| hsa-mir-107 | hsa-mir-10a | hsa-mir-10b | hsa-mir-122 | hsa-mir-1226 |
| hsa-mir-1249 | hsa-mir-125a | hsa-mir-125b-1 | hsa-mir-125b-2 | hsa-mir-126 |
| hsa-mir-129-1 | hsa-mir-129-2 | hsa-mir-1291 | hsa-mir-1295 | hsa-mir-1296 |
| hsa-mir-132 | hsa-mir-133a-1 | hsa-mir-133a-2 | hsa-mir-133b | hsa-mir-134 |
| hsa-miR-107 | hsa-miR-767-3p | hsa-miR-422a | hsa-miR-1263 | hsa-miR-181a |
| hsa-mir-100 | hsa-miR-106b | hsa-miR-124-3 | hsa-miR-128-2 | hsa-miR-130b |
| hsa-let-7f | hsa-miR-662 | hsa-miR-325 | hsa-miR-1207-5p | hsa-miR-519a* |
| hsa-let-7c | hsa-mir-1-2 | hsa-mir-106a | hsa-mir-124-2 | hsa-mir-128-1 |
| hsa-let-7d | hsa-mir-135b | hsa-mir-136 | hsa-mir-137 | hsa-mir-138-1 |
| hsa-mir-139 | hsa-miR-139-5p | hsa-mir-140 | hsa-mir-141 | hsa-mir-142 |
| hsa-mir-144 | hsa-mir-145 | hsa-mir-146a | hsa-mir-146b | hsa-mir-147 |
| hsa-mir-148b | hsa-mir-149 | hsa-mir-150 | hsa-mir-151 | hsa-mir-152 |
| hsa-mir-153-2 | hsa-mir-154 | hsa-mir-155 | hsa-mir-15a | hsa-mir-15b |
| hsa-mir-16-2 | hsa-mir-17 | hsa-mir-181a-1 | hsa-mir-181a-2 | hsa-mir-181b-1 |
| hsa-mir-181c | hsa-mir-181d | hsa-mir-182 | hsa-mir-183 | hsa-mir-184 |
| hsa-mir-186 | hsa-mir-187 | hsa-mir-188 | hsa-mir-18a | hsa-mir-18b |
| hsa-mir-191 | hsa-mir-192 | hsa-mir-193a | hsa-mir-193a | hsa-mir-193b |
| hsa-mir-194-2 | hsa-mir-195 | hsa-mir-196a-1 | hsa-mir-196a-2 | hsa-mir-196b |
| hsa-mir-198 | hsa-mir-199a-1 | hsa-mir-199a-2 | hsa-mir-199b | hsa-mir-19a |

TABLE 2-continued

Exemplary microRNAs

| | | | | |
|---|---|---|---|---|
| hsa-mir-19b-2 | hsa-mir-200a | hsa-mir-200b | hsa-mir-200c | hsa-mir-202 |
| hsa-mir-204 | hsa-mir-205 | hsa-mir-206 | hsa-mir-208a | hsa-mir-20a |
| hsa-mir-21 | hsa-mir-210 | hsa-mir-211 | hsa-mir-212 | hsa-mir-214 |
| hsa-mir-216a | hsa-mir-217 | hsa-mir-218-1 | hsa-mir-218-2 | hsa-mir-219-1 |
| hsa-mir-22 | hsa-mir-220a | hsa-mir-221 | hsa-mir-222 | hsa-mir-223 |
| hsa-mir-23a | hsa-mir-23b | hsa-mir-24-1 | hsa-mir-24-2 | hsa-mir-25 |
| hsa-mir-26a-1 | hsa-mir-26a-2 | hsa-mir-26b | hsa-mir-27a | hsa-mir-27b |
| hsa-mir-296 | hsa-mir-299 | hsa-mir-29a | hsa-mir-29b-1 | hsa-mir-29b-2 |
| hsa-mir-301a | hsa-mir-302a | hsa-mir-302b | hsa-mir-302c | hsa-mir-302d |
| hsa-mir-30b | hsa-mir-30c-1 | hsa-mir-30c-2 | hsa-mir-30d | hsa-mir-30e |
| hsa-mir-32 | hsa-miR-32* | hsa-miR-320 | hsa-mir-320a | hsa-mir-323 |
| hsa-mir-325 | hsa-mir-326 | hsa-mir-328 | hsa-mir-329-1 | hsa-mir-329-2 |
| hsa-mir-331 | hsa-mir-335 | hsa-mir-337 | hsa-mir-338 | hsa-mir-339 |
| hsa-mir-33b | hsa-mir-340 | hsa-mir-342 | hsa-mir-345 | hsa-mir-346 |
| hsa-mir-34b | hsa-mir-34c | hsa-mir-361 | hsa-mir-362 | hsa-mir-363 |
| hsa-mir-365-2 | hsa-mir-367 | hsa-mir-369 | hsa-mir-370 | hsa-mir-371 |
| hsa-mir-373 | hsa-mir-374a | hsa-mir-374b | hsa-mir-375 | hsa-mir-376a-1 |
| hsa-mir-376c | hsa-mir-377 | hsa-mir-378 | hsa-mir-379 | hsa-mir-380 |
| hsa-mir-382 | hsa-mir-383 | hsa-mir-384 | hsa-mir-409 | hsa-mir-410 |
| hsa-mir-421 | hsa-mir-422a | hsa-mir-423 | hsa-mir-424 | hsa-mir-425 |
| hsa-mir-431 | hsa-mir-432 | hsa-mir-433 | hsa-mir-449a | hsa-mir-449b |
| hsa-mir-451 | hsa-mir-452 | hsa-mir-453 | hsa-mir-454 | hsa-mir-455 |
| hsa-mir-484 | hsa-mir-485 | hsa-mir-486 | hsa-mir-487a | hsa-mir-487b |
| hsa-mir-489 | hsa-mir-490 | hsa-mir-491 | hsa-mir-492 | hsa-mir-493 |
| hsa-mir-495 | hsa-mir-496 | hsa-mir-497 | hsa-mir-498 | hsa-mir-499 |
| hsa-mir-501 | hsa-mir-502 | hsa-mir-503 | hsa-mir-505 | hsa-mir-508 |
| hsa-mir-509-3 | hsa-mir-510 | hsa-mir-511-1 | hsa-mir-511-2 | hsa-mir-512-1 |
| hsa-mir-513a-1 | hsa-mir-513a-2 | hsa-mir-515-1 | hsa-mir-515-2 | hsa-mir-516a-1 |
| hsa-mir-516b-1 | hsa-mir-516b-2 | hsa-mir-517a | hsa-mir-517b | hsa-mir-517c |
| hsa-mir-518a-2 | hsa-mir-518b | hsa-mir-518c | hsa-mir-518d | hsa-mir-518e |
| hsa-mir-519a-1 | hsa-mir-519a-2 | hsa-mir-519b | hsa-mir-519c | hsa-mir-519d |
| hsa-mir-520a | hsa-mir-520b | hsa-mir-520c | hsa-mir-520d | hsa-mir-520e |
| hsa-mir-520g | hsa-mir-520h | hsa-mir-521-1 | hsa-mir-521-2 | hsa-mir-522 |
| hsa-mir-524 | hsa-mir-525 | hsa-mir-526a-1 | hsa-mir-526a-2 | hsa-mir-526b |
| hsa-mir-532 | hsa-mir-539 | hsa-mir-542 | hsa-mir-543 | hsa-mir-548o |
| hsa-mir-550-1 | hsa-mir-551a | hsa-mir-561 | hsa-mir-566 | hsa-mir-567 |
| hsa-mir-572 | hsa-mir-574 | hsa-mir-575 | hsa-mir-576 | hsa-mir-582 |
| hsa-mir-589 | hsa-mir-590 | hsa-mir-593 | hsa-mir-598 | hsa-mir-601 |
| hsa-mir-605 | hsa-mir-608 | hsa-mir-611 | hsa-mir-621 | hsa-mir-622 |
| hsa-mir-627 | hsa-mir-629 | hsa-mir-632 | hsa-mir-634 | hsa-mir-635 |
| hsa-mir-639 | hsa-mir-642 | hsa-mir-644 | hsa-mir-646 | hsa-mir-648 |
| hsa-mir-650 | hsa-mir-652 | hsa-mir-657 | hsa-mir-658 | hsa-mir-659 |
| hsa-mir-661 | hsa-mir-662 | hsa-mir-663 | hsa-mir-663b | hsa-mir-671 |
| hsa-mir-7-1 | hsa-mir-7-2 | hsa-mir-7-3 | hsa-mir-708 | hsa-mir-744 |
| hsa-mir-767 | hsa-miR-768-3p | hsa-mir-874 | hsa-mir-886 | hsa-mir-888 |
| hsa-miR-9 | hsa-mir-9-1 | hsa-mir-9-2 | hsa-mir-9-3 | hsa-mir-923 |
| hsa-mir-92a-2 | hsa-mir-92b | hsa-mir-93 | hsa-mir-95 | hsa-mir-96 |
| hsa-mir-99a | hsa-mir-99b | hsa-miR-99b* | mmu-mir-1-1 | mmu-mir-100 |
| mmu-mir-103-2 | mmu-mir-106a | mmu-mir-106b | mmu-mir-10a | mmu-mir-10b |
| mmu-mir-125b-1 | mmu-mir-126 | mmu-mir-130b | mmu-mir-133a-1 | mmu-mir-133b |
| mmu-mir-139 | mmu-mir-140 | mmu-mir-143 | mmu-mir-145 | mmu-mir-150 |
| mmu-mir-15a | mmu-mir-16-1 | mmu-mir-17 | mmu-mir-181a-1 | mmu-mir-181c |
| mmu-mir-184 | mmu-mir-18a | mmu-mir-192 | mmu-mir-193b | mmu-mir-196b |
| mmu-mir-19b-1 | mmu-mir-19b-2 | mmu-mir-203 | mmu-mir-207 | mmu-mir-20a |
| mmu-mir-210 | mmu-mir-22 | mmu-mir-222 | mmu-mir-223 | mmu-mir-23a |
| mmu-mir-25 | mmu-mir-27a | mmu-mir-27b | mmu-mir-290 | mmu-mir-292 |
| mmu-mir-298 | mmu-mir-29a | mmu-mir-29c | mmu-mir-301a | mmu-mir-30b |
| mmu-mir-31 | mmu-mir-322 | mmu-mir-33 | mmu-mir-346 | mmu-mir-351 |
| mmu-mir-365-1 | mmu-mir-375 | mmu-mir-378 | mmu-mir-450b | mmu-mir-466a |
| mmu-mir-468 | mmu-mir-486 | mmu-mir-500 | mmu-mir-503 | mmu-mir-542 |
| mmu-mir-669a-1 | mmu-mir-669c | mmu-mir-674 | mmu-mir-680-1 | mmu-mir-681 |
| mmu-mir-686 | mmu-mir-691 | mmu-mir-699 | mmu-mir-706 | mmu-mir-710 |
| mmu-mir-712 | mmu-mir-714 | mmu-mir-721 | mmu-mir-7a-1 | mmu-mir-7a-2 |
| mmu-mir-877 | mmu-mir-9-1 | mmu-mir-92a-1 | mmu-mir-93 | mmu-mir-99a |
| hsa-miR-424* | hsa-mir-605 | hsa-mir-34b | hsa-miR-663b | hsa-miR-202* |
| hsa-miR-663 | hsa-let-7b | hsa-mir-1-1 | hsa-mir-105-2 | hsa-mir-124-1 |
| hsa-mir-127 | hsa-mir-1307 | hsa-mir-135a-1 | hsa-miR-1305 | hsa-mir-135a-2 |
| hsa-miR-668 | hsa-mir-130a | hsa-mir-138-2 | hsa-mir-143 | hsa-mir-148a |
| hsa-mir-153-1 | hsa-mir-16-1 | hsa-mir-181b-2 | hsa-mir-185 | hsa-mir-190 |
| hsa-mir-194-1 | hsa-mir-197 | hsa-mir-19b-1 | hsa-mir-203 | hsa-mir-20b |
| hsa-mir-215 | hsa-mir-219-2 | hsa-mir-224 | hsa-miR-26a | hsa-mir-28 |
| hsa-mir-29c | hsa-mir-30a | hsa-mir-31 | hsa-mir-324 | hsa-mir-330 |
| hsa-mir-33a | hsa-mir-34a | hsa-mir-365-1 | hsa-mir-372 | hsa-mir-376b |
| hsa-mir-381 | hsa-mir-412 | hsa-mir-429 | hsa-mir-450a-1 | hsa-mir-483 |
| hsa-mir-488 | hsa-mir-494 | hsa-mir-500 | hsa-mir-509-1 | hsa-mir-512-2 |
| hsa-mir-516a-2 | hsa-mir-518a-1 | hsa-mir-518f | hsa-mir-519e | hsa-mir-520f |
| hsa-mir-523 | hsa-mir-527 | hsa-miR-550 | hsa-mir-571 | hsa-mir-584 |
| hsa-mir-604 | hsa-mir-625 | hsa-mir-637 | hsa-mir-649 | hsa-mir-660 |

TABLE 2-continued

Exemplary microRNAs

| hsa-miR-7 | hsa-mir-766 | hsa-mir-891a | hsa-mir-92a-1 | hsa-mir-98 |
|---|---|---|---|---|
| mmu-mir-103-1 | mmu-mir-125a | mmu-mir-138-2 | mmu-mir-155 | mmu-mir-182 |
| mmu-mir-199b | mmu-mir-20b | mmu-mir-23b | mmu-mir-296 | mmu-mir-30e |
| mmu-mir-363 | mmu-mir-467a | mmu-mir-652 | mmu-mir-685 | mmu-mir-711 |
| mmu-mir-805 | | | | |

Example 9

As described herein, large oncosomes (LO) contain kinase activity and induce angiogenesis and transcription factor activation in the tumor microenvironment. Specifically, large oncosomes contain active Akt kinase that may serve as a prognostic marker and therapeutic target. LO contain active kinases (such as Akt) which may activate c-Myc when internalized by recipient cells, resulting in cell proliferation and angiogenesis (and therefore cancer metastasis). Therefore, kinase inhibitors may be used as therapeutic agents, for example, to target LO.

Figure 20A:
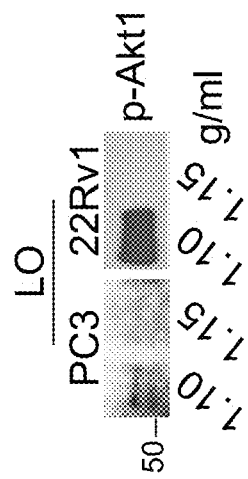
FIG. 20A to FIG. 20B depict in accordance with an embodiment of the invention that p-Akt is exported in large oncosomes (LO) from prostate cancer cell lines.
Figure 20B:
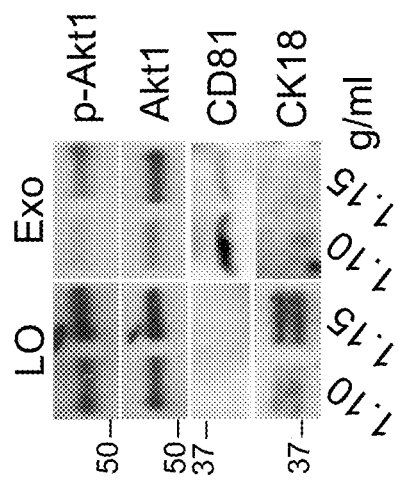

As shown in FIG. 20, p-Akt is exported in large oncosomes (LO) from prostate cancer cell lines. LO and Exo isolation from LNCaPMyrAkt1, PC3 and 22Rv1 cells was performed by differential high-speed centrifugation (10,000×g and 100,000×g) followed by discontinuous density gradient centrifugation. Western Blot for the indicated proteins has been performed on 1.10 and 1.15 g/ml fractions that both contain LO markers.

Figures 21A, 21B:
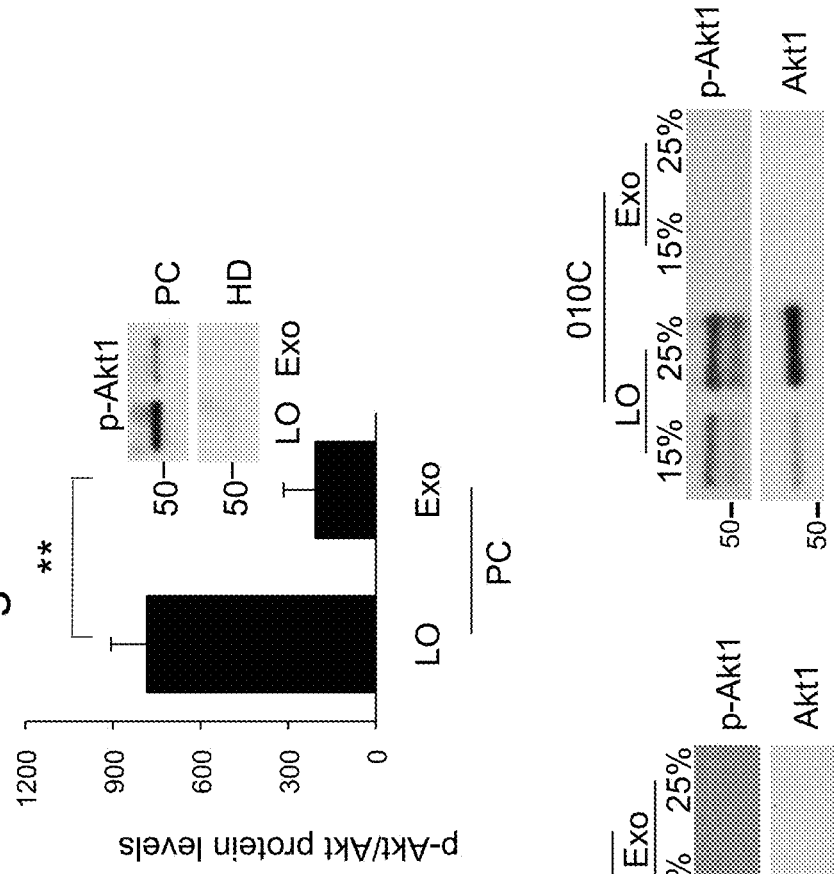
FIG. 21A to FIG. 21B depict in accordance with an embodiment of the invention that p-Akt1 can be detected in plasma derived large oncosomes from patients with prostate cancer.

As shown in FIG. 21, p-Akt1 can be detected in plasma derived large oncosomes from patients with prostate cancer. LO and Exo isolation was performed by differential high-speed centrifugation (10,000×g and 100,000×g) followed discontinuous density gradient centrifugation. 500 µl of plasma either from prostate cancer patients or healthy control was used as LO and Exo source. Western Blot for p-Akt1 (Ser473) and Akt1 has been performed after extracellular vesicles isolation. Bar plot shows the average of the p-Akt1 band intensity, obtained by WB, as measured by imageJ and normalized over the total amount of protein.

Figure 22B:
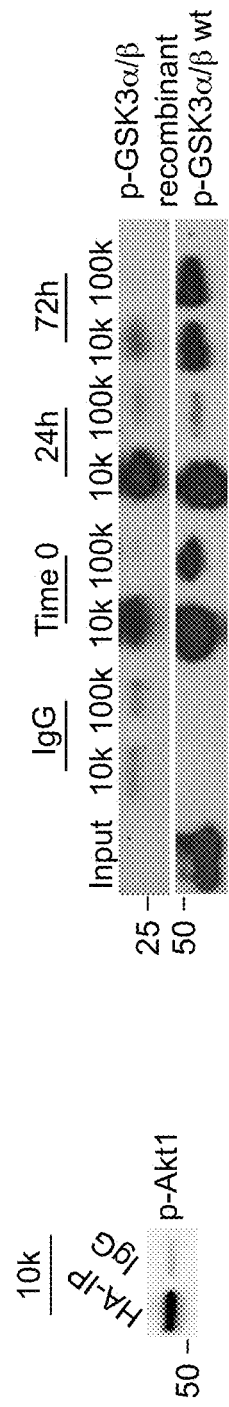
FIG. 22A to FIG. 22B depict in accordance with an embodiment of the invention that LO harbor active Akt1.
Figure 22A:
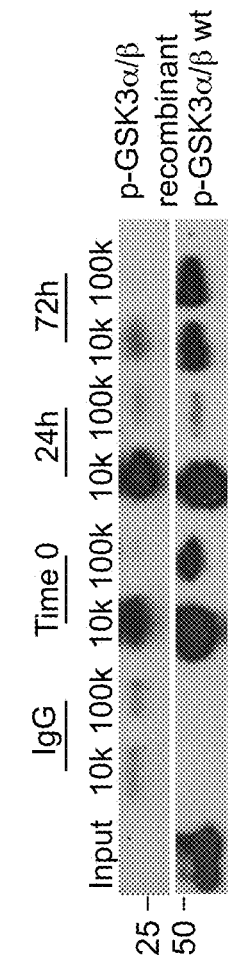
Figure 23E:
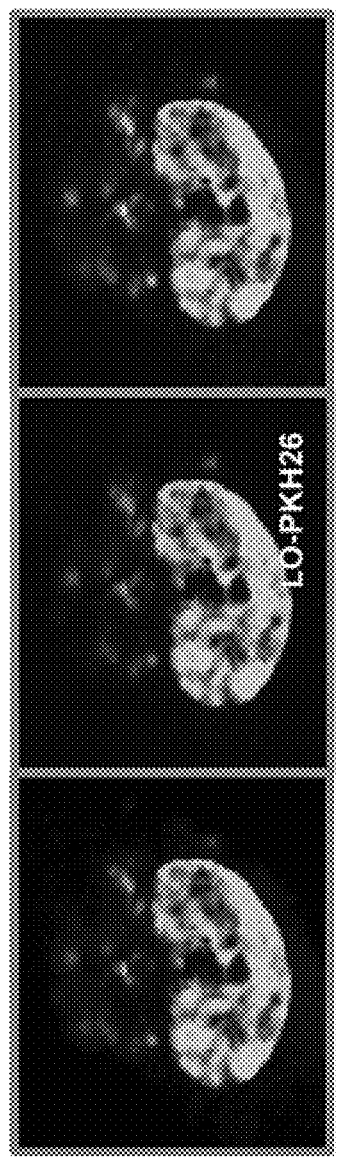
Figure 23F:
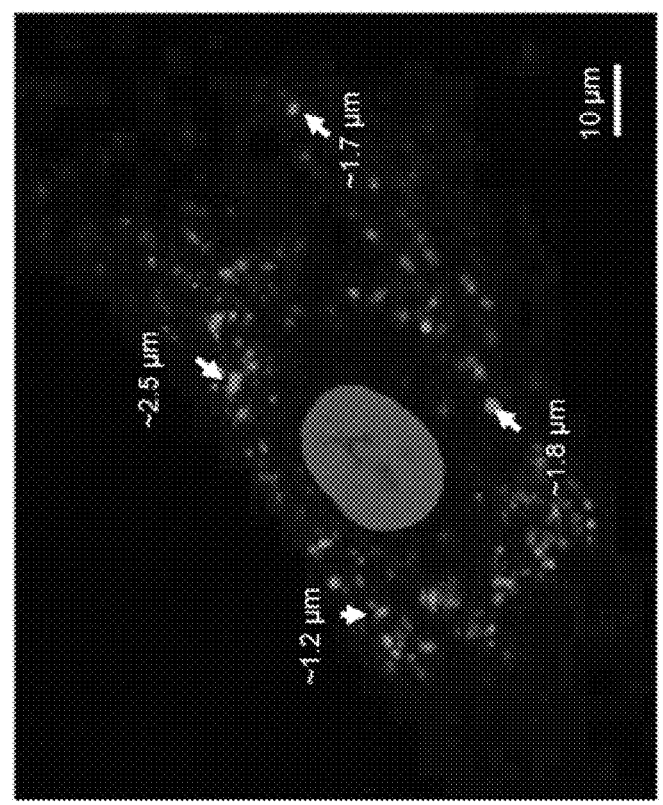

As shown in FIG. 22, p-Akt kinase in large oncosomes is active. LO and Exo isolation was performed by differential high-speed centrifugation (10,000×g and 100,000×g). Conditioned media from LNCaPMyrAkt1 was used as source for LO and Exo. Immunoprecipitation for Akt1 in, LO and Exo, was performed using an HA antibody able to recognize the tag on the MyrAkt1 overexpressed protein. The IP product was used for either test p-Akt1 level by WB or to perform an Akt1 kinase activity assay using a kit provided by Cell Signaling As shown in FIG. 23 LO internalization differs between cells. LO isolation was performed using a filtration approach where the larger vesicles are retained by the filter and the smaller ones flow through. To test LO uptake, LO were labeled with a lipophilic dye, PKH26 and then used to treat target cells for 1 h at 37° C. LO uptake levels have been measured as the acquisition of fluorescence by target cells either by FACS or confocal imaging.

Figure 24B:
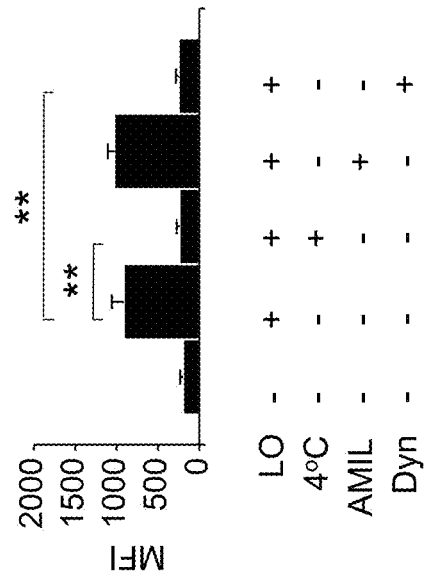
Figure 24A:
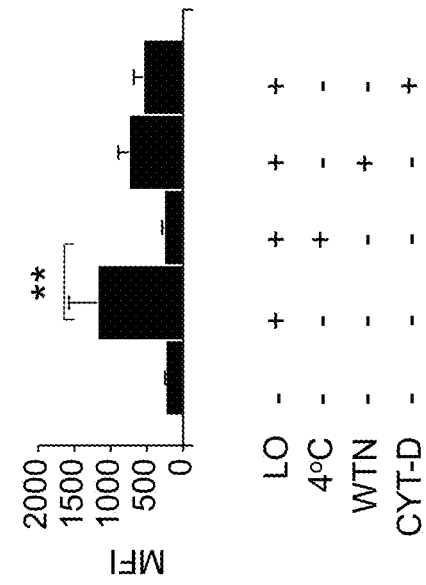
Figure 24C:
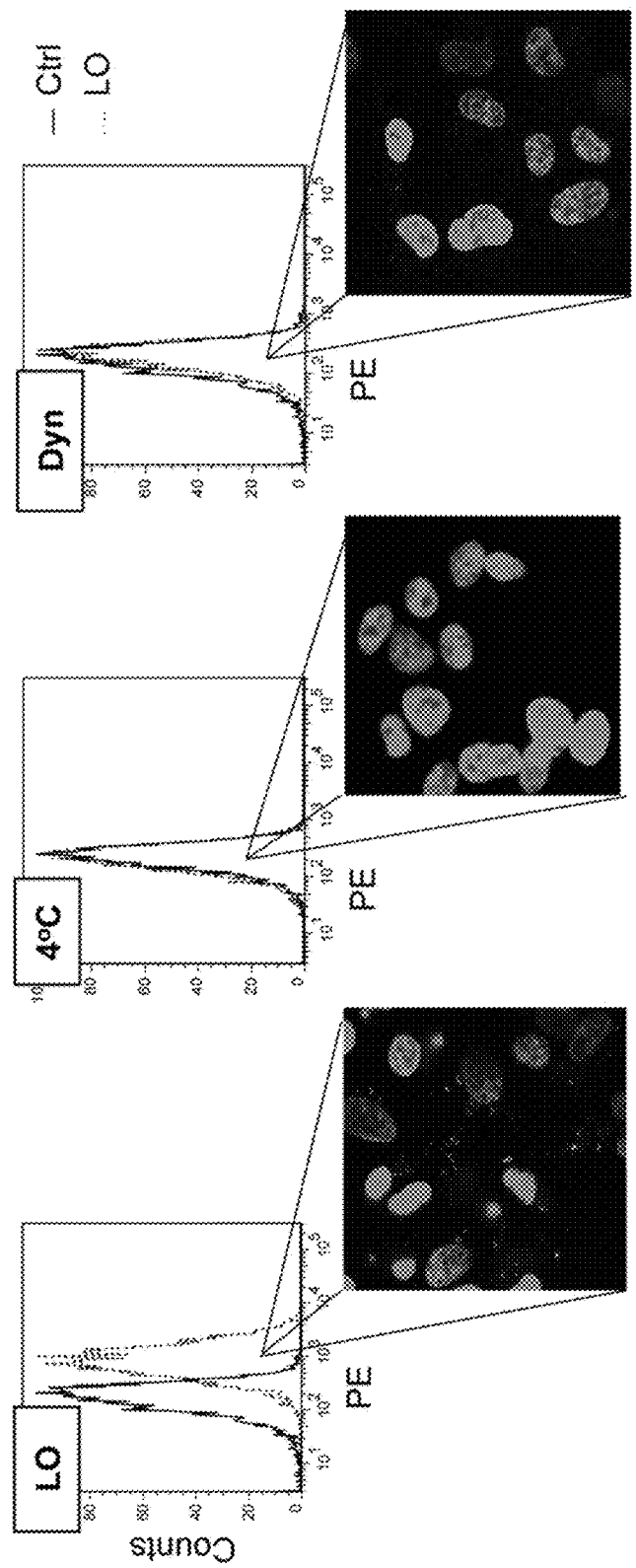

As shown in FIG. 24, large oncosome internalization is inhibited by Dyn. LO isolation was preformed using a filtration approach where the larger vesicles are retained by the filter and the smaller ones flow through. To test LO uptake LO were labeled with a lipophilic dye, PKH26 and then used to treat target cells for 1 h at 37° C. or 4° C. in presence or absence of the indicated compounds. LO uptake levels were measured as the acquisition of fluorescence by target cells either by FACS and fluorescent imaging. Dynamin2 silencing has been performed by transient transfection of WPMY-1 cells with an oligos against Dynamin2.

Figure 25:
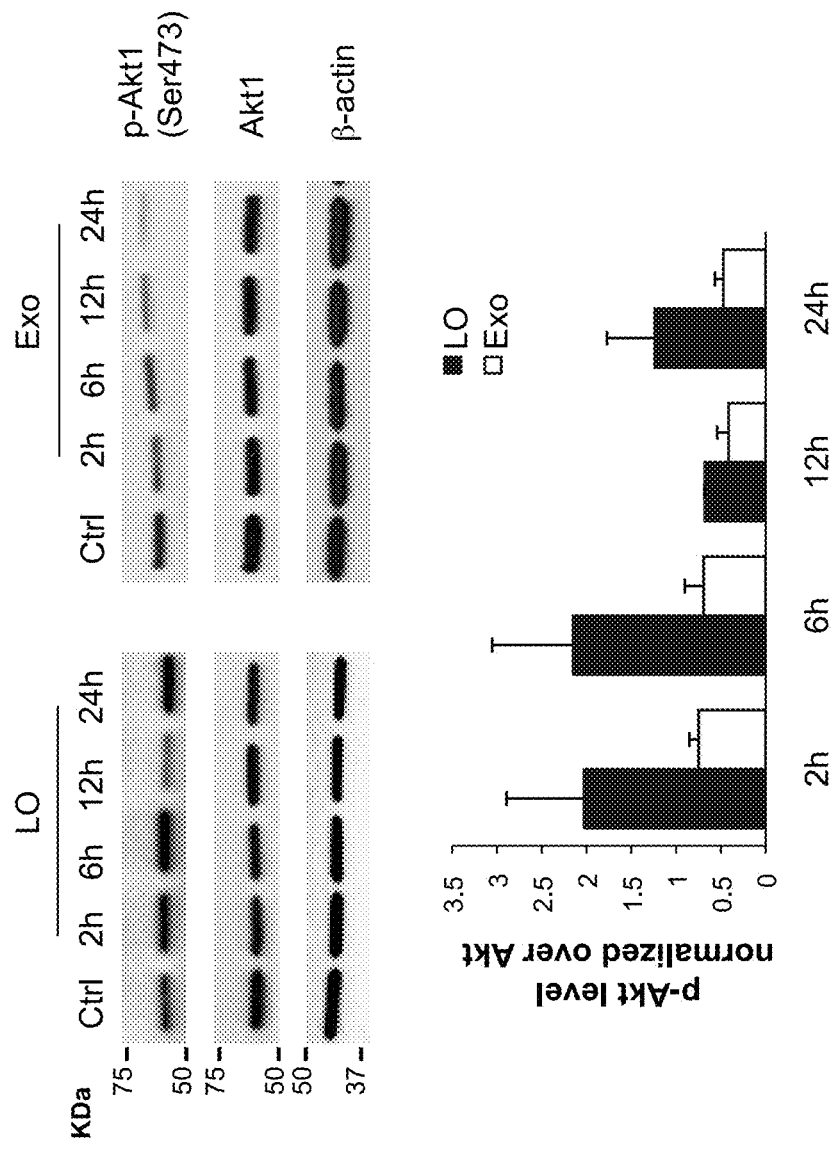
FIG. 25 depicts in accordance with an embodiment of the invention that large oncosomes induce Akt activation in recipient cells. Whole cell protein lysate from NAF exposed to LO or Exo for the indicated times was blotted with p-Akt1 and Akt1 antibodies. Bar plots show the average, after ImageJ quantification, of three biological replicates of p-Akt1 levels, normalized over total Akt1.

As shown in FIG. 25, transfer of MyrAkt1 and p-Akt signaling activation is mediated by large oncosomes. LO and Exo isolation was performed by differential high-speed centrifugation (10,000×g and 100,000×g) followed by discontinuous density gradient centrifugation. Conditioned media from LNCaPMyrAkt1 was used as source for LO and Exo. Western blot for p-Akt1 (Ser473) and Akt1 was performed in whole cell lysate after treatment with LO or Exo 20 µg/ml. Bar plot shows the average of the p-Akt1 band intensity obtained by WB, as measured by imageJ and normalized over the total Akt1.

Figure 26A:
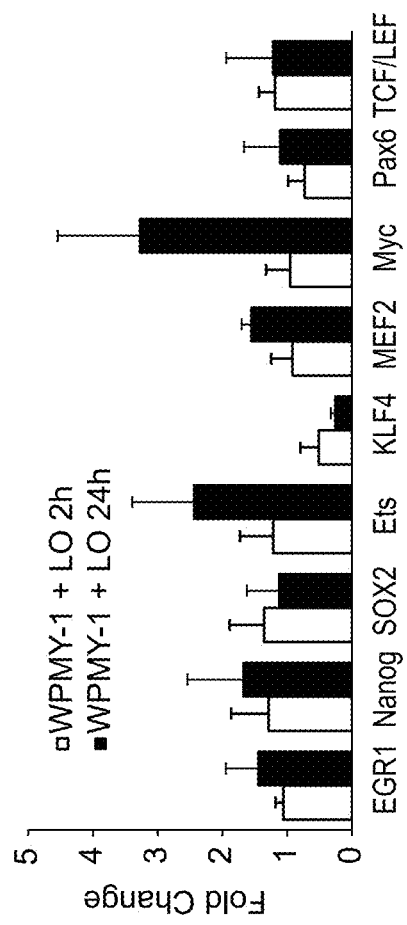
FIG. 26A to FIG. 26C depict in accordance with an embodiment of the invention that large oncosome internalization results in altered transcription factor activity in recipient stroma.
Figure 26B:
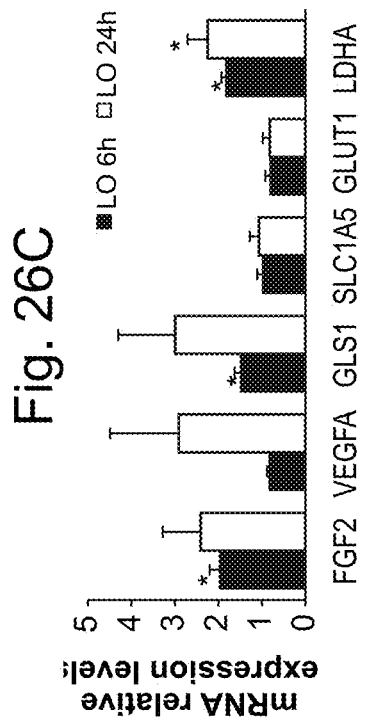
Figure 26C:
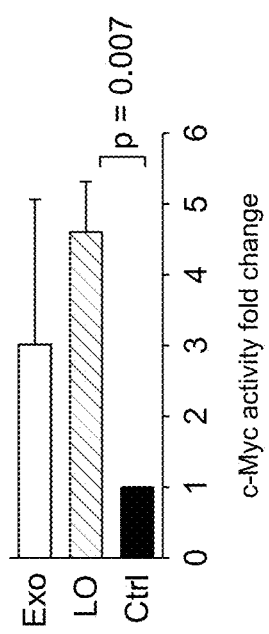

As shown in FIG. 26, large oncosomes alter the activity of transcription factors in recipient cells. LO and Exo isolation was performed by differential high-speed centrifugation (10,000×g and 100,000×g) followed discontinuous density gradient centrifugation. Conditioned media from LNCaPMyrAkt1 was used as source for LO and Exo. Nuclear extract from WPMY-1 cells treated with LO for the indicated time was used to perform the transcription factor activation profiling array from Signosis. Luciferase reporter assay for c-Myc promoter activation has been performed in NAF transfected with c-Myc promoter or vector plasmid treated with either LO or Exo 20 µg/ml for 6 h. RT-qPCR for c-Myc target cells in NAF treated with either LO or Exo 20 µg/ml for 6 h or 24 h.

As shown in FIG. 27, LO induce a robust tube formation. LO and Exo isolation was performed by differential high-speed centrifugation (10,000×g and 100,000×g) followed by discontinuous density gradient centrifugation. Conditioned media from LNCaPMyrAkt1 was used as source for LO and Exo. Tube formation assay in endothelial cells, HUVEC treated with LO or Exo 20 µg/ml directly or with conditioned media from NAF previously exposed to either LO or Exo. After 6 h-8 h tube formation rate is recorded by imaging, and quantified by counting the branching points in randomly chosen fields from each condition.

Figure 28B:
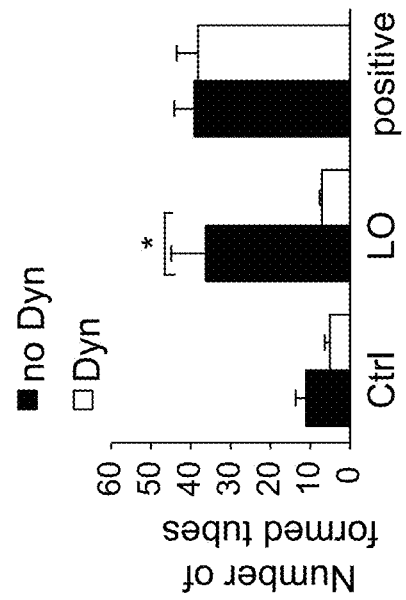
FIG. 28A to FIG. 28B depict in accordance with an embodiment of the invention that inhibition of LO uptake reduce LO effect in recipient cells.
Figure 28A:
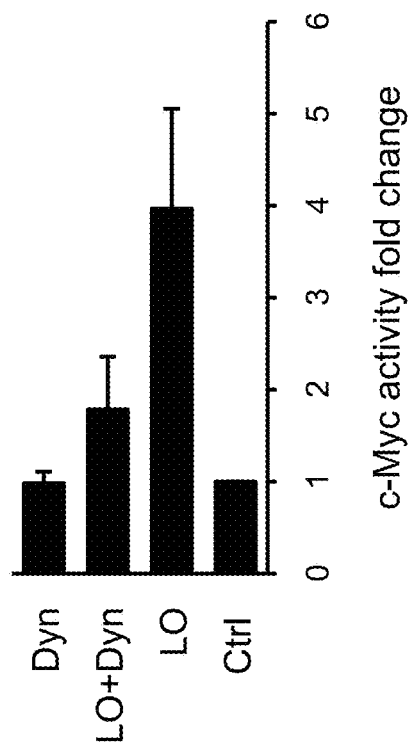

As shown in FIG. 28, inhibition of LO uptake reduces LO effect in recipient cells. LO and Exo isolation was performed by differential high-speed centrifugation (10,000×g and 100,000×g) followed by discontinuous density gradient centrifugation. Conditioned media from LNCaPMyrAkt1 was used as source for LO and Exo. Luciferase reporter assay for c-Myc promoter activation was performed in NAF transfected with c-Myc promoter or vector plasmid treated with either LO or Exo 20 µg/ml for 6 h in presence or absence of Dynasore 20 nM. Tube formation assay in endothelial cells, HUVEC treated with LO or Exo 20 µg/ml directly in presence or absence of Dynasore 20 nM. After for 6 h-8 h tube formation rate is recorded by imaging, and quantified by counting the branching points in randomly chosen fields from each condition.

Figure 29:
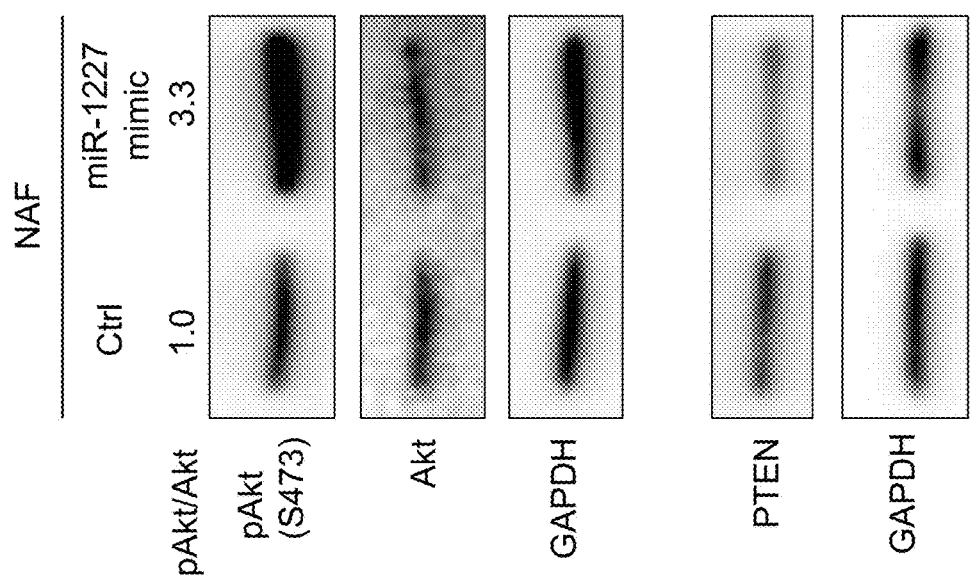
FIG. 29 depicts in accordance with an embodiment of the invention that PTEN is downregulated by miR-1227. The data shows that LO resident miR1227 might contribute to activate Akt signaling in NAFs. WB showing reduced PTEN and increased p-Akt1 expression upon forced expression of miR1227 in NAF.

As shown in FIG. 29, PTEN is downregulated by miR-1227. Western Blot for Akt1, p-Akt1 (Ser473) and PTEN in whole cell lysate from NAF transiently overexpressing miR-1227 mimic or scramble is shown.

Various embodiments of the invention are described above. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

The invention claimed is:

1. A method of detecting a level of large oncosomes and a level of proteins in large oncosomes, comprising:
   (i) providing a sample from a subject with cancer;
   (ii) isolating large oncosomes from the sample; and
   (iii) detecting the presence of proteins in the large oncosomes, wherein the proteins are GLS, ATP5O, PPP2R1A, SFXN1, ECI, HBA1, HINT2, TUFM, ANP32A, PGLS, ETFA, CRYZ, MGST1, CYB5R3, TMEM33, PHB, TOP2A, KIF5B, APEX1, and RDH11;
   (iv) determining that the level of large oncosomes is increased if it is higher than a reference value for large oncosomes; and
   (v) determining that the protein is at an increased level if it is higher than a reference value for said protein.

2. The method of claim 1, wherein the sample is blood, plasma or a combination thereof.

3. The method of claim 1, wherein the subject has prostate cancer.

4. The method of claim 1, wherein the sample from the subject is obtained before, during or after cancer treatment.

5. The method of claim 1, wherein the subject is human.

6. The method of claim 1, wherein the reference value is: (i) the mean or median number of large oncosomes and/or the protein levels in a population of subjects that do not have cancer; (ii) the mean or median number of large oncosomes and/or the protein levels in a population of subjects that have cancer in remission; or (iii) the mean or median number of large oncosomes and/or the protein levels in one or more samples from the subject wherein the one or more samples are obtained from a different time point.

7. The method of claim 1, further comprising detecting the presence of micro RNAs in the large oncosomes, wherein (i) the micro RNA is any one or more of miR-491-3p, miR-34b, miR-1228, miR-647, miR-1227 or a combination thereof.

8. The method of claim 7, wherein detecting the presence of micro RNAs in the large oncosomes comprises detecting the micro RNAs miR-491-3p, miR-34b, miR-1228, miR-647 and miR-1227.

9. The method of claim 7, wherein the reference value is the mean or median number of large oncosomes and/or micro RNA levels in a population of subjects that do not have cancer.

10. The method of claim 7, wherein the reference value is the mean or median number of large oncosomes and/or micro RNA levels in a population of subjects that have cancer in remission.

11. The method of claim 7, wherein the reference value is the mean or median number of large oncosomes and/or micro RNA levels in one or more samples from the subject wherein the one or more samples are obtained from a different time point.

12. The method of claim 1, further comprising prescribing any one or more of surgery, radiation, chemotherapy, immunotherapy, vaccine or a combination thereof, to the subject with cancer.

* * * * *